US012577580B2

(12) United States Patent
Sirizzotti et al.

(10) Patent No.: US 12,577,580 B2
(45) Date of Patent: *Mar. 17, 2026

(54) SEEDLESS FRUIT PRODUCING PLANTS

(71) Applicant: NUNHEMS B.V., Nunhem (NL)

(72) Inventors: Alberto Sirizzotti, Crema (IT);
Richard Bernard Berentsen, La
Palma-Cartagena (ES); **Hendrik
Willem Vriezen**, Nunhem (NL)

(73) Assignee: NUNHEMS B.V., Nunhem (NL)

( * ) Notice: Subject to any disclaimer, the term of this
patent is extended or adjusted under 35
U.S.C. 154(b) by 139 days.

This patent is subject to a terminal dis-
claimer.

(21) Appl. No.: 18/365,753

(22) Filed: Aug. 4, 2023

(65) Prior Publication Data

US 2024/0018539 A1      Jan. 18, 2024

Related U.S. Application Data

(60) Continuation of application No. 17/500,665, filed on
Oct. 13, 2021, now Pat. No. 11,761,018, which is a
division of application No. 16/304,228, filed as
application No. PCT/EP2017/062093 on May 19,
2017, now Pat. No. 11,174,493.

(30) Foreign Application Priority Data

May 26, 2016    (EP) .................................... 16171462

(51) Int. Cl.
C12N 15/82         (2006.01)
C07K 14/415        (2006.01)
(52) U.S. Cl.
CPC .......... C12N 15/829 (2013.01); C07K 14/415
(2013.01); C12N 15/8218 (2013.01)
(58) Field of Classification Search
None
See application file for complete search history.

(56) References Cited

U.S. PATENT DOCUMENTS

| | | | | |
|---|---|---|---|---|
| 11,174,493 | B2 * | 11/2021 | Sirizzotti | ............. C12N 15/829 |
| 11,761,018 | B2 * | 9/2023 | Sirizzotti | ............. C12N 15/829 |
| | | | | 800/290 |
| 2013/0219558 | A1 * | 8/2013 | Kragler | ............. C12N 15/8202 |
| | | | | 800/278 |

FOREIGN PATENT DOCUMENTS

| | | | |
|---|---|---|---|
| EP | 0120516 | A2 | 10/1984 |
| EP | 0292435 | A1 | 11/1988 |
| EP | 0321201 | B1 | 6/1989 |
| EP | 0465875 | A1 | 1/1992 |
| EP | 0513849 | A2 | 11/1992 |
| WO | 9307279 | A1 | 4/1993 |
| WO | 9418313 | A1 | 8/1994 |
| WO | 9506128 | A2 | 3/1995 |
| WO | 9509233 | A1 | 4/1995 |
| WO | 9515972 | A1 | 6/1995 |
| WO | 9704112 | A2 | 2/1997 |
| WO | 9704113 | A2 | 2/1997 |
| WO | 9837213 | A1 | 8/1998 |
| WO | 9837214 | A1 | 8/1998 |
| WO | 99053050 | A1 | 10/1999 |
| WO | 174144 | A1 | 10/2001 |
| WO | 2003004659 | A2 | 1/2003 |
| WO | 2003080809 | A2 | 10/2003 |
| WO | 2004067736 | A2 | 8/2004 |
| WO | 2007047859 | A2 | 4/2007 |
| WO | 2010079430 | A1 | 7/2010 |
| WO | 2011072246 | A2 | 6/2011 |
| WO | 2011146121 | A1 | 11/2011 |
| WO | 2011154393 | A1 | 12/2011 |
| WO | 2012001527 | A2 | 1/2012 |
| WO | 2012069539 | A1 | 5/2012 |
| WO | 2012093833 | A2 | 7/2012 |
| WO | 2012104729 | A1 | 8/2012 |
| WO | 2012138927 | A2 | 10/2012 |
| WO | 2012138939 | A1 | 10/2012 |
| WO | 2015136532 | A1 | 9/2015 |

OTHER PUBLICATIONS

Acciarri et al., "Genetically modified parthenocarpic eggplants:
improved fruit productivity under both greenhouse and open field
cultivation," BMC Biotechnology, 2002, vol. 2, No. 4, pp. 1-7.
Allen et al., "Transcript-specific, single-nucleotide polymorphism
discovery and linkage analysis in hexaploid bread wheat (*Triticum
aestivum* L.)," Plant Biotechnology Journal, 2011, vol. 9, pp.
1086-1099.
Azumi et al., "Homolog interaction during meiotic prophase I in
*Arabidopsis* requires the Solo Dancers gene encoding a novel
cyclin-like protein," The EMBO Journal, 2002, vol. 21, No. 12, pp.
3081-3095.
Chang et al., "Functional conservation of the meiotic genes SDS and
RCK in male meiosis in the monocot rice," Cell Research, Jun.
2009, vol. 19, No. 6, pp. 768-782.
Christian et al., "Targeting DNA Double-Strand Breaks with TAL
Effector Nucleases," Genetics, Oct. 2010, vol. 186, pp. 757-761.
Database Geneseq [Online], Jun. 11, 2007, "*Arabidopsis thaliana*
SDS cDNA.", XP002772148, retrieved from EBI accession No.
GSN:AAD21310, Database accession No. AAD21310 & WO 01/74144
Al (Univ Penn Sylvania [US]; MA Hong [US]) Oct. 11, 2001 (Oct.
11, 2001).
Database Uniprot [Online] XP002762418, retrieved from EBI acces-
sion No. Uniprot: A0A0A0KPH6 , Jan. 7, 2015.

(Continued)

*Primary Examiner* — Cynthia E Collins
(74) *Attorney, Agent, or Firm* — ArentFox Schiff LLP

(57)         ABSTRACT

The present invention is directed to seedless fruit producing
plants. The present invention also comprises methods for
production of said plants and the use of nucleic acids
encoding cyclin SDS like proteins for the production of
seedless fruits.

11 Claims, 3 Drawing Sheets

Specification includes a Sequence Listing.

(56) References Cited

OTHER PUBLICATIONS

De Muyt et al., "A High Throughput Genetic Screen Identifies New Early Meiotic Recombination Functions in *Arabidopsis thaliana*," PLOS Genetics, Sep. 2009, vol. 5, No. 9, pp. 1-14.

Guner et al., "The Genes of Watermelon," Hort Science, 2004, vol. 39, No. 6, pp. 1175-1182.

Guo et al., "The draft genome of watermelon (*Citrullus lanatus*) and resequencing of 20 diverse accessions," Nature Genetics, Jan. 2013, vol. 45, No. 1, pp. 51-58.

International Search Report in PCT/EP2017/062093, mailed Jul. 17, 2017.

Isalan et al., "A rapid, generally applicable method to engineer zinc fingers illustrated by targeting the HIV-1 promoter," Nature Biotechnology, 2001, vol. 19, No. 7, pp. 656-660.

Jinek et al., "A programmable Dual-RNA-Guided DNA Endonuclease in Adaptive Bacterial Immunity," Science, Aug. 17, 2012, vol. 337, pp. 816-821.

Koonin et al., "Orthologs, Paralogs, and Evolutionary Genomics," The Annual Review of Genetics, 2005, vol. 39, pp. 309-338.

Liu et al., "Design of polydactyl zinc-finger proteins for unique addressing within complex genomes," Proceedings of the National Academy of Sciences, May 1997, vol. 94, pp. 5525-5530.

McCallum et al., "Targeting Induced Local Lesions in Genomes (TILLING) for Plant Functional Genomics," Plant Physiology, Jun. 2000, vol. 123, pp. 439-442.

Mette et al., "Transcriptional silencing and promoter methylation triggered by double-stranded RNA," The EMBO Journal, 2000, vol. 19, No. 19, pp. 5194-5201.

Mouscou et al., "A Simple Cipher Governs DNA Recognition by TAL Effectors," Science, Dec. 11, 2009, vol. 326, pp. 1501.

Pradillo et al., "On the role of AtDMC1, AtRAD51 and its paralogs during *Arabidopsis meiosis*," Frontiers in Plant Science, Feb. 2014, vol. 5, Article 23, pp. 1-13.

Rotino et al., "Open field trial of genetically modified parthenocarpic tomato: seedlessness and fruit quality," BMC Biotechnology, 2005, vol. 5, No. 32, pp. 1-8.

Ruan et al., "Molecular regulation of seed and fruit set," Trends in Plant Science, 2012, vol. 17, No. 11, pp. 1360-1385.

Sjolander et al., "Phylogenomic inference of protein molecular function: advances and challenges," Bioinformatics, 2004, vol. 20, No. 2, pp. 170-179.

Thomson, M., "High-Throughput SNP Genotyping to Accelerate Crop Improvement," Plant Breeding and Biotechnology, Sep. 2014, vol. 2, No. 3, pp. 195-212.

Thorneycroft et al., "Using gene knockouts to investigate plant metabolism," Journal of Experimental Botany, Aug. 2001, vol. 52, No. 361, pp. 1593-1601.

Tiedemann et al., "Dissection of a complex seed phenotype: novel insights of FUSCA3 regulated developmental processes," Developmental Biology, 2008, vol. 317, pp. 1-12.

Yin et al., "The DefH9-iaaM-Containing Construct Efficiently Induces Parthenocarpy in Cucumber," Cellular & Molecular Biology Letters, 2006, vol. 11, pp. 279-290.

Zhang et al., "Characteristics of a novel male-female sterile watermelon (*Citrulus lanatus*) mutant," Scientia Horticulturae, 2012, vol. 140, pp. 107-114.

Zhou et al., "The plant cyclin-dependent kinase inhibitor ICK1 has distinct functional domains for in vivo kinase inhibition, protein instability and nuclear localization," The Plant Journal, 2003, vol. 35, No. 4, pp. 476-489.

* cited by examiner

SEEDLESS FRUIT PRODUCING PLANTS

CROSS-REFERENCE TO RELATED APPLICATIONS

This application is a continuation of U.S. application Ser. No. 17/500,665, filed Oct. 13, 2021, which is a divisional of U.S. application Ser. No. 16/304,228, filed Nov. 23, 2018, which is a National Stage Entry of PCT/EP2017/062093, filed May 19, 2017, which claims priority to EP patent application Ser. No. 16/171,462.1, filed on May 26, 2016, the disclosures of which are hereby incorporated by reference in their entireties.

REFERENCE TO AN ELECTRONIC SEQUENCE LISTING

The contents of the electronic sequence listing (BCS 16-8014_SEQLISTING_ST26.xml; Size: 47,188 bytes; and Date of Creation: Aug. 2, 2023) is herein incorporated by reference in its entirety.

The present invention is directed to seedless fruit producing plants. The present invention also comprises methods for production of said plants and the use of nucleic acids encoding cyclin SDS like proteins for the production of seedless fruits.

Most commercial seedless fruits have been developed from plants whose fruits normally contain numerous relatively large hard seeds distributed throughout the flesh of the fruit. Seedless fruits are e.g. known for watermelon, tomato, cucumber, eggplant, grapes, banana, citrus fruits, such as orange, lemon and lime. As consumption of seedless fruits is generally easier and more convenient, they are considered valuable.

Fruit development normally begins when one or more egg cells in the ovular compartment of the flower are fertilized by sperm nuclei from pollen.

Seedless fruits can result from two different phenomena. In some cases fruit develops without fertilization of the ovule by pollen, a phenomenon known as parthenocarpy. In other cases seedless fruits occur after pollination when seed (embryo and/or endosperm) growth is inhibited or the seed dies early, while the remainder of the fruit continues to grow (stenospermocarpy). In contrast to parthenocarpy, stenospermocarpy requires pollination for initiation of fruit growth.

Seedless orange fruits are an example for parthenocarpy. Some orange varieties (e.g. Navel) do not produce viable pollen. They however can be cross-pollinated with pollen from other varieties. In case only the male sterile variety is grown in an orchard, there will be no pollination and parthenocarp seedless fruits will be produced. Propagation of the respective orange trees is commonly done by cuttings followed by grafting to another rootstock.

Seedless bananas are triploid. Although pollination in some cases can be normal and, the vast majority of fruits is seedless. This is explained by the uneven sets of chromosomes (3×) leading to improper division of chromosomes during meiosis and as a consequence to the production of non-viable pollen. Without fertilization, triploid bananas are also able to set and develop seedless fruits. Even when pollination takes place, at most one in three hundred fruits comprises a few seeds. This may be due to the triploid pollen being non-viable, for the reasons explained. Therefore, banana plants can in general be seen to be parthenocarpic. Banana plants are commonly propagated asexually from side shoots or suckers at the base of the main stalk, which can be removed and replanted to continue the cultivar.

Growers also propagate bananas by means of tissue culture, in particular for producing disease free material.

Seedless cucumber, seedless squash and seedless eggplant are examples for crops which can produce seedless fruits without pollination (parthenocarpy), e.g. under conditions where pollination is impaired (e.g. low temperatures). Nevertheless, commercial quality fruit can be produced under these conditions. All these crops however can produce seed bearing fruits upon pollination. Therefore, these crops are facultative parthenocarpic. Propagation of the crops can be done by self- or cross pollination, in vitro propagation, and grafting.

From tomato mutants it is also known that they can produce seedless fruits under conditions where normal pollination/fertilization is impaired (e.g. under circumstances of low temperature). Thus, these mutants are also facultative parthenocarpic. Mutants known for showing this phenotype are pat, pat-2 and the pat-3/pat-4 system. The genes underlying these mutations are not known and the pat-3/pat-4 system seems to depend on multiple loci.

Parthenocarpy has also been introduced into several plant species by means of genetic modification. Expression of a bacterial tryptophan monooxygenase (iaaM) conferring auxin synthesis under control of the ovule and placenta specific DefH9 promoter did induce parthenocarpy in cucumbers (Yin et al., 2006, Clular & molecular Biotech. Letters 11, 279-290), eggplant (Acciarri et al., 2002, BMC Biotech. 2(4)), tomato (Rotino et al., 2005, BMC Biotech. 5(32)) and tobacco.

These transgenic plants demonstrate the importance of plant hormones in seed and fruit development. That seed and fruit development are besides other factors strongly under control of several plant hormones is well known in the art. Parthenocarpy, including the logical consequence of fruit's seedlessness, can also be induced e.g. by exogenous application of plant hormones, in particular auxin or gibberellin (Ruan et al., Trends in Plant Sci. 17(11), 1360-1385).

Seedless watermelons produced by breeders are examples for stenospermocarp crops. Normal watermelon plants are diploid (2n). Seedless fruit producing watermelons are hybrids produced by crossing a male diploid (2n) watermelon plant with a female tetraploid (4n) watermelon plant. The resulting F1 hybrid seeds are triploid (3n). Induction of fruit setting in the F1 hybrid plants requires pollination. As the triploid (3n) F1 hybrid plants do not produce fertile pollen, so called pollinator or polliniser plants have to be planted in the same field. The pollinator plants are diploid (2n). Generally a ratio of pollinator to hybrid plants of around 1 to 3 must be planted in a given scheme for providing sufficient pollen for pollinating all the F1 hybrid plants. The cross-pollination between the diploid (2n) pollinator and the flowers of the female triploid (3n) hybrid plant induces fruit set and leads to the production of seedless triploid fruits on the triploid hybrid plant. The diploid (2n) and tetraploid (4n) parents of the F1 hybrid each produce seed bearing fruits and can both be propagated independently from each other by self-pollination.

Seedless grapes can be produced from plants being either parthenocarp or stenospermocarp. The variety Black Corinth is parthenocarp, whereas Sultanina is stenospermocarp. Vine plants are in general propagated by cuttings and successive grafting to another rootstock.

Irregularities in meiosis can be a factor leading to plants producing seedless fruit. An example for plants producing seedless fruits is given in Zhang et al. (2012, Scientia Horticulture 140, 107-114), disclosing seedless watermelons. A male and female sterile (MFS) mutant was obtained from the progeny of a F1-hybrid after irradiation of its seeds with gamma-rays. Pollen from the MFS mutant was not viable at all. Seedless fruits are produced by the MFS plants, when pollinated with pollen from male fertile plants. The MFS watermelon plant therefore can be classified as being stenospermocarpic. Ovules were also nearly entirely non-viable, as almost no seeds were produced upon cross-pollination of MFS mutants with pollen from different male fertile plants. Incomplete synapsis and abnormal separation of chromatids during meiosis were observed in the MFS mutant and seen to be the cause of male and female sterility. The genes responsible for the effects present in the MFS mutant have not been identified but it seems likely that the phenotype in the MFS mutant is due to a single recessive gene.

Pradillo et al. (2014, Frontiers in Plant Sci. 5, Article 23, do: 10.3389/fpls.2014.00023) reviews the knowledge in the art about genes which are involved in homologous recombination during meiosis in *Arabidospsis*.

Azumi et al. (2002, EMBO J. 21(12), 3081-3095) describe the isolation of an *Arabidopsis* mutant having defects in synapsis and bivalent formation in male meiosis and similar defects, although to a lesser extent, in female meiosis. The mutation was designated "Solo Dancers" (sds) and shown to originate from a single recessive gene. SDS mutants are male sterile and strongly impaired in female fertility. Plants homozygous for the sds mutation are male sterile but at least to a minor extend female fertile, which was demonstrated by cross-pollination of the sds mutant plant with pollen from male fertile plants. SDS mutants therefore are male sterile and strongly impaired in female fertility. The sds gene was identified to belong to the cyclin type protein encoding genes and has been demonstrated to interact with *Arabidopsis* CDKs, Cdc2a and Ccdc2b proteins. SDS however has been identified to be a new, beforehand unknown cyclin type protein. De Muyt et al. (2009, PLOS genet. 5(9) e1000654, doi: 10.1371/journal.pgen.1000654) confirms that the sds *Arabidopsis* mutant has a recombination defect in meiosis and suggest that the defect is caused by a misallocation of another protein (AtDMC1) in the cells during meiosis.

From above discussion it is evident, that the factors determining if plants produce seedless fruits are multiple in nature and can reside in several, e.g. morphologic, physiologic and/or genetic causes.

For producing seedless fruits in stenospermocarpic crops, a female flower part of a plant must be pollinated. The stenospermocarpic crops grown today are male sterile. As a consequence, besides the female plant, a different male fertile plant (pollinator or polliniser) has to be grown in addition in the same field. As the area used for the pollinator plants is at the expense of the area which is available for the seedless fruit producing female plants, the yield per area under cultivation is reduced. In general, the pollinator plants are normal plants which can also be self-pollinated. Fruits produced by pollinator plants however do produce seeds. In watermelon, the pollinator plants are normally diploid (2n), which upon self-pollination produce seeded fruits, which may in some instances also be harvested and sold separately (see WO2012069539). For commercial reasons these seeded fruits from the pollinator plants must not be mixed with the seedless fruits. Therefore, it has to be ensured, that seedless fruits and seeded fruits are separated upon or after harvest, which may make machine harvesting difficult or impossible or require a further processing step after harvesting. Those additional precautions to be taken increase the input costs in seedless fruit production. In addition, pollinator plants are developed so that they flower and produce sufficient viable pollen at the same time the female plant flowers and its stigma can accept pollen for the induction of fruit set. Thus, the pollinator plant has to fit with the female plant producing seedless fruit in respect to flowering and fertilisation time. If flowering time of the pollinator pant and the respective female plant is not sufficiently synchronised, pollination will not take place or only take place in an unsufficient amount of cases. As a result fewer fruits are produced by the stenospermocarpic female plant. Furthermore, it is well known in the art that climate conditions, like rain, heat etc., may influence pollen production of a polliniser plant differently than stigma fertility time of the genotypic different female plant. Therefore, climate conditions can also lead to asynchrony of fertility time of pollinator and female plant with the effect of lowering the yield.

Respective disadvantages are not applicable to the plants of the invention described herein below.

It is, therefore, an object of the invention to overcome the disadvantages of seedless fruit producing plants currently cultivated.

In a population of mutagenized M2 diploid watermelon plants a plant producing seedless fruits was observed. The mutant plant was designated EMB1. Surprisingly, pollen of said plant could be used to make back-crosses. Thus, contrary to the seedless fruit producing plants known in the art, the plants disclosed herein are male fertile. The back-crosses were self-pollinated and 25% of the plants obtained therefrom produced seedless fruits. A mutant allele (emb1) was identified which caused the seedless fruit phenotype, i.e. when diploid plants homozygous for emb1 (emb1/emb1) were either self-pollinated or pollinated by pollen from another plant, they produced seedless, diploid fruits. Thus, the seedless fruit phenotype occurs in plants being homozygous for a recessive mutation in the emb1 allele. The wild type protein encoded by the wild type allele corresponding to the mutant emb1 allele of the invention has some similarities but also significant differences with cyclin SDS proteins and was, therefore, designated "cyclin SDS like protein". The sequence identity between the cyclin SDS protein and its encoding nucleic acid sequences known in the art and the respective sequences of the cyclin SDS like proteins disclosed herein are low. Concerning the phenotypic effect in plants, the plants known in the art, having a mutation in a cyclin SDS protein, have a male sterile phenotype, whereas the plants disclosed herein, having a mutation in a cyclin SDS like protein, are male fertile.

A first embodiment of the present invention concerns plant cells, plant parts and plants, characterized in that the plant cells or plants have a decreased activity of a cyclin SDS like protein compared to the plant cells and plants comprising a functional wild type cyclin SDS like protein.

In context of the present invention, a "cyclin SDS like protein" shall be understood to mean a protein which, when its activity is decreased or its expression is entirely knocked-out in a plant, leads (e.g. in a plant homozygous for a mutant nucleotide sequence encoding a cyclin SDS like protein) to male fertile pollen produced by that plant but at the same time leads to the production of seedless fruits of said plant, when self-pollinated.

In context of the present invention, "decreased activity" of a protein shall mean a decrease in activity of a cyclin SDS like protein when compared to a corresponding wild type plant cell or a corresponding wild type plant. Decrease shall in one aspect comprise an entire knock-out of gene expression, or the production of a loss of function or of a decreased function cyclin SDS like protein, e.g. a truncated SDS like protein may have lost function or decreased function. A decrease in activity can be a decrease in the expression of a gene encoding a cyclin SDS like protein (also referred to as knock-down), or a knock-out of the expression of a gene encoding a cyclin SDS like protein and/or a decrease in the quantity of a cyclin SDS like protein in the cells or a decrease of function or loss of function in the enzymatic activity of a cyclin SDS like proteins in the cells.

"Knock-out" or "entire knock-out" shall be understood that expression of the respective gene is not detectable anymore.

"Loss of function (in the enzymatic activity)" shall mean in context of the present invention that the protein, although present in amounts equal or similar to a corresponding wild type protein, does not evoke its effect anymore, i.e. mutant alleles when present in homozygous form in a diploid plant, the plant is male fertile but produces only seedless fruits upon pollination. The terms "non-functional" and "lost activity" shall have the same meaning as "loss of function". All three terms are used herein interchangeably. Thus, when referring to a cyclin SDS like gene encoding a non-functional protein, the gene may be expressed, but the encoded protein is not functional, e.g. due to the protein being truncated or comprising one or more amino acid replacements, insertions or deletions compared to the wild SDS like protein.

"Decrease of function (in the enzymatic activity)" or "reduced function" shall mean in context of the present invention that the protein although present in amounts equal or similar to a corresponding wild type protein, does not evoke its effect anymore, i.e. when present in homozygous form in a diploid plant, the plant is male fertile but produces only seedless fruits upon pollination.

"Conserved domain" refer to conserved protein domains, such as the Cyclin_N (pfam00134) and Cyclin_C domains (pfam02984). These domains can e.g. be found in the Conserved Domain Database of the NCBI (world wide web at ncbi.nlm.nih.gov/cdd).

"M1 generation" or "M1 plants" in context with the present invention shall refer to the first generation that is produced directly from the mutagenic treatment. A plant grown from seeds treated with a mutagen e.g. is a representative of an M1 generation.

"M2 generation" or "M2 plant" shall refer herein to the generation obtained from self-pollination of the M1 generation. A plant grown from seeds obtained from a self-pollinated M1 plant represents a M2 plant.

The decrease in the expression can, for example, be determined by measuring the quantity of RNA transcripts encoding cyclin SDS like proteins, e.g. using Northern blot analysis or RT-PCR. Here, a reduction preferably means a reduction in the amount of transcripts by at least 50%, in particular by at least 70%, preferably by at least 85% and particularly preferably by at least 95%.

The decrease in the amount of a cyclin SDS like protein, which results in a reduced activity of these proteins in the plant cells or plants concerned, can, for example, be determined by immunological methods such as Western blot analysis, ELISA (Enzyme Linked Immuno Sorbent Assay) or RIA (Radio Immune Assay). Here, a decrease preferably means a reduction in the amount of cyclin SDS like proteins by at least 50%, in particular by at least 70%, preferably by at least 85% and particularly preferably by at least 95%.

Methods for the manufacture of antibodies that react specifically with a designated protein, i.e. that bind specifically to the said protein, are known to the person skilled in the art (see, for example, Lottspeich and Zorbas (Eds.), 1998, Bioanalytik, Spektrum akad, Verlag, Heidelberg, Berlin, ISBN 3-8274-0041-4). The manufacture of such antibodies is offered as a contractual service by several firms.

Concerning the present invention, a decrease of activity of a cyclin SDS like protein in a plant according to the invention can also be determined by the plant phenotype. Plants homozygous for a mutant allele encoding the cyclin SDS like protein or having a decreased activity of a cyclin SDS like protein, produce seedless fruits and are male fertile (produce viable pollen).

In one embodiment the decreased activity of a protein having a cyclin SDS like function is decreased in the plant cells or plants according to the invention compared to corresponding wild type plant cells or wild type plants.

In context with the present invention, the term "wild type plant cell" or "wild type plant" means that the plant cells or plants concerned were used as starting material for the production of the plant cells or plants according to the invention, i.e. their genetic information, apart from the introduced (genetic) modification(s) or mutation(s), corresponds to that of a plant cell or plant according to the invention. In one aspect the wild type plant or wild type plant cell is a plant comprising a fully functional cyclin SDS like protein, e.g. regarding watermelon plants or plant cells a diploid watermelon plant producing the protein of SEQ ID NO 2 and producing seeded fruits upon self-pollination. Or regarding melon plants or cells a diploid melon plant producing the protein of SEQ ID NO 6, or regarding cucumber plants or cells a diploid cucumber plant producing the protein of SEQ ID NO 12, or regarding tomato plants or cells a diploid tomato plant producing the protein of SEQ ID NO 19, or regarding pepper plants or cells a diploid plant producing the protein of SEQ ID NO: 20.

In conjunction with the present invention, the term "corresponding" means that, in the comparison of several objects, the objects concerned that are compared with one another have been kept under the same conditions. In conjunction with the present invention, the term "corresponding" in conjunction with wild type plant cell or wild type plant means that the plant cells or plants, which are compared with one another, have been raised under the same cultivation conditions, that they have the same (cultivation) age and that their genetic information, apart from the introduced (genetic) modification(s) or mutation(s), corresponds to that of a plant cell or plant according to the invention. In case nucleic acid sequences of RNA and DNA molecules are compared with each other or said to correspond to each other, it is well understood in the art that a thymine (T) in a DNA molecule is equivalent with uridine (U) in an RNA molecule. Thus, a T in a DNA sequence is to be understood to be replaced by a U in an RNA sequence and vice versa, when such molecules are compared with each other.

Preferably in the embodiments according to the invention, the cyclin SDS like protein of a wild type plant cell, plant part or wild type plant is encoded by nucleic acid molecules selected from the group consisting of:

a) nucleic acid molecules, which encode a protein with the amino acid sequence given under SEQ ID NO 2 (watermelon cyclin SDS like protein) or SEQ ID NO 6 (melon cyclin SDS like protein) or SEQ ID NO 12 (cucumber cyclin SDS like protein) or SEQ ID NO: 19 (*Solanum lycopersicum* cyclin SDS like protein) or SEQ ID NO: 20 (*Capsicum annuum* cyclin SDS like protein);

b) nucleic acid molecules, which encode a protein, the sequence of which has an identity of at least 58% or at least 60%, preferably at least 70%, more preferably at least 80%, even further preferred at least 90%, or particularly preferred at least 95% with the amino acid sequence given under SEQ ID NO 2 or SEQ ID NO 6 or SEQ ID NO 12 or SEQ ID NO: 19 or SEQ ID NO: 20;

c) nucleic acid molecules, which comprise the nucleotide sequence shown under SEQ ID NO 1 or SEQ ID NO 5 or SEQ ID NO 17 or a complimentary sequence thereof;

d) nucleic acid molecules, which have an identity of at least 58% or at least 60% preferably at least 70%, more preferably at least 80%, even further preferred at least 90% or particularly preferred at least 95% with the nucleotide sequences described under c);

e) nucleic acid molecules, which hybridise with at least one strand of the nucleic acid molecules described under a), b), c), or d) under stringent conditions;

f) nucleic acid molecules, the nucleotide sequence of which deviates from the sequence of the nucleic acid molecules identified under a), b), c) or d) due to the degeneration of the genetic code; and g) nucleic acid molecules, which represent fragments, allelic variants and/or derivatives of the nucleic acid molecules identified under a), b), c) or d).

The genomic nucleotide sequence shown under SEQ ID NO 1, and the coding sequence as indicated in SEQ ID NO 1, encodes a wild type cyclin SDS like protein of *Citrullus lanatus* (watermelon) having the amino acid sequence as shown under SEQ ID NO 2. SEQ ID NO 5 shows the coding sequence encoding a wild type cyclin SDS like protein from *Cucumis melo* (melon) having the amino acid sequence as shown under SEQ ID NO 6. SEQ ID NO 12 shows the wild type cyclin SDS like protein from *Cucumis sativus* (cucumber). SEQ ID NO: 19 shows the wild type cyclin SDS like protein of *Solanum lycopsersicum* (tomato). SEQ ID NO: 20 shows the wild type cyclin SDS like protein of *Capsicum annuum* (pepper).

The plant cells, plant parts or plants according to the invention can be plant cells from any species or plants of any species. The plant cells according to the invention can be monocotyledonous and dicotyledonous plant cells, the plants according to the invention can be monocotyledonous and dicotyledonous plants. Preferably the plant cells according to the invention are plant cells of vegetables (vegetable plant cells) or the plants are vegetable plants, in particular vegetables like tomato, onion, leek, garlic, carrots, pepper, asparagus, artichoke, celeriac, cucumber, melon, gourd, squash, lettuce, watermelon, spinach, cabbage (*Brassica oleracea*), corn salad, aubergine and okra. More preferred are plant cells from vegetables (vegetable plant cells) or vegetable plants from the Cucurbitaceae family or Solanaceae family. Most preferred plant cells and plants according to the invention comprise squash (*Cucurbita pepo, Cucurbtita maxima, Cucurbita moschata, Lagenaria siceraria*), melon (*Cucumis melo*), cucumber (*Cucumis sativus*), watermelon (*Citrullus lanatus*), tomato (*Solanum lycopersicum*) or pepper (*Capsicum annuum*) plant cells or plants, in particular preferred are plant cells from watermelon (*Citrullus lanatus*) or melon (*Cucumis melo*) or watermelon (*Citrullus lanatus*) or melon (*Cucumis melo*) plants. In one embodiment the plants and plant cells are cultivated plants of these species, such as inbred lines or varieties having good agronomic characteristics, especially producing marketable produce (e.g. fruits) of good quality and uniformity.

Another embodiment of the present invention concerns plants and plant parts comprising plant cells according to the invention.

A further embodiment of the present invention is a plant cell or plant, characterised in that the plant cell or plant has a decreased activity of a cyclin SDS like protein compared to a corresponding wild type plant cell or wild type plant, wherein the cyclin SDS like protein of a corresponding wild type plant cell or wild type plant is encoded by nucleic acid molecules selected from the group consisting of a) Nucleic acid molecules, which encode a protein with the amino acid sequence given under SEQ ID NO 2 (watermelon cyclin SDS like protein) or SEQ ID NO 6 (melon cyclin SDS like protein) or SEQ ID NO 12 (cucumber cyclin SDS like protein) or SEQ ID NO: 19 (*Solanum lycopersicum* cyclin SDS like protein) or SEQ ID NO: 20 (*Capsicum annuum* cyclin SDS like protein);

b) Nucleic acid molecules, which encode a protein, the sequence of which has an identity of at least 58% or at least 60%, preferably at least 70%, more preferably at least 80%, even further preferred at least 90% or particularly preferred at least 95% with the amino acid sequence given under SEQ ID NO 2 or SEQ ID NO 6 or SEQ ID NO 12 or SEQ ID NO 19 or SEQ ID NO 20;

c) Nucleic acid molecules, which comprise the nucleotide sequence shown under SEQ ID NO 1 or SEQ ID NO 5 or SEQ ID NO 17 or a complimentary sequence thereof;

d) Nucleic acid molecules, which have an identity of at least 58% or at least 60%, preferably at least 70%, more preferably at least 80%, even further preferred at least 90% or particularly preferred at least 95% with the nucleotide sequences described under c);

e) Nucleic acid molecules, which hybridise with at least one strand of the nucleic acid molecules described under a), b), c), or d) under stringent conditions;

f) Nucleic acid molecules, the nucleotide sequence of which deviates from the sequence of the nucleic acid molecules identified under a), b), c) or d) due to the degeneration of the genetic code; and g) Nucleic acid molecules, which represent fragments, allelic variants and/or derivatives of the nucleic acid molecules identified under a), b), c) or d).

"Sequence identity" and "sequence similarity" can be determined by alignment of two peptide or two nucleotide sequences using global or local alignment algorithms. Sequences may then be referred to as "substantially identical" or "substantial identity" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm for aligning two sequences, over their entire length, maximizing the number of matches and minimizing the number of gaps. Generally, the default parameters are used, with a gap creation penalty=10 and gap extension penalty=0.5 (both for nucleotide and protein alignments). For nucleotides the default scoring matrix used is DNA-FULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS, accessible at world wide web under ebi.ac.uk/Tools/emboss/. Alternatively sequence similarity or identity may be determined by searching against databases (e.g. EMBL, GenBank) by using commonly known algorithms and output formats such as FASTA, BLAST, etc., but hits should be retrieved and aligned pairwise to compare sequence identity. Two proteins or two protein domains, or two nucleic acid sequences have "substantial sequence identity" if the percentage sequence identity is at least 58%, 60%, 70%, 80%, 90%, 95%, 98%, 99% or more (as determined by Emboss "needle" using default parameters, i.e. gap creation penalty=10, gap extension penalty=0.5, using scoring matrix DNAFULL for nucleic acids an Blosum62 for proteins). Such sequences are also referred to as "variants" or "allelic variants" or "derivatives" herein. Other allelic variants of the cyclin SDS like protein encoding genes/alleles and cyclin SDS like proteins than the specific nucleic acid and protein sequences disclosed herein can be identified. So for example cyclin SDS like proteins having substantial sequence identity to the protein of SEQ ID NO: 2, or to the protein of SEQ ID NO: 6, or to the protein of SEQ ID NO: 12, or to the protein of SEQ ID NO: 18, or to the protein of SEQ ID NO: 19 are variants of the provided protein.

Allelic variants may exist in other cultivated vegetable plant cells or plants, in particular vegetables like tomato, onion, leek, garlic, carrots, pepper, asparagus, artichoke, gourd, squash, celeriac, cucumber, melon, lettuce, watermelon, spinach, cabbage (*Brassica*) species, corn salad and okra. Mutations in such allelic variants of the cyclin SDS like protein encoding gene have the same effect on male and female fertility and seedless fruit production in other vegetable plants. Particularly allelic variants of a cyclin SDS like gene may exist in plant cells or plants from the Cucurbitaceae family, like melon (*Cucumis melo*), cucumber (*Cucumis sativus*), watermelon (*Citrullus lanatus*), squash (*Cucurbita pepo, Cucurbtita maxima, Cucurbita moschata, Lagenaria siceraria*), particular preferred allelic variants of a cyclin SDS like gene may exist in plant cells of watermelon (*Citrullus lanatus*), melon (*Cucumis melo*) or cucumber (*Cucumis sativus*) or watermelon (*Citrullus lanatus*) or melon (*Cucumis melo*) or cucumber (*Cucumis sativus*) plants. Additionally allelic variants of a cyclin SDS like gene may also exist in plant cells or plants from the Solanaceae family, like tomato (*Solanum lycopersicum*) or wild relatives of tomato (*S. pimpinelli, S. cheesmaniae, S. galapagense, S. pimpinellifolium, S. chmielewskii, S. habrochaites, S. neorickii,* and *S. pennelli, S. arcanum, S. chilense, S. corneliomulleri, S. huaylasense,* and *S. peruvianum*), pepper (*Capsicum annuum*), *Solanum melongena* (aubergine), *Solanum tuberosum* (potato), etc.

Allelic variants may also exist in other cultivated crop plants, such as filed crops (e.g. *Brassica* species, maize, rice, soybean, wheat, barley, cotton, tobacco, coffee, etc.) or fruit crops (e.g. grape, apple, plum, citrus fruits, strawberry, etc.).

It is noted that the cyclin SDS like proteins of the Cucurbitaceae have a high sequence identity to each other (at least 70% for the provided sequences) and the cyclin SDS like proteins of the Solanaceae also have a high sequence identity to each other. On the other hand, the sequence identity between Cucurbitaceae and Solanaceae sequences it not high (40% or less), see Table A below.

TABLE A cyclin SDS like protein sequence identity (pairwise alignment using Needleman and Wunsch)

| | Watermelon (SEQ ID NO 2) | Melon (SEQ ID NO 6) | Cucumber (SEQ ID NO 12) | Tomato (SEQ ID NO 19) | Pepper (SEQ ID NO 20) |
|---|---|---|---|---|---|
| Watermelon (SEQ ID NO 2) | 100% | 73% | 70% | 34% | 32% |

TABLE A-continued cyclin SDS like protein sequence identity (pairwise alignment using Needleman and Wunsch)

| | Watermelon (SEQ ID NO 2) | Melon (SEQ ID NO 6) | Cucumber (SEQ ID NO 12) | Tomato (SEQ ID NO 19) | Pepper (SEQ ID NO 20) |
|---|---|---|---|---|---|
| Melon (SEQ ID NO 6) | | 100% | 86% | 40% | 38% |
| Cucumber (SEQ ID NO 12) | | | 100% | 40% | 37% |
| Tomato (SEQ ID NO 19) | | | | 100% | 81% |
| Pepper (SEQ ID NO 20) | | | | | 100% |

"Stringent hybridisation conditions" can be used to identify nucleotide sequences, which are substantially identical to a given nucleotide sequence. Stringent conditions are sequence dependent and will be different under different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridise to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually two) in 0.2×SSC at a temperature of at least 50° C., usually about 55° C., for 20 min, or equivalent conditions. See also Sambrook et al. (1989) and Sambrook and Russell (2001).

A decrease in the activity of a cyclin SDS like protein in plant cells or plants according to the invention can also be achieved by a gene silencing effect.

In a further embodiment of the invention the decreased activity of a cyclin SDS like protein in plant cells or plants according to the invention is caused by a gene silencing effect.

The plant cells according to the invention and plants according to the invention having a decreased activity of a cyclin SDS like protein can be produced by different methods causing a gene silencing effect known to the person skilled in the art. These include, for example, the expression of a corresponding antisense RNA or of a double-stranded RNA construct (RNAi technology), the provision of nucleic acid molecules or vectors, which impart a co-suppression effect, the expression of a correspondingly constructed ribozyme that splits specific transcripts, which code a cyclin SDS like protein.

The decrease of the cyclin SDS like protein activity in plant cells and plants according to the invention can be brought about by expressing an antisense sequence in respective plant cells or plants.

The decrease of the cyclin SDS like protein activity in plant cells and plants according to the invention can be brought about by the simultaneous expression of sense and antisense RNA molecules (RNAi technology) of the respective target gene to be repressed, preferably of the cyclin SDS like protein encoding gene or allele.

In addition to this, it is known that in planta the formation of double-stranded RNA molecules of promoter sequences can lead in trans to methylation and transcriptional inactivation of homologous copies of this promoter (Mette et al., EMBO J. 19, (2000), 5194-5201). The decrease of the cyclin SDS like protein activity in plant cells and plants according to the invention can be brought about by the simultaneous expression of sense and antisense RNA molecules (RNAi technology) of promoter sequences initiating transcription of the respective target gene to be repressed, preferably of the cyclin SDS like protein encoding gene or allele.

Ribozymes have also been described in the art to decrease the expression of proteins by cleaving RNA molecules encoding the target gene.

Additional discussion of the respective gene silencing technologies known to a person skilled in the art will be provided herein further below and are applicable to the plant cells or plants according to the invention accordingly.

"Gene silencing effect" refers to a down-regulation or complete inhibition of gene expression of the target gene or gene family. Silenced plant cells or plants produce lower amounts of translation eligible transcripts (including mRNA) for a respective target gene or allele, compared to corresponding wild type plant cells or corresponding wild type plants. The lower amounts of translation eligible transcripts (including mRNA) may be due to targeted degradation of respective transcripts.

A "target gene or allele" shall be understood to be the gene or allele or gene family (or one or more specific alleles of the gene) which has to be modulated for conferring an organism (e.g. plant cell or plant) to produce a desired phenotype. Concerning male sterile seedless fruit producing plants e.g. (a) target gene(s) or (a) target allele(s) is/are the cyclin SDS line protein encoding gene(s).

In a further embodiment of the invention the decreased activity of a cyclin SDS like protein in plant cells or plants according to the invention is caused by immunomodulation methods.

A further possible way in which to reduce the enzymatic activity of proteins in plant cells or plants is the so-called immunomodulation method. It is known that an in planta expression of antibodies, which specifically recognize a plant protein, results in a decrease of the activity of the proteins concerned. Additional discussion of the respective technology known to a person skilled in the art will be provided herein further below.

A further embodiment of the invention, are plant cells or plants characterised in that they comprise a mutant allele of a cyclin SDS like protein encoding gene. The mutant allele of a cyclin SDS like protein encoding gene can be present in homozygous or heterozygous state. In one aspect, the mutant allele encodes a cyclin SDS like protein having decreased function or loss of function of the encoded mutant protein. The mutant allele may encode a protein with one or more amino acids replaced, inserted or deleted, resulting in a protein having decreased function or loss of function compared to the wild type (functional) protein. In one aspect the mutant allele results in a truncated cyclin SDS like protein being produced, which truncated protein has decreased function or loss of function. In another aspect the mutant allele encodes a protein with one or more amino acids replaced, inserted or deleted in a conserved domain of the cyclin SDS like protein, such as the Cyclin_N domain (pfam00134) or the Cyclin_C domain (pfam02984). The Cyclin_N domain and Cyclin_C domain of a protein can be identified by the skilled person e.g. by a protein against protein BLAST on the website of the NCBI (world wide web at blast.ncbi.nlm.nih.gov) or by searching in the Conserved Domain Database of the NCBI (world wide web at ncbi.nlm-.nih.gov/cdd).

In SEQ ID NO: 2 the Cyclin_N domain ranges from amino acid 388 to amino acid 463 and the Cyclin_C domain ranges from amino acid 466 to 531.

A protein to protein BLAST provides the Cyclin_N and Cyclin_C domains of the search query used, including the alignment of the queried sequence with the domain. It is noted that "from" a certain number "to" another number includes the end points, i.e. includes the first and last number mentioned.

So for any of the protein sequences provided herein, or for other variant sequences (e.g. proteins comprising at least 70%, 80%, 90%, 95% or more sequence identity to any of the protein sequences provided herein, e.g. SEQ ID NO: 2, 6, 12, 19 or 20) the Cyclin_N and Cyclin_C domains can be determined.

In SEQ ID NO 6 the Cyclin_N domain ranges from amino acid 351 to amino acid 481 and the Cyclin_C domain ranges from amino acid 486 to amino acid 577.

In SEQ ID NO: 12 the Cyclin_N domain ranges from amino acid 343 to amino acid 473 and the Cyclin_C domain ranges from amino acid 478 to amino acid 569.

In SEQ ID NO: 19 the Cyclin_N domain ranges from amino acid 362 to amino acid 494 and the Cyclin_C domain ranges from amino acid 499 to 584.

In SEQ ID NO: 20 the Cyclin_N domain ranges from amino acid 332 to amino acid 464 and the Cyclin_C domain ranges from amino acid 469 to 554.

Plants in which the mutant allele of a cyclin SDS like protein encoding gene is present in a heterozygous state, will produce seeds and are male fertile. Thus, those plants can be used to introduce the mutant allele of a cyclin SDS like protein encoding gene into other plants or they can be used to introduce further traits into the plant in which the mutant allele of a cyclin SDS like protein encoding gene is present. These plants can also be used to propagate plants comprising a mutant allele of a cyclin SDS like encoding gene. 50% of the self-pollinated offspring in each case will still carry the mutant allele of a cyclin SDS like protein encoding gene in a heterozygous state. Therefore, plants in which the mutant allele of a cyclin SDS like protein encoding gene is present are useful e.g. in breeding.

Therefore, one embodiment of the invention concerns plant cells or plants according to the invention which are heterozygous for a mutant allele of a cyclin SDS like protein encoding gene.

In a preferred embodiment of the invention, the decreased activity of a cyclin SDS like protein in plant cells or plants according to the invention is due to or caused by or is the effect of a mutant allele of a cyclin SDS like protein encoding gene being present in plant cells or plants, respectively.

In one aspect, the plant cells or plants according to the invention are homozygous for the mutant allele of a cyclin SDS like protein encoding gene encoding a decrease of function of a cyclin SDS like protein or a loss of function of a cyclin SDS like protein. Plants according to the invention being homozygous for a mutant allele of a cyclin SDS like protein encoding gene produce seedless fruits upon pollination with own pollen or pollen obtained from a different plant (e.g. from a wild type plant).

Another embodiment of the invention therefore concerns plant cells or plants according to the invention which are homozygous for a mutant allele of a cyclin SDS like protein encoding gene.

A mutant allele of a cyclin SDS like protein encoding gene causes a plant to be male fertile but producing seedless fruits, when the plant is homozygous for the mutant allele. Concerning the embodiments of the invention, the mutation in the mutant allele of a cyclin SDS like protein encoding gene can be any mutation, including deletions, truncations, insertions, point mutations, nonsense mutations, missense or non-synonymous mutations, splice-site mutations, frame shift mutations and/or mutations in regulatory sequences. Preferably the mutation in the mutant allele of a cyclin SDS like protein encoding gene is a point mutation and/or splice-site mutation. The mutation can occur in a DNA sequence comprising the coding sequence of a cyclin SDS like protein encoding gene or in a RNA sequence encoding a cyclin SDS like protein or it can occur in the amino acid of a cyclin SDS like protein. Concerning a DNA sequence of a cyclin SDS like protein encoding gene the mutation can occur in the coding sequence (cds, composed of the exons) or it can occur in non-coding sequences like 5'- and 3'-untranslated regions, introns, promoters, enhancers etc. of a cyclin SDS like protein encoding gene. In respect to RNA encoding a cyclin SDS like protein the mutation can occur in the pre-mRNA or the mRNA. In one aspect the mutant allele results in the protein having a loss of function or decrease of function due to one or more amino acids being replaced, inserted and/or deleted, for example resulting in one or more amino acids being replaced, inserted or deleted in the conserved Cyclin_N and/or Cyclin_C domain. For example, truncation of the protein to cause deletion of the Cyclin_C domain, or part thereof, or the Cyclin_N domain and the Cyclin_C domain or part of the Cyclin_N domain and the Cyclin_C domain will result in a loss of function or decrease of function of the protein.

A further embodiment of the invention therefore concerns plant cells or plants according to the invention comprising a mutant allele of a cyclin SDS like protein encoding gene characterized in that the mutant allele comprises or effects one or more of the mutations selected from the group consisting of a) a deletion, truncation, insertion, point mutation, non-sense mutation, missense or non-synonymous muta-tion, splice-site mutation, frame shift mutation in the genomic sequence;

b) a mutation in one or more regulatory sequences;

c) a deletion, truncation, insertion, point mutation, non-sense mutation, missense or non-synonymous muta-tion, splice-site mutation, frame shift mutation in the coding sequence;

d) a deletion, truncation, insertion, point mutation, non-sense mutation, missense or non-synonymous muta-tion, splice-site mutation, frame shift mutation in the pre-mRNA or mRNA; and/or e) a deletion, truncation, insertion or replacement of one or more amino acids in the cyclin SDS like protein.

Compared to SEQ ID NO 1, one of the mutant alleles of a cyclin SDS like protein encoding gene disclosed herein as one embodiment (present in the EMB1 mutant watermelon plant), has a point mutation (replacement of G by A) at nucleotide position 2185 in SEQ ID NO 1. mRNA tran-scribed from the disclosed mutant allele of a cyclin SDS like protein encoding gene is shown under SEQ ID NO 3. Corresponding nucleotides at position 2186 to 2201 of the wild type allele of the cyclin SDS like protein encoding gene shown under SEQ ID NO 1 are not present in the mRNA shown under SEQ ID NO 3. Thus, the point mutation found in the mutant allele of the cyclin SDS like protein encoding gene causes a deletion of 16 nucleotides in mRNA tran-scribed from the mutant allele compared to the mRNA transcribed from the corresponding wild type allele. The deletion in mRNA transcribed from the mutant allele is explained by mutation of a splice site resulting in alternative splicing of the respective mRNA. In addition, the deletion of 16 nucleotides in the mRNA transcribed from the disclosed mutant allele of the cyclin SDS like protein encoding gene causes a frame shift in the reading frame of the mRNA transcribed from the mutant allele compared to mRNA transcribed from the corresponding wild type allele. The protein translated from the wild type allele of the cyclin SDS like protein encoding gene is shown under SEQ ID NO 2. The protein translated from the mutant allele of the cyclin SDS like protein encoding gene is shown under SEQ ID NO 4. The corresponding nucleotide sequence encoding amino acids 358 to 363 (Ile-Leu-Arg-Phe-Glu-Glu) in SEQ ID NO 2 is not present in SEQ ID NO 4 and due to the frame shift in the reading frame the rest of the amino acid sequence is different and amino acids 364 to 562 in SEQ ID NO 2 are replaced by the 8 aberrant amino acids Asn-Trp-Thr-Met-Lys-Lys-Pro-Ile in SEQ ID NO 4 (i.e. amino acids 358 to 365 of SEQ ID NO 4). The mutant cyclin SDS like protein is much shorter, only 365 amino acids, compared to the wild type protein of 562 amino acids. Thus, the amino acid sequence of the mutant cyclin SDS like protein as shown under SEQ ID NO 4 comprises amino acid deletions and amino acid replacements compared the wild type cyclin SDS like protein shown under SEQ ID NO 2. Furthermore, the frame shift in the reading frame of the mRNA transcribed from the mutant allele of a SDS like protein encoding gene causes a non-sense mutation creating a pre-mature stop codon (nucleotides 1096 to 1098 in SEQ ID NO 3), leading to the amino acid sequence encoded by the mutant allele being truncated by 197 amino acids at the C-terminus when compared to the corresponding amino acid sequence encoded by the wild type allele shown under SEQ ID NO 2. Thus, compared to the wild type protein, the 205 amino acids of the wild type C-terminus are replaced by 8 different (aberrant) amino acids at the C-terminal end due to the frame shift, resulting in a mutant protein that is 197 amino acids shorter than the wild type protein. The mutant protein is, therefore, truncated compared to the wild type protein, as 205 amino acids of the wild type C-terminus are missing in the mutant protein. Of the wild type protein only the amino acids of exon 1 (amino acids 1 to 357 of SEQ ID NO: 2) are still present in the mutant protein. This means that also the conserved protein domains Cyclin_N and Cyclin_C are not present, meaning that the mutant protein has no function (i.e. is the mutant allele is a loss of function allele) or a decrease of function.

In summary, specifically disclosed herein for exemplify-ing the application is in one aspect a nucleic acid sequence of a mutant allele of a cyclin SDS like protein encoding gene which has a point mutation (nucleotide replacement) com-pared to the nucleic acid sequence of the corresponding wild type cyclin SDS like protein encoding gene. The point mutation in the mutant allele of the cyclin SDS like protein encoding gene causes a splice-site mutation leading to alternative splicing of the respective pre-mRNA. The alter-native splicing causes a frame shift in the open reading frame of the mRNA transcribed from the mutant allele of the cyclin SDS like protein encoding gene. The frame shift in the open reading frame of the mRNA transcribed from the mutant allele of the cyclin SDS like protein encoding gene causes deletion of nucleotides, replacement of nucleotides (missense or non-synonymous mutations) and the creation of a non-sense mutation creating a pre-mature stop codon in the mRNA transcribed from the mutant allele of the cyclin SDS like protein encoding gene compared to the mRNA transcribed from the corresponding wild type cyclin SDS like protein encoding gene. The respective amino acid sequence of the protein translated from the mRNA transcribed from the mutant cyclin SDS like protein encoding gene shows deletion of amino acids, replacement of amino acids and truncation of the amino acid sequence at the C-terminus compared to the amino acid sequence translated from the mRNA transcribed from the corresponding wild type cyclin SDS like protein encoding gene. As the point mutation is in the first intron, the amino acids encoded by exon 2, exon 3 and exon 4 of the wild type cyclin SDS like protein are missing in the mutant, i.e. only the amino acids encoded by exon 1 of the wild type SDS like protein are present in the mutant protein.

In watermelon exon 1 of the cyclin SDS like protein encodes amino acids 1 to 357 of SEQ ID NO 2; in melon exon 1 of the cyclin SDS like protein encodes amino acids 1 to 338 in SEQ ID NO: 6; in cucumber exon 1 of the cyclin SDS like protein encodes amino acids 1 to 330 in SEQ ID NO: 12; in tomato exon 1 of the cyclin SDS like protein encodes amino acids 1 to 350 in SEQ ID NO 19; in pepper exon 1 of the cyclin SDS like protein encodes amino acids 1 to 320 in SEQ ID NO 20.

In addition to the watermelon EMB1 mutant plant described herein above (and in the examples), another watermelon plant, comprising a different mutation in the cyclin SDS like protein encoding gene, has been generated by mutagenesis. The mutant comprises a C (Cytosine) to T (Thymine) nucleotide substitution at nucleotide 1687 of SEQ ID NO: 1, leading to the codon 'cag' (encoding the amino acid glutamine, amino acid 224 of the wild type protein) being changed into 'tag', which is a stop codon. The mutant cDNA is shown in SEQ ID NO 17 and the truncated protein, comprising only part of the amino acids encoded by exon 1 (i.e. only amino acids 1 to 223 instead of amino acids 1 to 357), is shown in SEQ ID NO 18. Like in the EMB1 mutant plant, the two conserved domains, the Cyclin_N and Cyclin_C domains, are missing in the mutant protein. Also this mutant results in a loss of function of the cyclin SDS like protein (or at least in a decreased of function).

In one aspect of the invention the mutant allele of a cyclin SDS like protein encoding gene has a mutation leading to one or more or all of the amino acids encoding the Cyclin_N and/or Cyclin_C domain being deleted or being replaced by different amino acids than in the wild type. In one aspect the mutant allele results in a truncated protein lacking all or part of the Cyclin_N and/or all or part of the Cyclin_C domain. For example, the mutant allele contains a mutation leading to a premature stop codon, whereby all or part of the Cyclin_N and/or all or part of the Cyclin_C domain are not present anymore in the resulting protein.

In one aspect the mutant allele is a mutant allele of the watermelon cyclin SDS like gene of SEQ ID NO: 1 and leads to the protein of SEQ ID NO: 4 or to the protein of SEQ ID NO: 18.

In one aspect of the invention the mutant allele of a cyclin SDS like protein encoding gene has a mutation leading to the amino acids encoding exons 2, 3 and/or 4 of the wild type protein being absent. Thus in one aspect the mutant allele encodes a truncated cyclin SDS like protein/or a protein comprising a deletion, which lacks the amino acids encoded by exons 2, 3 and/or 4 of the wild type protein, i.e. it lacks amino acids 358 to 413 of SEQ ID NO 2 (exon 2) or amino acids 339 to 394 of SEQ ID NO: 6 (exon 2), amino acids 331 to 386 of SEQ ID NO 12 (exon 2), amino acids 351 to 407 of SEQ ID NO 19 (exon 2), amino acids 321 to 377 of SEQ ID NO: 20 (exon 2), and/or amino acids 414 to 469 of SEQ ID NO 2 (exon 3) or amino acids 395 to 493 of SEQ ID NO 6 (exon 3) or amino acids 387 to 485 of SEQ ID NO 12, amino acids 408 to 506 of SEQ ID NO 19 (exon 3), amino acids 378 to 476 of SEQ ID NO 20 (exon 3), and/or amino acids 470 to 562 of SEQ ID NO 2 (exon 4) or amino acids 494 to 577 of SEQ ID NO: 6 (exon 4) or amino acids 486 to 569 of SEQ ID NO 12 (exon 4), amino acids 507 to 590 of SEQ ID NO 19 (exon 4), amino acids 477 to 560 of SEQ ID NO 20 (exon 4). Optionally the mutant allele encodes a truncated cyclin SDS like protein/or a protein comprising a deletion, which further lacks all or part of the amino acids encoding exon 1, i.e. amino acids 1 to 357 of SEQ ID NO 2 or amino acids 1 to 338 in SEQ ID NO: 6 or amino acids 1 to 330 in SEQ ID NO 12 or amin acids 1 to 350 of SEQ ID NO 19, or amino acids 1 to 320 of SEQ ID NO 20. For corresponding amino acid regions encoded by exons 1, 2, 3 and 4 of other cyclin SDS like proteins, e.g. of orthologs from other species, can be identified by pairwise alignment of the genomic DNA or the amino acid sequences. It is noted that only for SEQ ID NO 2 the exons were determined to be real exons (separated by introns on the genomic DNA), while for the other sequences the exons were determined by alignment and may not be the real exons, but are the rather the amino acids corresponding to the exons of SEQ ID NO 2 and can therefore also be simply referred to as amino acid regions of the protein.

In a preferred embodiment of the invention the mutant allele of a cyclin SDS like protein encoding gene has, or results in, a mutation at the 5'-end of its coding sequence (encoding the N-terminus of the protein). More preferred the mutant allele of a cyclin SDS like protein encoding gene has, or results in, a point mutation and/or a truncation at the 5'-end of its coding sequence. It is well known in the art that a mutation in the start codon (ATG) of a gene will have the effect that the respective gene is not translated into a respective full-length protein. For translation the next possible start codon (ATG) may be used, but this will lead to a truncation of the amino acid sequence of the protein at the N-terminus, in case the next ATG appears in the same reading frame or to the production of a protein having a different amino acid sequence. In both cases, the respective mutation at the 5'-end will lead to the production of a protein having decreased or lost enzymatic activity. In a preferred embodiment of the invention, the mutant allele of a cyclin SDS like protein encoding gene has a mutation in the start codon. The mutation in the start codon can be a point mutation in any of its three nucleotides or a deletion/truncation of at least the first, at least the first and the second or at least all three nucleotides of the start codon.

Further preferred embodiments of the invention are mutant alleles of a cyclin SDS like protein encoding gene which results in a deletion at the 3'-end of its coding sequence (encoding the C-terminus of the protein). As the conserved Cyclin_C domain is present at the C-terminus of the protein, a truncation which results in part of the Cyclin_C domain being absent (e.g. 1, 2, 3, 4, 5 or more amino acids of the Cyclin_C domain or even all of the Cyclin_C domain) will result in the protein having reduced function or no function. A longer truncation at the C-terminus, will even result in part or all of the Cyclin_N domain being deleted, which will likewise result in the protein having reduced or no function. There are only five amino acids between the Cyclin_C and Cyclin_N domain. A truncation of about 90 or more amino acids of the C-terminus results in most of the cyclin SDS like proteins missing the Cyclin_C domain and longer truncations of 95, 100, 110 or more amino acids will result in the Cyclin_N domain being deleted at least partially. As mentioned before, such truncations are encompassed herein, as leading to a protein of reduced function or no function. As mentioned previously, to test whether the protein has reduced function or no function, the mutant plant being homozygous for the mutant allele can be tested phenotypically to see if the expected phenotype occurs.

Preferably the mutant alleles of a cyclin SDS like protein encoding gene results in a truncation of at least 10, 20, 30, 40 or 50 nucleotides, preferably at least 100 nucleotides, more preferred of at least 200 nucleotides, even more preferred of at least 300 nucleotides, further preferred of at least 400 nucleotides and most preferred of at least 500 nucleotides, in particular preferred of at least 615 nucleotides at the 3'end of the protein coding sequence. A truncation by 591 nucleotides from a coding sequence translates into a truncation by 197 amino acids for the respective protein sequence. A preferred example for a cyclin SDS like protein having a truncation by 197 amino acids compared to the amino acid sequence of a corresponding wild type cyclin SDS like protein (SEQ ID NO 2) is shown under SEQ ID NO 4. Another example is a truncation of 339 amino acids (i.e. 1017 nucleotides of the coding region) compared to the corresponding wild type SDS like protein (SEQ ID NO 2) is shown in SEQ ID NO 18.

In one embodiment, the mutant allele of a cyclin SDS like protein encoding gene has any of the mutations mentioned above in a nucleic acid sequence encoding the protein of SEQ ID NO: 2 (resulting in the encoded protein comprising a deletion or truncation compared to the wild type), or in any nucleic acid sequence encoding a protein comprising at least 70%, 80%, 90%, 95% or more amino acid sequence identity to SEQ ID NO 2, such as for example SEQ ID NO 6, which has 71% sequence identity to SEQ ID NO 2.

In another embodiment, the mutant allele of a cyclin SDS like protein encoding gene has any of the mutations mentioned above in a nucleic acid sequence encoding the protein of SEQ ID NO: 6 (resulting in the encoded protein comprising a deletion or truncation compared to the wild type), or in any nucleic acid sequence encoding a protein comprising at least 70%, 80%, 90%, 95% or more amino acid sequence identity to SEQ ID NO 6.

In another embodiment, the mutant allele of a cyclin SDS like protein encoding gene has any of the mutations mentioned above in a nucleic acid sequence encoding the protein of SEQ ID NO: 12 (resulting in the encoded protein comprising a deletion or truncation compared to the wild type), or in any nucleic acid sequence encoding a protein comprising at least 70%, 80%, 90%, 95% or more amino acid sequence identity to SEQ ID NO: 12.

In another embodiment, the mutant allele of a cyclin SDS like protein encoding gene has any of the mutations mentioned above in a nucleic acid sequence encoding the protein of SEQ ID NO: 19 (resulting in the encoded protein comprising a deletion or truncation compared to the wild type), or in any nucleic acid sequence encoding a protein comprising at least 70%, 80%, 90%, 95% or more amino acid sequence identity to SEQ ID NO: 19.

In another embodiment, the mutant allele of a cyclin SDS like protein encoding gene has any of the mutations mentioned above in a nucleic acid sequence encoding the protein of SEQ ID NO: 20 (resulting in the encoded protein comprising a deletion or truncation compared to the wild type), or in any nucleic acid sequence encoding a protein comprising at least 70%, 80%, 90%, 95% or more amino acid sequence identity to SEQ ID NO: 20.

In a further preferred embodiment, the mutant allele of a cyclin SDS like protein encoding gene has any of the mutations mentioned above in the nucleic acid sequence shown under SEQ ID NO 1 or in a sequence having an identity of at least 58% or 60%, preferably at least 70%, more preferably at least 80%, even further preferred at least 90% or particularly preferred at least 95% with the nucleic acid sequence shown under SEQ ID NO 1. In one aspect a mutant allele of a cyclin SDS like protein encoding gene comprises a mutation in the nucleic acid sequence shown under SEQ ID NO 1 or in a variant sequence having an identity of at least 58% or 60%, preferably at least 70%, more preferably 80%, even further preferred 90% or particularly preferred 95% with the nucleic acid sequence shown under SEQ ID NO 1 wherein the nucleotide guanine (G) at nucleotide position number 2185 in SEQ ID NO 1 is replaced by adenine (A), cytosine (C) or thymine (T), most preferably the nucleotide guanine (G) at nucleotide position number 2185 in SEQ ID NO 1, or the equivalent nucleotide in a variant sequence, is replaced by adenine (A). Most preferably, the mutant allele of a cyclin SDS like protein encoding gene has the nucleotide acid sequence shown under SEQ NO 1 apart from that the nucleotide guanine (G) at nucleotide position number 2185 in SEQ ID NO 1 is replaced by adenine (A), cytosine (C) or thymine (T), most particularly preferred the nucleotide guanine (G) at nucleotide position number 2185 in SEQ ID NO 1 is replaced by adenine (A). In a different aspect a mutant allele of a cyclin SDS like protein encoding gene comprises a mutation in the nucleic acid sequence shown under SEQ ID NO 1 or in a variant sequence having an identity of at least 58% or 60%, preferably at least 70%, more preferably 80%, even further preferred 90% or particularly preferred 95% with the nucleic acid sequence shown under SEQ ID NO 1 wherein in the mutant allele of a SDS like protein encoding gene the nucleotide cytosine (C) at nucleotide 1687, or the equivalent nucleotide in a variant sequence, is replaced by a different nucleotide, preferably by thymine (T).

A different embodiment of the invention concerns plant cells, plant parts or plants comprising or synthesising an mRNA encoding a cyclin SDS like protein, wherein the mRNA encoding a cyclin SDS like protein has one or more mutations selected from the group consisting of a) a deletion mutation b) a missense or non-synonymous mutation;

c) a frame shift mutation; and/or d) a non-sense mutation.

In a preferred embodiment of the invention, plant cells, plant parts or plants according to the invention comprise or synthesise an mRNA encoding a cyclin SDS like protein having one or more of the mutations selected from the group consisting of a) a deletion mutation b) a missense or non-synonymous mutation;

c) a frame shift mutation; and/or d) a non-sense mutation.

Concerning deletions and replacements of one or more nucleotides, plant cells or plants according to the invention preferably comprise or synthesise an mRNA encoding a cyclin SDS like protein, wherein the mRNA comprises a deletion of at least 1, at least 2, at least 4, at least 5, at least 7, at least 8, at least 10, at least 11, at least 13, at least 14 or preferably at least 16 nucleotides compared to mRNA encoding a wild type cyclin SDS like protein. In one aspect the nucleotides(s) deleted in the mRNA are one or more nucleotides of exon 1, exon 2, exon 3 and/or exon 4 of the cyclin SDS like protein and/or the nucleotide(s) deleted in the mRNA are one or more nucleotides of the Cyclin_N or Cyclin_C domain of the cyclin SDS like protein. In one aspect the nucleotides are nucleotides of exon 2, e.g. one or more or all nucleotides starting at nucleotide 2186 and ending at nucleotide 2201 of SEQ ID NO 1.

Preferably, plant cells or plants according to the invention comprise or synthesise an mRNA encoding a cyclin SDS like protein, characterized in that the mRNA comprises a frame shift mutation and/or a non-sense mutation. The non-sense mutation creates a pre-mature stop codon and thus a truncation of the mRNA coding sequence. A preferred embodiment of the invention concerns plant cells or plants according to the invention comprising an mRNA encoding a cyclin SDS like protein, characterized in that the mRNA comprises a truncation of the coding sequence. The truncation of the mRNA coding sequence of a cyclin SDS like protein preferably is a truncation of at least 100 nucleotides, preferred of at least 200 nucleotides, more preferred of at least 300 nucleotides, even more preferred of at least 400 nucleotides and further more preferred of at least 500 nucleotides, in particular preferred of at least 591 nucleotides compared to mRNA encoding a wild type cyclin SDS like protein. In one aspect the truncation of the mRNA coding sequence results in exon 2, 3 and 4 to be absent; or exon 3 and 4 to be absent; or exon 4 to be absent. In another aspect the truncation of the mRNA coding sequence results in all or part of exon 1, all of exon 2, all of exon 3 and all of exon 4 to be absent. In another aspect, the frame-shift mutation results in all or part of exon 2 to be in a different reading frame. In a different aspect the frame-shift mutation results in all or part of exon 3 and/or exon 4 to be in a different reading frame. The frame shift may be caused by the deletion of one or more nucleotides (any number which is not a multitude of three, such as 1, 2, 4, 5, 7, 8, 10, etc.), whereby the reading frame is changed.

In a preferred embodiment, the plant cells, plant parts or plants according to the invention comprise or synthesise an mRNA encoding a cyclin SDS like protein which mRNA has at least 58% or at least 60%, preferably at least 70%, more preferably at least 80%, even further preferred at least 90% or particularly preferred at least 95% sequence identity with the corresponding coding sequence indicated in SEQ ID NO 1 or SEQ ID NO 5 or SEQ ID NO 17 with the prerequisite that the mRNA encoding a cyclin SDS like protein comprises a non-sense mutation or a pre-mature stop codon. In one embodiment the stop codon is in exon 1 of SEQ ID NO: 1, e.g. at nucleotides 1687 to 1689. In a further preferred embodiment, the plant cells, plant parts or plants according to the invention comprise or synthesise an mRNA encoding a cyclin SDS like protein which mRNA has at least 58% or 60%, preferably at least 70%, more preferably at least 80%, even further preferred at least 90% or particularly preferred at least 95% sequence identity with the coding sequence indicated in SEQ ID NO 3, with the prerequisite that nucleotides 1096 to 1098 in SEQ ID NO 3 represent a stop codon. In the most preferred embodiment of the invention, plant cells or plants according to the invention comprise or synthesise an mRNA encoding a cyclin SDS like protein which mRNA has the sequence shown under SEQ ID NO 3.

In another embodiment of the invention, plant cells or plants according to the invention comprise or synthesise an mRNA encoding a cyclin SDS like protein having one or more mutations, wherein the mRNA is transcribed from a mutant allele of a cyclin SDS like protein encoding gene. Comprised by these embodiments of the invention are plant cells, plant parts or plants according to the invention comprising or synthesising an mRNA transcribed from a mutant allele of a cyclin SDS like protein encoding gene, characterized in that the mRNA comprises a deletion mutation and/or a missense or non-synonymous mutation and/or a frame shift mutation and/or a non-sense mutation, compared to the corresponding (DNA) coding sequence of the mutant allele of the cyclin SDS like protein encoding gene from which the mRNA is transcribed. Thus, in one aspect any mutation which affects pre-mRNA splicing is encompassed, i.e. which modifies the normal pre-mRNA splicing process, thereby leading to a different mRNA molecule.

Concerning deletion mutations, plant cells or plants according to the invention in one aspect comprise or synthesise an mRNA transcribed from a mutant allele of a cyclin SDS like protein encoding gene, wherein the mRNA comprises a deletion of at least 1, at least 2, at least 4, at least 5, at least 7, at least 8, at least 10, at least 11, at least 13, at least 14 or at least 16 nucleotides compared to the corresponding (DNA) coding sequence of the mutant allele of the cyclin SDS like protein encoding gene from which the mRNA is transcribed. In one aspect the nucleotides(s) deleted in the mRNA are one or more nucleotides of exon 1, exon 2, exon 3 and/or exon 4 of the cyclin SDS like protein. In one aspect the nucleotides are nucleotides of exon 2, e.g. one or more or all nucleotides starting at nucleotide 2186 and ending at nucleotide 2201 of SEQ ID NO 1.

Preferably, plant cells or plants according to the invention comprise or synthesise an mRNA transcribed from a mutant allele of a cyclin SDS like protein encoding gene, characterized in that the mRNA comprises a frame shift mutation and/or a non-sense mutation compared to the (DNA) coding sequence of the mutant allele of the cyclin SDS like protein encoding gene from which the mRNA is transcribed. The non-sense mutation creates a pre-mature stop codon in the mRNA which causes a 3'-end truncation of the mRNA coding sequence and a truncation of a cyclin SDS like protein at the C-terminus. A preferred embodiment of the invention therefore concerns plant cells or plants according to the invention comprising or synthesising an mRNA transcribed from a mutant allele of a cyclin SDS like protein encoding gene, characterized in that the mRNA comprises a truncation of the coding sequence compared to the (DNA) coding sequence of the mutant allele of the cyclin SDS like protein encoding gene from which the mRNA is transcribed. The truncation of the mRNA coding sequence of a cyclin SDS like protein encoding gene preferably is a truncation of at least 100 nucleotides, more preferred of at least 200 nucleotides, even more preferred of at least 300 nucleotides, more preferred of at least 400 nucleotides and more preferred of at least 500 nucleotides, in particular preferred of at least 591 compared to the (DNA) coding sequence of the mutant allele of the cyclin SDS like protein encoding gene from which the mRNA is transcribed. In one aspect the truncation of the mRNA coding sequence results in exon 2, 3 and 4 to be absent; or exon 3 and 4 to be absent; or exon 4 to be absent. In another aspect the truncation of the mRNA coding sequence results in all or part of exon 1, all of exon 2, all of exon 3 and all of exon 4 to be absent. In another aspect, the frame-shift mutation results in all or part of exon 2 to be in a different reading frame. In a different aspect the frame-shift mutation results in all or part of exon 3 and/or exon 4 to be in a different reading frame. The frame shift may be caused by the deletion of one or more nucleotides (any number which is not a multitude of three, such as 1, 2, 4, 5, 7, 8, 10, etc.), whereby the reading frame is changed.

In a further preferred embodiment the plant cells or plants according to the invention comprise or synthesise an mRNA having an identity of at least 58% or 60% preferably at least 70%, more preferably at least 80%, even further preferred at least 90% or particularly preferred at least 95% with the corresponding (DNA) coding sequence indicated in SEQ ID NO 1 with the prerequisite that the mRNA sequence comprises at least a non-sense mutation or a pre-mature stop codon compared to the corresponding (DNA) coding sequence indicated in SEQ ID NO 1, preferably, the non-sense mutation occurs at nucleotide positions 1096 to 1098 in SEQ ID NO 3. In one aspect the premature stop codon is at nucleotides 1687 to 1689 of SEQ ID NO: 1. In a particular preferred embodiment of the invention, the plant cells or plants according to the invention comprise an mRNA having the nucleotide sequence shown under SEQ ID NO 3.

An "mRNA coding sequence" shall have the common meaning herein. An mRNA coding sequence corresponds to the respective DNA coding sequence of a gene/allele apart from that thymine (T) is replaced by uracil (U).

For any of the above described mutations or combinations of mutations (e.g. nucleotide deletion resulting in a frame shift), it is understood that they result in causing a decrease of function or a loss of function in activity of the cyclin SDS like protein in plant cells, plant parts or plants according to the invention.

Another embodiment of the invention concerns plant cells, plant parts or plants, comprising or synthesising a cyclin SDS like protein, characterized in that the amino acid sequence of the cyclin SDS like protein comprises a mutation compared to the corresponding wild type cyclin SDS like protein. The mutation in the cyclin SDS like protein causes a decrease or loss of function in activity of a cyclin SDS like protein in plant cells, plant parts or plants according to the invention.

Particularly preferred are plant cells, plant parts or plants according to the invention comprising or synthesising a cyclin SDS like protein, characterized in that the amino acid sequence of the cyclin SDS like protein comprises a mutation compared to the corresponding wild type cyclin SDS like protein.

The mutation in the cyclin SDS like protein can be an amino acid replacement, insertion, deletion and/or truncation compared to the amino acid sequence of a wild type cyclin SDS like protein. In a preferred embodiment of the invention the amino acid sequence of the cyclin SDS like protein comprises a deletion or truncation, more preferred a truncation at the N-terminus and/or C-terminus, even more preferred a truncation at the C-terminus. Preferably at least 10, at least 25, preferably at least 50, 60, 70, 80, 90 or 100, more preferably at least 150 and even more preferred at least 197 or at least 200, 250, 300 or 339 amino acids are missing from the N-terminal end or C-terminal end of the amino acid sequence compared to the corresponding wild type cyclin SDS like protein. Concerning the C-terminus, the mutation in the cyclin SDS like protein is a truncation of at least 25, preferably at least 50, 60, 70, 80, 90, preferably at least 100, more preferably at least 150 and even more preferred of at least 197 or at least 200, 250, 300 or 339 amino acids compared to the corresponding wild type cyclin SDS like protein. In another aspect the mutation in the cyclin SDS like protein results in the amino acids encoded by exon 2, 3 and 4 to be absent; or the amino acids encoded by exon 3 and 4 to be absent; or in amino acids encoded by exon 4 to be absent. In another aspect the mutation results in all or part of the amino acids encoded by exon 1, all amino acids encoded by exon 2, all amino acids encoded by exon 3 and all amino acids encoded by exon 4 to be absent. In another aspect, the mutation results in all or part of amino acids encoded by exon 2 to be replaced by different amino acids (e.g. due to a reading frame shift). In a different aspect the mutation results in amino acids encoded by all or part of exon 3 and/or exon 4 to be replaced by different amino acids (e.g. due to a reading frame shift). In a different aspect the mutation results in all or part of the Cyclin_C and/or Cyclin_N domain being absent. In yet a different aspect the mutation results in the Cyclin_C and/or Cyclin_N domain comprising one or more amino acids replaced, inserted or deleted.

Further provided are plant cells, plant parts or plants according to the invention comprising or synthesising a cyclin SDS like protein which has at least 58% or at least 60%, preferably at least 70%, more preferably at least 80%, even further preferred at least 90% or particularly preferred at least 95% identity with the amino acid sequence shown under SEQ ID NO 4 or under SEQ ID NO 18. In the most preferred embodiment the protein comprised or synthesized in the plant cells, plant parts or plants has the amino acid sequence shown under SEQ ID NO 4 or under SEQ ID NO: 18.

A further embodiment of the invention therefore concerns plant cells or plants selected from the species watermelon, melon, cucumber, tomato and pepper comprising a mutant allele of a cyclin SDS like protein encoding gene characterized in that the mutant allele comprises or effects one or more of the mutations selected from the group consisting of a) a deletion, truncation, insertion, point mutation, non-sense mutation, missense or non-synonymous mutation, splice-site mutation, frame shift mutation in the genomic sequence;

b) a mutation in one or more regulatory sequences;

c) a deletion, truncation, insertion, point mutation, non-sense mutation, missense or non-synonymous mutation, splice-site mutation, frame shift mutation in the coding sequence;

d) a deletion, truncation, insertion, point mutation, non-sense mutation, missense or non-synonymous mutation, splice-site mutation, frame shift mutation in the pre-mRNA or mRNA; and/or e) a deletion, truncation, insertion or replacement of one or more amino acids in the cyclin SDS like protein.

The above mutant allele results in decreased activity of the mutant cyclin SDS like protein compared to the wild type cyclin SDS like protein. The decreased activity is due to a knock-out of expression of the cyclin SDS like gene, a knock-down of expression of the gene, a loss of function of the encoded mutant cyclin SDS like protein or a decrease of function of the mutant cyclin SDS like protein.

In one aspect, wherein the plant cell or plant is watermelon, the mutant allele of the cyclin SDS like protein is a mutant allele of the allele encoding the protein of SEQ ID NO: 2 or a protein comprising substantial sequence identity to SEQ ID NO: 2, preferably at least 60%, 70%, 80%, 90% sequence identity when the two full length sequences of the functional SDS like protein are pairwise aligned.

In another aspect, wherein the plant cell or plant is melon, the mutant allele of the cyclin SDS like protein is a mutant allele of the allele encoding the protein of SEQ ID NO: 6 or a protein comprising substantial sequence identity to SEQ ID NO: 6, preferably at least 60%, 70%, 80%, 90% sequence identity when the two full length sequences of the functional SDS like protein are pairwise aligned.

In another aspect, wherein the plant cell or plant is cucumber, the mutant allele of the cyclin SDS like protein is a mutant allele of the allele encoding the protein of SEQ ID NO: 12 or a protein comprising substantial sequence identity to SEQ ID NO: 12, preferably at least 60%, 70%, 80%, 90% sequence identity when the two full length sequences of the functional SDS like protein are pairwise aligned.

In another aspect, wherein the plant cell or plant is tomato, the mutant allele of the cyclin SDS like protein is a mutant allele of the allele encoding the protein of SEQ ID NO: 19 or a protein comprising substantial sequence identity to SEQ ID NO: 19, preferably at least 60%, 70%, 80%, 90% sequence identity when the two full length sequences of the functional SDS like protein are pairwise aligned.

In another aspect, wherein the plant cell or plant is pepper, the mutant allele of the cyclin SDS like protein is a mutant allele of the allele encoding the protein of SEQ ID NO: 20 or a protein comprising substantial sequence identity to SEQ ID NO: 20, preferably at least 60%, 70%, 80%, 90% sequence identity when the two full length sequences of the functional SDS like protein are pairwise aligned.

In one aspect the watermelon, melon, cucumber, tomato or pepper plant comprises the mutant cyclin SDS like allele in heterozygous form. In another aspect the watermelon, melon, cucumber, tomato or pepper plant comprises the mutant cyclin SDS like allele in homozygous form, whereby the plant produces seedless fruits upon pollination with own or other pollen. In a preferred aspect the mutant cyclin SDS like allele is a knock out (i.e. the gene is not expressed) or the allele encodes a non-function cyclin SDS like protein.

Seeds from which such plants can be grown are encompassed herein as well as the seedless fruits produced from said plants when the allele is in homozygous form or the seeded fruits produced from said plants when the allele is in heterozygous form. Also any plant parts, such as cuttings, vegetative propagations, cells, etc. comprising at least one mutant cyclin SDS like allele in their genome are provided.

Also propagating and non-propagating cells comprising at least one copy of a mutant cyclin SDS like allele are provided herein. It is understood that such propagating or non-propagating cells can be part of a plant organ or of an entire plant, or they can be isolated, e.g. in a cell or tissue culture.

The seed, plants and plant parts provided herein, comprising at least one mutant cyclin SDS like allele in their genome, are preferably agronomically useful plants, e.g. inbred lines, breeding lines, varieties or cultivars or F1 hybrids. Preferably they having good agronomic characteristics, especially producing marketable fruits of good fruit quality and fruit uniformity.

As used herein, the term "variety" or "cultivar" means a plant grouping within a single botanical taxon of the lowest known rank, which can be defined by the expression of the characteristics resulting from a given genotype or combination of genotypes.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

The watermelon cyclin SDS like allele is located on chromosome 7 (between nucleotide 7450185 and 7445051) of the genome. The chromosome location can be determined by carrying out a BLAST against the whole genome, e.g. on world wide web at icugi.org/pub/genome/watermelon/97103). The cucumber cyclin SDS like allele appears also to be located on chromosome 5 (between nucleotides 848447 and 852718) of the cucumber genome (world wide web at icugi.org/pub/genome/cucumber/Chinese_long/).

For watermelon, a mutant allele of a cyclin SDS like protein encoding gene can be obtained from the watermelon seeds being heterozygous or homozygous for the mutant allele of the cyclin SDS like protein encoding gene, deposited under NCIMB 42532. A wild type allele of a cyclin SDS like protein encoding gene can be obtained from the watermelon seeds being heterozygous or homozygous for the wild type cyclin SDS like protein encoding gene, deposited under NCIMB 42532. For the deposited seeds the respective allele of a cyclin SDS like protein encoding gene was designated emb1. Other mutant alleles of a cyclin SDS like protein encoding gene can be generated de novo, e.g. by mutagenesis or by other methods known to the skilled person. This applies for any plant species.

One example of generating another mutant SDS like allele de novo in watermelon is provided in the Examples. Here, the inventors generated a mutant population by mutagenizing watermelon seeds and then used TILLING to identify a plant comprising a mutant SDS like allele. The identified allele comprises a single nucleotide replacement at nucleotide 1687 of SEQ ID NO: 1, leading to a stop codon. The mutant allele thus encodes a truncated cyclin SDS like protein comprising only amino acids 1 to 223 of the wild type protein (see SEQ ID NO: 18).

Plant cells, plant parts or plants or progeny thereof obtainable/obtained from seeds being heterozygous or homozygous for an allele of a SDS like protein encoding gene, deposited under NCIMB 42532 are also an embodiment of the invention. In a preferred embodiment the plant cells, plant parts or plants or progeny thereof obtained from seeds deposited under NCIMB 42532 are homozygous for a mutant allele of a cyclin SDS like encoding gene. A further comprised embodiment of the invention concerns plant cells, plant parts or plants, homozygous for a mutant allele of a cyclin SDS like protein encoding gene obtained/obtainable after crossing a watermelon plant obtained from seeds of deposit accession number NCIMB 42532 with another plant. Preferably the plant cells or plants obtained/obtainable after crossing a plant obtained from seeds of deposit accession number NCIMB 42532 with another plant are subsequently self-pollinated and optionally in a further step plants are selected which produce seedless fruits and/or plants are selected which are homozygous for a mutant allele of a cyclin SDS like encoding gene.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

"Wild type allele" refers herein to a version of a gene encoding a fully functional protein (wild type protein). A sequence of a gene encoding a fully functional cyclin SDS like protein is for example the coding sequence of the wild type cyclin SDS like protein sequences shown under SEQ ID NO 1 (from cultivated watermelon) and SEQ ID NO 5 (from cultivated melon). The amino acid sequence encoded by this wild type cyclin SDS like protein encoding gene is depicted in SEQ ID NO 2 or SEQ ID NO 6, respectively. Other wild type cyclin SDS like proteins are shown under SEQ ID NO 12 (cucumber), SEQ ID NO: 19 (tomato) and SEQ ID NO: 20 (pepper). Other cyclin SDS like protein encoding nucleic acid sequences encoding fully functional cyclin SDS like protein alleles (i.e. variant alleles, or allelic variants) exist in other plants and may comprise substantial sequence identity with at least the coding sequence of the nucleic acid sequences shown under SEQ ID NO 1 or SEQ ID NO 5 or with the amino acid sequences shown under SEQ ID NO 2 or SEQ ID NO 6 or SEQ ID NO: 12, or SEQ ID NO: 19 or SEQ ID NO: 20. For example the cultivated cucumber cyclin SDS like protein of SEQ ID NO 12 has 86% amino acid sequence identity to the wild type cyclin SDS like protein of melon (SEQ ID NO 6) and 70% amino acid sequence identity to the wild type SDS like protein of watermelon (SEQ ID NO 2).

A "mutant allele" is to be understood in connection with the present invention to mean an allele which has a mutation compared to the corresponding wild type allele. An example of a mRNA transcribed from a mutant allele of a cyclin SDS like protein encoding gene is shown under SEQ ID NO 3. The corresponding amino acid sequence encoded by the mRNA shown under SEQ ID NO 3 is shown under SEQ ID NO 4.

The term "locus" (loci plural) means a specific place or places or a site on a chromosome where for example a gene or genetic marker is found.

A "mutation" in a nucleic acid molecule (DNA or RNA) is a change of one or more nucleotides compared to the corresponding wild type sequence, e.g. by replacement, deletion or insertion of one or more nucleotides. Examples of such a mutation are point mutation, nonsense mutation, missense mutation, splice-site mutation, frame shift mutation or a mutation in a regulatory sequence.

A "nucleic acid molecule" shall have the common understanding in the art. It is composed of nucleotides comprising either of the sugars deoxyribose (DNA) or ribose (RNA).

A "point mutation" is the replacement of a single nucleotide, or the insertion or deletion of a single nucleotide.

A "nonsense mutation" is a (point) mutation in a nucleic acid sequence encoding a protein, whereby a codon in a nucleic acid molecule is changed into a stop codon. This results in a pre-mature stop codon being present in the mRNA and results in translation of a truncated protein. A truncated protein may have decreased function or loss of function.

A "missense or non-synonymous mutation" is a (point) mutation in a nucleic acid sequence encoding a protein, whereby a codon is changed to code for a different amino acid. The resulting protein may have decreased function or loss of function.

A "splice-site mutation" is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have decreased function or loss of function.

A "frame shift mutation" is a mutation in a nucleic acid sequence encoding a protein by which the reading frame of the mRNA is changed, resulting in a different amino acid sequence. The resulting protein may have decreased function or loss of function.

A "deletion" in context of the invention shall mean that anywhere in a given nucleic acid sequence at least one nucleotide is missing compared to the nucleic sequence of the corresponding wild type sequence or anywhere in a given amino acid sequence at least one amino acid is missing compared to the amino acid sequence of the corresponding (wild type) sequence.

A "truncation" shall be understood to mean that at least one nucleotide at either the 3'-end or the 5'-end of the nucleotide sequence is missing compared to the nucleic sequence of the corresponding wild type sequence or that at least one amino acid at either the N-terminus or the C-terminus of the protein is missing compared to the amino acid sequence of the corresponding wild type protein, whereby in a 3'-end or C-terminal truncation at least the first nucleotide at the 5'-end or the first amino acid at the N-terminus, respectively, is still present and in a 5'-end or N-terminal truncation at least the last nucleotide at the 3'-end or the last amino acid at the C-terminus, respectively, is still present. The 5'-end is determined by the ATG codon used as start codon in translation of a corresponding wild type nucleic acid sequence.

"Replacement" shall mean that at least one nucleotide in a nucleic acid sequence or one amino acid in a protein sequence is different compared to the corresponding wild type nucleic acid sequence or the corresponding wild type amino acid sequence, respectively, due to an exchange of a nucleotide in the coding sequence of the respective protein.

"Insertion" shall mean that the nucleic acid sequence or the amino acid sequence of a protein comprises at least one additional nucleotide or amino acid compared to the corresponding wild type nucleic acid sequence or the corresponding wild type amino acid sequence, respectively.

"Pre-mature stop codon" in context with the present invention means that a stop codon is present in a coding sequence (cds) which is closer to the start codon at the 5'-end compared to the stop codon of a corresponding wild type coding sequence.

A "mutation in a regulatory sequence", e.g. in a promoter or enhancer of a gene, is a change of one or more nucleotides compared to the wild type sequence, e.g. by replacement, deletion or insertion of one or more nucleotides, leading for example to decreased or no mRNA transcript of the gene being made.

"Homozygous" is referred herein to mean that all copies of a given gene or allele at a corresponding chromosomal locus in a cell or an organism are identical. "Homozygous for a mutant allele" means that all copies of the respective mutant allele at the corresponding chromosomal locus in a cell or an organism are identical.

"Heterozygous" is referred herein to mean that at least one copy of a given gene or allele at a specific chromosomal locus in a cell or an organism is different from the other copies of the gene(s) or allele(s) at the corresponding locus/loci in the other chromosome(s). "Heterozygous for a mutant allele" means that at least one allele at a specific chromosomal locus in a cell or an organism has a different sequence than the allele(s) at the corresponding locus/loci in the other chromosome(s).

A "mutation in a protein" is a change of one or more amino acid residues compared to the wild type sequence, e.g. by replacement, deletion, truncation or insertion of one or more amino acid residues.

Biotechnological methods for introducing mutations into a desired gene/allele of a plant cell or plant are known in the art. Therefore, mutant alleles of a cyclin SDS like protein encoding gene can be produced in plant cells or plants by using these methods. Examples for such technologies are in particular mutagenesis techniques or enzymes which induce double stranded DNA breaks (double stranded DNA break inducing enzyme (DSBI)) in the genome of plants. Known and practised technologies are rare-cleaving endonucleases and custom-tailored rare-cleaving endonucleases including but not limited to homing endonucleases, also called mega-nucleases, transcription activator-like effectors fused to the catalytic domain of a nuclease (TALENs) and so-called CRISPR/Cas systems.

All these technologies are eligible for introducing a mutation into genes in plant cells or plants. Therefore, plant cells and plants according to the invention having a mutant allele of a cyclin SDS like protein encoding gene, wherein the mutation into the mutant allele was introduced by rare-cleaving endonucleases or custom-tailored rare-cleaving endonucleases are also an embodiment of the invention. Concerning custom-tailored rare-cleaving endonucleases the mutation in the mutant allele of a cyclin SDS like protein has preferably been introduced by a meganuclease, a TAL-ENs or a CRISPR/Cas system.

As used herein, a "double stranded DNA break inducing enzyme (DSBI)" is an enzyme capable of inducing a double stranded DNA break at a particular nucleotide sequence, called the "recognition site". Rare-cleaving endonucleases are DSBI enzymes that have a recognition site of about 14 to 70 consecutive nucleotides, and therefore have a very low frequency of cleaving, even in larger genomes such as most plant genomes.

"Homing endonucleases, also called meganucleases", constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrasts the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level.

A list of other rare cleaving meganucleases and their respective recognition sites is provided in Table I of WO 03/004659 (pages 17 to 20) (incorporated herein by reference). These include I-Sce I, I-Chu I, I-Dmo I, I-Cre I, I-Csm I, PI-Fli I, Pt-Mtu I, I-Ceu I, I-Sce II, I-Sce III, HO, PI-Civ I, PI-Ctr I, PI-Aae I, PI-BSU I, PI-DhaI, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I or PI-Tsp I.

Furthermore, methods are available to design "custom-tailored rare-cleaving endonucleases" that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO94/18313 or WO95/09233 and in Isalan et al., 2001, Nature Biotechnology 19, 656-660; Liu et al. 1997, Proc. Natl. Acad. Sci. USA 94, 5525-5530). Custom-made mega-nucleases can be produced by selection from a library of variants, as described in WO2004/067736. Custom made meganucleases with altered sequence specificity and DNA-binding affinity may also be obtained through rational design as described in WO2007/047859.

Another example of custom-designed endonucleases include the so-called "TALE nucleases (TALENs)", which are based on transcription activator-like effectors (TALEs) from the bacterial genus *Xanthomonas* fused to the catalytic domain of a nuclease (e.g. FOKI). The DNA binding specificity of these TALEs is defined by repeat-variable diresidues (RVDs) of tandem-arranged 34/35-amino acid repeat units, such that one RVD specifically recognizes one nucleotide in the target DNA. The repeat units can be assembled to recognize basically any target sequences and fused to a catalytic domain of a nuclease create sequence specific endonucleases (see e.g. Boch et al., 2009, Science 326: p 1509-1512; Moscou and Bogdanove, 2009, Science 326: p 1501; Christian et al., 2010, Genetics 186: p 757-761; and WO10/079430, WO11/072246, WO2011/154393, WO11/146121, WO2012/001527, WO2012/093833, WO2012/104729, WO2012/138927, WO2012/138939). WO2012/138927 further describes monomeric (compact) TALENs and TALENs with various catalytic domains and combinations thereof.

Recently, a new type of customizable endonuclease system has been described; the so-called "CRISPR/Cas system", which employs a special RNA molecule (crRNA) conferring sequence specificity to guide the cleavage of an associated nuclease Cas9 (Jinek et al, 2012, Science 337: p 816-821). Such custom designed rare-cleaving endonucleases are also referred to as non-naturally occurring rare-cleaving endonucleases.

A further method known in the art for introducing mutations into a gene/allele of a plant cell or plant is the so-called "in vivo mutagenesis". Further discussion of the respective technology is given herein below.

Plant cells or plants according to the invention having a mutant allele of a cyclin SDS like protein encoding gene, wherein the mutation into the mutant allele was introduced by in vivo mutagenesis are also an embodiment of the invention.

Various technologies commonly known in the art are suited to create insertion mutations in plant cells or plants.

Further embodiments of the invention are plant cells and plants according to the invention having a mutant allele of a cyclin SDS like protein encoding gene, wherein the mutation into the mutant allele was introduced by insertion mutagenesis.

The plant cells according to the invention and plants according to the invention having a mutant allele of a cyclin SDS like protein encoding gene can be produced by so-called insertion mutagenesis. In particular, insertion of trans-posons and transfer DNA (T-DNA) sequences into genes/alleles encoding cyclin SDS like proteins are suitable for decreasing the expression and/or activity of the respective genes/alleles in which they are integrated (Thorneycroft et al., 2001, Journal of experimental Botany 52 (361), 1593-1601).

Additional discussion of the respective technologies known to a person skilled in the art will be provided herein further below.

"Insertion mutagenesis" is to be understood to mean particularly the insertion of transposons or so-called transfer DNA (T-DNA) into a gene coding for a cyclin SDS like protein, whereby, as a result of which, the activity of a cyclin SDS like protein in the cell concerned is decreased or a non-functional cyclin SDS like protein is produced.

In a further preferred embodiment, the plants according to the invention are male fertile plants.

The plants according to the invention are male fertile and produce seedless fruits when the mutant cyclin SDS like allele is present in homozygous form. The advantage of male fertile plants over male sterile plants is that they will produce viable pollen and thus there is no need to plant a second, so called pollinator plant in the same field for inducing fruit set and development on the seedless fruit producing female plant. The whole area under cultivation thus can be planted with plants producing seedless fruits, leading to an increase of yield of seedless fruits per area cultivated. Also, synchrony of flowering and fertilisation time is given for the male and female plant parts, because ovules and pollen are produced by the same plant. This ensures sufficient pollination to take place for producing the most possible amounts of fruits.

In context with the present invention, "male fertile plant" is to be understood to be a plant producing viable pollen. That viable or fertile pollen is produced can e.g. be shown by using the pollen from the respective plant for cross-pollinating another, different plant and obtaining viable seeds from this cross.

The seedless fruit producing phenotype of plants according to the invention in one aspect is not only be generated in diploid plants but also in polyploidy plants. In one aspect plants according to the invention produce seedless fruits also when they have different degree of ploidy. It is therefore well understood that the plant cells or plants according to the invention comprise plants having any degree of ploidy comprising plants with even numbered degree of ploidy (2n, 4n, 6n, 8n etc.) and plants with uneven numbered degree of ploidy (3n, 5n etc.). In one aspect, the mutant cyclin SDS like protein encoding gene is homozygous in diploid plants, but in another aspect the mutant SDS like protein is homozygous in polyploidy plants, such as tetraploid watermelons. "Homozygous in polyploidy plants" means that the locus on each chromosome comprises the mutant allele and not the wild type allele of the gene.

Polyploidisation is widespread in plants. It is responsible for increasing genetic diversity and producing species showing increase in robustness, size, vigour and disease resistance. Obvious advantages for polyploid plants are heterosis and gene redundancy.

A number of today cultivated broad acre and plantation crops have undergone one or more genome duplications. Examples are cotton (multiplication factor ×6), potato (×2, ×3), bread wheat (×3), oil seeds (×3), corn (×2), soybean (×2), sunflower (×2), banana (×2), apple (×2) and coffee (×2) (Renny-Byfield 7 Wendel, 2014, American J. Botany, 101 (10), 1711-1725).

In particular in vegetable breeding, polyploidy in various plants was induced by the use of chemicals including colchicine, colchamine, oryzalin, colcemid, trifluralin or amiprophosmethyl. Examples for genome duplications in vegetables produced by the use of chemicals are diploid brussels sprouts from haploid plants (2×), tetraploid peas (2×), tetraploid watermelons (2×), tetraploid muskmelons (2×), tetraploid onions (2×), octaploid cocoyams (4×), tetraploid snake gourds (2×), triploid and tetraploid fluted pumpkins (1.5×, 2×), tetraploid cucumbers (2×) and tetraploid french beans (2×) (Kazi, 2015, J. Global Biosciences 4(3), 1774-1779).

Plants comprising a mutant allele of a cyclin SDS like protein encoding gene can be produced by various methods commonly known to a person skilled in the art. These methods comprise the use of seeds deposited under accession number NCIMB 42532. A particular advantage of these deposited seeds is that the plants grown from the seeds which comprise the mutant allele will be male fertile. Thus, the mutant allele of the cyclin SDS like protein encoding gene present in those plants can be introduced into other plants by using the pollen of plants comprising a mutant allele of the cyclin SDS like protein encoding gene for fertilising other plants, in particular other watermelon plants, especially cultivated watermelon. As the mutant allele of a cyclin SDS like protein encoding gene is recessive, seedless fruit production is only seen if no dominant wild type allele of a cyclin SDS like protein encoding gene is present in the respective plant. Thus, in case a wild type allele of a cyclin SDS like protein encoding gene is present in plants, these plants produce seeded fruits. When transferring a mutant allele of a cyclin SDS like protein encoding gene from a diploid seed, homozygous for a mutant allele of a cyclin SDS like protein encoding gene (e.g. from deposit accession number NCIMB 42532 or progeny thereof) to another plant which does not contain a recessive mutant allele of a cyclin SDS like protein encoding gene, the F1 generation will be heterozygous and will not display the seedless fruit phenotype. The F1 needs first to be self-pollinated for obtaining plants comprising the seedless fruit phenotype due to two copies (homozygous) of the recessive mutant allele being present.

A diploid plant comprising two copies of a mutant allele of a cyclin SDS like protein encoding gene can be used to make a tetraploid plant comprising four copies of a mutant allele of a cyclin SDS like protein encoding gene. Such a tetraploid will have the same phenotype as the diploid, i.e. produce seedless fruits (which are tetraploid) and viable pollen.

When transferring a mutant allele of a cyclin SDS like protein encoding gene from a tetraploid plant to another tetraploid plant not comprising the recessive mutant allele of a cyclin SDS like protein encoding gene, the F1 generation will be heterozygous and does not display the seedless fruit phenotype. Again the seedless fruit phenotype will only be seen in the generation obtained from the self-pollinated F1 generation.

As mentioned, tetraploid plants comprising a seedless fruit phenotype can be generated by duplicating the chromosomes of a diploid plant homozygous for mutant allele of a cyclin SDS like protein encoding gene (e.g. from seed, homozygous for a mutant allele of a cyclin SDS like protein encoding gene from deposit accession number NCIMB 42532 or from plants, homozygous for a mutant allele of a cyclin SDS like protein encoding gene obtained after crossing a plant obtained from seeds of deposit accession number NCIMB 42532 with another plant and optionally subsequently self-pollinating the plants obtained from said cross). The tetraploid plants so obtained comprise four copies of a mutant allele of a cyclin SDS like protein encoding gene mutant allele.

It is commonly understood in the art that sexually reproducing cells of plants (pollen and ovule) comprise a set of chromosomes which is half of the set of the remaining cells of said plant. Plant pollen and ovules can be regenerated into whole plants. In case of plants having an even numbered degree of ploidy it is therefore generally possible to reduce the degree of ploidy by half upon regeneration of pollen or ovules. From plants according to the invention having an even numbered degree of ploidy (e.g. 2n, 4n, 6n, 8n etc.) plants having a bisected set of chromosomes (e.g. In, 2n, 3n, 4n, etc., respectively) can be produced by means of pollen or ovule regeneration.

Diploid plants according to the invention can e.g. be regenerated from pollen or ovule cells comprising a mutant allele of a cyclin SDS like protein encoding gene, the pollen or ovule cells being obtained from a tetraploid plant comprising a mutant allele of a cyclin SDS like protein encoding gene. Preferably, the pollen or ovule cells being obtained from a tetraploid plant comprise the mutant allele of a cyclin SDS like protein encoding gene in homozygous state. The derived diploid plants may then be used in further breeding and in generating plants having a seedless fruit phenotype.

Triploid plants can be produced by crossing a diploid (2n) plant according to the invention with a tetraploid (4n) plant according to the invention. The hybrid plant seeds originating from said cross will be triploid (3n). Preferably the diploid (2n) and tetraploid (4n) plants according to the invention crossed with each other both are homozygous for a mutant allele of a cyclin SDS like protein encoding gene. The resulting triploid seeds (and triploid plants grown from the seeds) will have three copies of the mutant allele. The diploid plant used for producing a triploid hybrid can e.g. be plants obtained/obtainable from seeds being homozygous for a mutant allele of a cyclin SDS like protein encoding gene obtained from seeds of deposit accession number NCIMB 42532.

Plants (e.g. diploid, triploid or tetraploid, or another ploidy) and plant parts (such as fruits) comprising a mutant allele of a cyclin SDS like protein encoding gene obtainable/obtained by one of the methods just described are also an embodiment of the invention. Also seeds from which such plants can be grown are an embodiment of the invention.

In a preferred embodiment of the invention the plant cells or plants according to the invention have an even numbered degree of ploidy, preferably, they are diploid (2n) or tetraploid (4n).

Plants with an uneven numbered degree of ploidy, e.g. triploid (3n) plants are commonly male and female sterile, because during meiosis the chromosomes cannot be equally divided to the daughter cells. The advantage of plants with an even numbered degree of ploidy, e.g. diploid (2n) or tetraploid (4n) plants over plants with an uneven numbered degree of ploidy, e.g. triploid (3n) plants is that plants with even numbered degree of ploidy can produce viable pollen and/or viable ovules. As a consequence plants with an even numbered degree of ploidy can be grown without the need of a second, different, so called pollinator plant needed for inducing fruit set and development in the plant with uneven numbered degree of ploidy. Pollinator plants will also produce fruits which commonly will be seed bearing (or seeded). These seed bearing fruits have to be separated from the seedless fruits upon or after harvesting. Thus, plants having an even numbered degree of ploidy have the advantage over plants with uneven numbered degree of ploidy that there is no need to separate undesired seed bearing fruits produced by pollinator plants from the desired seedless fruits.

"Even numbered degree of ploidy" in context of the present invention means that the number of homologous chromosome sets present in a cell or organism when divided by two results in an integer. The cells or organisms thus are diploid (2n), tetraploid (4n), hexaploid (6n), octaploid (8n) etc.

"Uneven numbered degree of ploidy" in context of the present invention means that the number of homologous chromosome sets present in a cell or organism when divided by two does not result an integer. The cells or organisms thus are haploid (In), triploid (3n) etc.

"Diploid plant cell or plant" in context of the present invention means a plant, vegetative plant part(s), fruit or seed or plant cell, having two sets of corresponding chromosomes, designated herein as 2n.

"Tetraploid cell or plant" in context of the present invention means a plant, vegetative plant part(s), fruit or seed or plant cell, having four sets of corresponding chromosomes, designated herein as 4n.

The plant cells according to the invention can be those plant cells which can be regenerated into a whole plant or those which cannot be regenerated into whole plants. Thus, the plant cells according to the invention may be those plant cells which are not eligible to regenerate a whole plant.

In a preferred embodiment the plants according to the invention are male fertile and have an even numbered degree of ploidy. Preferably, plants according to the invention are male fertile and are diploid (2n) or tetraploid (4n).

In another preferred embodiment, the plants according to the invention are stenospermocarpic plants. More preferably the plants according to the invention are male fertile stenospermocarpic plants. Even further preferred the plants according to the invention are male fertile, stenospermocarpic and have an even numbered degree of ploidy. In particular preferred are plants according to the invention which are male fertile, stenospermocarpic, diploid (2n) or tetraploid (4).

Stenospermocarpic plants produce seedless fruits. Male fertile stenospermocarpic plants have the advantage over known stenospermocarpic plants that they do not need a different pollinator plant grown in the same area but that they nevertheless produce seedless fruits. Pollinator plants will produce undesired seed bearing fruits, which will have to be separated from the seedless fruits. Thus, stenospermocarpic male fertile plants have the advantage that there is no competition for growing space and nutrients between a plant producing the desired seedless fruits and the polliniser plants, which increases yield of the desired seedless fruits per planting area available.

"Stenospermocarpy" is generally understood in the art and also to be understood in connection with the present invention to mean that induction of fruit set and development requires pollination but without the fruits producing mature or viable seeds. Mature or viable seeds are not developed in stenospermocarpic plants due to arrested seed development or degradation of ovules and/or embryos and/or endosperm or abortion of the ovules and/or embryos and/or endosperm before maturity is reached.

To be differentiated from stenospermocarpy is parthenocarpy. "Parthenocarpy" is generally understood in the art and also to be understood in connection with the present invention to describe the development of fruits without fertilization of the female ovule. A pollination process is not needed for producing fruits which fruits however as a consequence of the lack of pollination are seedless.

In a further preferred embodiment of the invention, the plants according to the invention produce seedless fruits.

The fruits of plants according to the invention may contain structures which have a seed like appearance. These structures having a seed like appearance are normally white and soft compared to the seeds of wild type plants which are dark brown or black and hard. The structures having a seed like appearance in fruits of plant according to the invention are denoted sometimes as empty seeds. However, they are no true seeds, because they do not comprise a viable embryo but are structures originating from the ovule integument.

In a more preferred embodiment of the invention the plants according to the invention produce seedless fruits and/or are male fertile and/or have an even degree of ploidy and/or are stenospermocarpic. Even more preferred the plants according to the invention produce seedless fruits, are male fertile, are diploid (2n) or tetraploid (4n) and are stenospermocarpic.

The term "fruit" in its botanical meaning is commonly understood to be a seed bearing structure developed from the ovary of angiosperm flowers.

A "seedless fruit" as commonly used in the art and in particular in breeding, although being somehow contradicting the botanical meaning of "fruit", is to be understood in context with the present invention to be a fruit without mature or viable seeds. Mature or viable seeds can be germinated in soil under conditions appropriate for the respective plant and grown into plants. This test can be used to determine if a plant produces seedless fruits. Seedless fruits will not produce seed which will germinate and grow into a plant under conditions appropriate for the respective plant.

By knowing the causative gene for the production of seedless fruits disclosed herein, it is now possible to produce seedless fruit producing plants by various known methods. These methods can rely on producing and selecting plants having mutant alleles encoding non-functional cyclin SDS like proteins or mutant alleles encoding cyclin SDS like proteins with decreased or loss of function or by using conventional mutation agents like chemicals, high energy radiation (e.g. x-rays, neutron radiation, gamma radiation or UV radiation). It is also possible by means of gene technology to produce plants having non-functional cyclin SDS like proteins or having decreased activity of cyclin SDS like proteins.

Plants according to the invention can be produced by introducing one or more mutations into an allele of a cyclin SDS like protein encoding gene.

A further embodiment of the present invention therefore concerns a method for production of a plant comprising the steps of
a) introducing mutations in a population of plants
b) selecting a male fertile plant producing seedless fruits
c) verifying if the plant selected under b) has a mutation in an allele of a cyclin SDS like protein encoding gene, optionally
d) growing/cultivating the plants obtained under c).

Thus one aspect is a method for production of a plant comprising the steps of
a) introducing mutations in a population of plants
b) selecting a male fertile plant producing seedless fruit
c) verifying if the plant selected under b) has a mutation in an allele encoding a cyclin SDS like protein encoding gene and selecting a plant comprising such a mutation, and optionally
d) growing/cultivating the plants obtained under c), wherein the wild type allele of the gene encodes a cyclin SDS like protein comprising at least 60% sequence identity to any one of the proteins selected from the group of: SEQ ID NO 2 or SEQ ID NO 6 or SEQ ID NO 12 or SEQ ID NO 19 or SEQ ID NO 20.

However, in one aspect the order of the steps can also be different.

So in one aspect a method for production of a plant comprising the steps of
a) introducing mutations in a population of plants
b) identifying a plant which has a mutation in an allele encoding a cyclin SDS like protein encoding gene and optionally
c) determining whether the plant is male fertile and whether the plant, or a progeny plant produced by self-fertilization, produces seedless fruits.

Optionally, the method comprises selecting a plant comprising at least one copy of a mutant allele of a gene encoding a cyclin SDS like protein. The mutant allele, when in homozygous form, results in the production of seedless fruits. The plant comprising the allele is male fertile.

In one aspect the wild type allele of the gene encodes a cyclin SDS like protein comprising at least 60% sequence identity to any one of the proteins selected from the group of: SEQ ID NO 2 or SEQ ID NO 6 or SEQ ID NO 12 or SEQ ID NO 19 or SEQ ID NO 20.

Also, step a) of these methods (i.e. introducing mutations in a population of plants) can also be omitted in the above methods.

"Population of plants" shall mean in context with the present invention more than one whole plant and shall comprise also plant parts, fruits, seeds or plant cells. The plant parts, fruits, seeds or plant cells in each case originate from more than one plant meaning that concerning a "population of plant parts, fruits, seeds or plant cells", the plant parts, fruits, seeds or plant cells, respectively, are not obtained from a single plant but from a plurality of plants.

Chemical substances, which can be used to produce chemically induced mutations, and the mutations resulting from the effect of the corresponding mutagens are, for example described in Ehrenberg and Husain, 1981, (Mutation Research 86, 1-113), Müller, 1972 (Biologisches Zentralblatt 91 (1), 31-48). The production of rice mutants using gamma radiation, ethyl methane sulphonate (EMS), N-methyl-N-nitrosurea or sodium azide (NaN₃) is described, for example, in Jauhar and Siddiq (1999, Indian Journal of Genetics, 59 (1), 23-28), in Rao (1977, Cytologica 42, 443-450), Gupta and Sharma (1990, Oryza 27, 217-219) and Satoh and Omura (1981, Japanese Journal of Breeding 31 (3), 316-326). The production of wheat mutants using NaN₃ or maleic hydrazide is described in Arora et al. (1992, Annals of Biology 8 (1), 65-69). An overview of the production of wheat mutants using different types of energy-rich radiation and chemical substances is presented in Scarascia-Mugnozza et al. (1993, Mutation Breeding Review 10, 1-28). Svec et al. (1998, Cereal Research Communications 26 (4), 391-396) describes the use of N-ethyl-N-nitrosurea for producing mutations in triticale. The use of MMS (methyl methane sulphonic acid) and gamma radiation for the production of millet mutants is described in Shashidhara et al. (1990, Journal of Maharashtra Agricultural Universities 15 (1), 20-23).

The manufacture of mutants in plant species, which mainly propagate vegetatively, has been described, for example, for potatoes, which produce a modified starch (Hovenkamp-Hermelink et al. (1987, Theoretical and Applied Genetics 75, 217-221) and for mint with increased oil yield or modified oil quality (Dwivedi et al., 2000, Journal of Medicinal and Aromatic Plant Sciences 22, 460-463).

All these methods are basically suitable in the method for production of a plant according to the invention for producing mutant alleles in genes encoding a cyclin SDS like protein. In the method for production of a plant according to the invention preferably the mutant population is produced by applying ethyl methane sulphonate (EMS) to plants or seeds of plants for introducing mutations.

Selecting plants producing seedless fruits can be done by simply visible screening/phenotyping the fruits. As the phenotype of seedlessness is only seen in homozygous condition, selfing of the population of mutagenized plants is preferred before phenotyping. That fertile pollen is produced by a plant can e.g. be shown by using the pollen from the respective plant for cross-pollinating another, different, female fertile plant. In case the seeds from this cross are viable the pollen used in the cross-pollinations was fertile. Mutations in the appropriate alleles, in particular in alleles of cyclin SDS like protein encoding genes, can be found with the help of methods known to the person skilled in the art.

In particular, analyses based on hybridisations with probes (Southern Blot), amplification by means of polymerase chain reaction (PCR), sequencing of related genomic sequences and the search for individual nucleotide exchanges can be used for this purpose. A method of identifying mutations based on hybridisation patterns is, for example, the search for restriction fragment length differences (Restriction Fragment Length Polymorphism, RFLP) (Nam et al., 1989, The Plant Cell 1, 699-705; Leister and Dean, 1993, The Plant Journal 4 (4), 745-750). A method based on PCR is, for example, the analysis of amplified fragment length differences (Amplified Fragment Length Polymorphism, AFLP) (Castiglioni et al., 1998, Genetics 149, 2039-2056; Meksem et al., 2001, Molecular Genetics and Genomics 265, 207-214; Meyer et al., 1998, Molecular and General Genetics 259, 150-160). The use of amplified fragments excised with restriction endonucleases (Cleaved Amplified Polymorphic Sequences, CAPS) can also be used upon for the identification of mutations (Konieczny and Ausubel, 1993, The Plant Journal 4, 403-410; Jarvis et al., 1994, Plant Molecular Biology 24, 685-687; Bachem et al., 1996, The Plant Journal 9 (5), 745-753). Methods for the determination of SNPs have been described by Qi et al. (2001, Nucleic Acids Research 29 (22), e116) Drenkard et al. (2000, Plant Physiology 124, 1483-1492) and Cho et al. (1999, Nature Genetics 23, 203-207) amongst others. Methods, which allow several plants to be investigated for mutations in certain genes in a short time, are particularly suitable. Such a method, so-called TILLING (Targeting Induced Local Lesions IN Genomes), has been described by McCallum et al. (2000, Plant Physiology 123, 439-442).

It is well known in the art, that today also other methods are useful for identifying plant cells according to the invention and plants according to the invention having a mutant allele of a cyclin SDS like protein encoding gene. These methods comprise e.g. so-called forward screening approaches. In the forward screening approaches a mutant population is produced. Plants of the mutant population, e.g. M2 plants are screened for seedless fruit producing plants, which are then crossed to various different inbred lines for producing a mapping population. The mapping population is then analysed by methods well known in the art to identify the allele causing the seedless fruit phenotype. Other methods for identifying if a plant cell or plant comprises a mutant allele of a cyclin SDS like protein encoding gene comprise sequencing of the respective alleles and SNP marker analyses with methods common in the art and e.g. discussed in Thomson (2014, Plant Breeding and Biotechnology 2, 195-212).

These methods are basically suitable for identifying plant cells according to the invention and plants according to the invention having a mutant allele of a cyclin SDS like protein encoding gene.

Growing the male fertile, seedless fruit producing plants having a mutant allele of a cyclin SDS like protein encoding gene identified in the method for production of a plant according to the invention can be done by conventional methods in a greenhouse or in the field. Cultivation and/or propagation of these plants can be done by methods common in the art like e.g. by cuttings, in vitro tissue, cell, protoplast, embryo or callus cultures or micropropagation or by grafting cuttings to a different rootstock.

In a preferred embodiment of the invention, the methods for production of a plant according to the invention are used for producing plants according to the invention. The preferred embodiments described above for plants according to the invention are accordingly applicable to the methods for production of a plant according to the invention.

Plants obtainable/obtained by the method for production of a plant according to the invention are also an embodiment of the invention.

Various methods available in gene technology offer further possibilities to produce plants having mutant alleles of a cyclin SDS like protein encoding gene or having non-functional cyclin SDS like proteins or having decreased activity of cyclin SDS like proteins or showing a decreased expression of cyclin SDS like proteins.

All these methods are based on the introduction of a foreign or of several foreign nucleic acid molecules into the genome of plant cells or plants and therefore are basically suitable for producing plant cells according to the invention and plants according to the invention.

A further embodiment of the invention therefore concerns a method for production of a plant comprising the steps of
  a) introduction of a foreign nucleic acid molecule into a plant, wherein the foreign nucleic acid molecule is chosen from the group consisting of
    i) DNA molecules, which code at least one antisense RNA, which effects a reduction in the expression of an endogenous gene encoding a cyclin SDS like protein;
    ii) DNA molecules, which by means of a co-suppression effect lead to the reduction in the expression of an endogenous gene encoding a cyclin SDS like protein;
    iii) DNA molecules, which code at least one ribozyme, which splits specific transcripts of an endogenous gene encoding a cyclin SDS like protein;
    iv) DNA molecules, which simultaneously code at least one antisense RNA and at least one sense RNA, wherein the said antisense RNA and the said sense RNA form a double-stranded RNA molecule, which effects a reduction in the expression of an endogenous gene encoding a cyclin SDS like protein having (RNAi technology);
    v) nucleic acid molecules introduced by means of in vivo mutagenesis, which lead to a mutation or an insertion of a heterologous sequence in an endogenous gene encoding a cyclin SDS like protein, wherein the mutation or insertion effects a reduction in the expression of a gene encoding a cyclin SDS like protein or results in the synthesis of an inactive cyclin SDS like protein;

vi) nucleic acid molecules, which code an antibody, wherein the antibody results in a decrease in the activity of an endogenous gene encoding a cyclin SDS like protein due to the bonding of the antibody to an endogenous cyclin SDS like protein, vii) DNA molecules, which contain transposons, wherein the integration of these transposons leads to a mutation or an insertion in an endogenous gene encoding a cyclin SDS like protein, which effects a reduction in the expression of an endogenous gene encoding a cyclin SDS like protein, or results in the synthesis of an inactive cyclin SDS like protein;

viii) T-DNA molecules, which, due to insertion in an endogenous gene encoding a cyclin SDS like protein, effect a reduction in the expression of an endogenous gene encoding a cyclin SDS like protein, or result in the synthesis of an inactive cyclin SDS like protein, and/or ix) nucleic acid molecules encoding rare-cleaving endonucleases or custom-tailored rare-cleaving endonucleases preferably a meganuclease, a TAL-ENs or a CRISPR/Cas system b) selecting a plant producing seedless fruits, optionally c) verifying if the plant selected under b) has a decreased activity of a cyclin SDS like protein compared to wild type plants into whose genome no foreign nucleic acid molecules had been integrated, and optionally d) growing/cultivating the plants obtained under c).

In a preferred embodiment of the invention, the method according to the invention comprising introducing a foreign nucleic acid molecule into a plant cell concerns a method for the production of a male fertile plant, meaning that selection of a plant being male fertile and producing seedless fruit takes place (in step b and/or c).

The decrease of the activity of cyclin SDS like proteins in plant cells or plants according to the invention or in the method according to the invention comprising introducing a foreign nucleic acid molecule into a plant cell can be brought about by expression of antisense or co-suppression constructs.

For inhibiting the expression of genes by means of antisense or co-suppression technology, a DNA molecule can be used, for example, which includes the whole coding sequence for a cyclin SDS like protein, including any existing flanking sequences, as well as DNA molecules, which include only parts of the coding sequence, whereby these parts must be long enough to produce an antisense effect or a co-suppression effect respectively in the cells. In general, sequences up to a minimum length of 20 bp or 21 bp (or nucleotides), preferably a minimum length of at least 100 bp (or nucleotides), particularly preferably of at least 500 bp (or nucleotides) are suitable. For example, the DNA molecules have a length of 21-100 bp (or nucleotides), preferably of 100-500 bp (or nucleotides), particularly preferably over 500 bp (or nucleotides).

The use of DNA sequences, which have a high degree of identity with the endogenous sequences occurring in the plant cell and which encode cyclin SDS like proteins, is also suitable for antisense or co-suppression preparations. The minimum identity should be greater than ca. 65%, preferably greater than 80%. The use of sequences with identities of at least 90%, in particular between 95% and 100%, is to be preferred. The meaning of the term "sequence identity" is defined elsewhere herein.

Furthermore, the use of introns, i.e. of non-coding areas of genes, which code for cyclin SDS like proteins, is also conceivable for achieving an antisense or a co-suppression effect. The use of intron sequences for inhibiting the gene expression of genes, which code for starch biosynthesis proteins, has e.g. been described in the international patent applications WO97/04112, WO97/04113, WO98/37213, WO98/37214.

The person skilled in the art knows how to achieve an antisense and a co-suppression effect. For example, the method of co-suppression inhibition has been described in Jorgensen (Trends Biotechnol. 8 (1990), 340-344), Niebel et al., (Curr. Top. Microbiol. Immunol. 197 (1995), 91-103), Flavell et al. (Curr. Top. Microbiol. Immunol. 197 (1995), 43-46), Palaqui and Vaucheret (Plant. Mol. Biol. 29 (1995), 149-159), Vaucheret et al., (Mol. Gen. Genet. 248 (1995), 311-317), de Borne et al. (Mol. Gen. Genet. 243 (1994), 613-621).

The expression of ribozymes for reducing the activity of particular enzymes in cells is also known to the person skilled in the art, and is described, for example, in EP-B1 0321201. The expression of ribozymes in plant cells has been described, for example, in Feyter et al. (Mol. Gen. Genet. 250, (1996), 329-338).

The decrease of the activity of cyclin SDS like proteins in plant cells or plants according to the invention or in the method according to the invention comprising introducing a foreign nucleic acid molecule into a plant cell can also be brought about by the simultaneous expression of sense and antisense RNA molecules (RNAi technology) of the respective target gene to be repressed, preferably of the cyclin SDS like protein encoding gene.

This can be achieved, for example, by the use of chimeric constructs, which contain "inverted repeats" of the respective target gene or parts of the target gene. In this case, the generic constructs code for sense and antisense RNA molecules of the respective target gene. Sense and antisense RNA are synthesized simultaneously in planta as an RNA molecule, wherein sense and antisense RNA are separated from one another by a spacer, and are able to form a double-stranded RNA molecule.

It has been shown that the introduction of inverted repeat DNA constructs into the genome of plant cells or plants is a very effective method of repressing the genes corresponding to the inverted repeat DNA constructs (Waterhouse et al., Proc. Natl. Acad. Sci. USA 95, (1998), 13959-13964; Wang and Waterhouse, Plant Mol. Biol. 43, (2000), 67-82; Singh et al., Biochemical Society Transactions Vol. 28 part 6 (2000), 925-927; Liu et al., Biochemical Society Transactions Vol. 28 part 6 (2000), 927-929); Smith et al., (Nature 407, (2000), 319-320; international patent application WO99/53050 A1).

Sense and antisense sequences of the target gene or of the target genes can also be expressed separately from one another by means of similar or different promoters (Nap, J-P et al, 6$^{th}$ International Congress of Plant Molecular Biology, Quebec, 18-24 Jun. 2000; Poster S7-27, Presentation Session S7). The decrease of the activity of cyclin SDS like proteins in plant cells according to the invention or plants according to the invention can therefore also be achieved by producing double-stranded RNA molecules. In this regard, "inverted repeats" of DNA molecules of cyclin SDS like protein encoding genes or cDNAs are preferably introduced into the genome of plants, wherein the DNA molecules (cyclin SDS like protein encoding gene or cDNA or fragments of these genes or cDNAs) to be transcribed are under the control of a promoter, which controls the expression of said DNA molecules.

Fragments of any of the nucleic acid molecules encoding cyclin SDS like proteins are therefore also an aspect of the invention. Such fragments have various uses, e.g. as primers or probes, or they can be incorporated into transformation vectors and used to generate plants producing seedless fruits.

Such fragments of nucleic acid molecules encoding cyclin SDS like proteins may be of various sizes, e.g. at least 10 nucleotides, at least 20, at least 30, at least 40, at least 50, at least 60, at least 70, at least 80, at least 90, at least 100, at least 200, at least 300, at least 400, at least 500 nucleotides or more.

In addition to this, it is known that the formation of double-stranded RNA molecules from promoter DNA molecules in plants in trans can lead to methylation and transcriptional inactivation of homologous copies of these promoters, which are to be referred to in the following as target promoters (Mette et al., EMBO J. 19, (2000), 5194-5201). It is therefore possible to reduce the gene expression of a particular target gene (e.g. cyclin SDS like protein encoding gene), which is naturally under the control of this target promoter, by deactivating the target promoter. This means that, in this case, the DNA molecules, which include the target promoters of the genes to be repressed (target genes), in contrast to the original function of promoters in plants, are not used as control elements for the expression of genes or cDNAs, but are themselves used as transcribable DNA molecules.

For the production of double-stranded target promoter RNA molecules in planta, which can occur there as RNA hairpin molecules, constructs are preferably used, which contain the "inverted repeats" of the target promoter DNA molecules, wherein the target promoter DNA molecules are under the control of a promoter, which controls the gene expression of said target promoter DNA molecules. These constructs are subsequently introduced into the genome of plants. The expression of the "inverted repeats" of said target promoter DNA molecules in planta leads to the formation of double-stranded target promoter RNA molecules (Mette et al., EMBO J. 19, (2000), 5194-5201). The target promoter can be inactivated by this means. The decrease of the activity of cyclin SDS like proteins in plant cells according to the invention and plants according to the invention can therefore also be achieved by the introduction of double-stranded RNA molecules of promoter sequences of cyclin SDS like protein encoding genes into plant cells or plants. In this regard, "inverted repeats" of promoter DNA molecules of cyclin SDS like protein encoding genes are preferably introduced into the genome of plants, wherein the target promoter DNA molecules (promoter of a cyclin SDS like protein encoding gene) to be transcribed are under the control of a promoter, which controls the expression of said target promoter DNA molecules.

For inhibiting the expression of genes by means of the simultaneous expression of sense and antisense RNA molecules (RNAi technology), a DNA molecule can be used, for example, which includes the whole coding sequence for a cyclin SDS like protein, including any existing flanking sequences, as well as DNA molecules, which include only parts of the coding sequence, whereby these parts must be long enough to produce a so-called RNAi effect in the cells. The parts of the cyclin SDS like protein encoding gene can be chosen from coding sequences, non-translated down- or up-stream sequences, introns, promoters and/or enhancers. In general, sequences with a minimum length of 20 bp (or nucleotides), preferably a minimum length of at least 25 bp (or nucleotides), particularly preferably of at least 50 bp (or nucleotides) are suitable. For example, the DNA molecules have a length of 20 to 25 bp (or nucleotides), preferably of 26 to 50 bp (or nucleotides), particularly preferably greater than 50 bp (or nucleotides).

The use of DNA sequences, which have a high degree of identity with the endogenous sequences occurring in the plant cells and which code a cyclin SDS like protein, is also suitable for the simultaneous expression of sense and antisense RNA molecules (RNAi technology). The minimum identity should be greater than ca. 65%, preferably greater than 80%. The use of sequences with identities of at least 90%, in particular between 95% and 100%, is to be particularly preferred. Sequences, which contain successive stretches of nucleic acids sequences comprised by the nucleic acid sequence shown under SEQ ID NO 1, are particularly suitable for inhibiting cyclin SDS like protein encoding genes by means of RNAi technology.

The decrease of the activity of cyclin SDS like proteins in plant cells according to the invention and plants according to the invention or in the method according to the invention comprising introducing a foreign nucleic acid molecule into a plant cell can be achieved by so-called "in vivo mutagenesis", in which a hybrid RNA-DNA oligonucleotide ("Chimeroplast") is introduced into plant cells (Kipp, P. B. et al., Poster Session at the "5$^{th}$ International Congress of Plant Molecular Biology, 21-27 Sep. 1997, Singapore; R. A. Dixon and C. J. Arntzen, meeting report on "Metabolic Engineering in Transgenic Plants", Keystone Symposia, Copper Mountain, CO, USA, TIBTECH 15, (1997), 441-447; international patent application WO 9515972; Kren et al., Hepatology 25, (1997), 1462-1468; Cole-Strauss et al., Science 273, (1996), 1386-1389; Beetham et al., 1999, PNAS 96, 8774-8778).

A part of the DNA components of the RNA-DNA oligonucleotide is homologous to a nucleic acid sequence of an endogenous cyclin SDS like protein encoding gene, but, in comparison with the nucleic acid sequence of an endogenous cyclin SDS like protein encoding gene, it has a mutation or contains a heterologous region, which is surrounded by the homologous regions. By base pairing of the homologous regions of the RNA-DNA oligonucleotide and the endogenous nucleic acid molecule followed by homologous recombination, the mutation or heterologous region contained in the DNA components of the RNA-DNA oligonucleotide can be transferred into the genome of a plant cell. This leads to a decrease of the activity of one or more cyclin SDS like proteins.

The decrease of the activity of cyclin SDS like proteins in plant cells according to the invention and plants according to the invention or in the method according to the invention comprising introducing a foreign nucleic acid molecule into a plant cell can be achieved by introducing nucleic acid molecules encoding antagonists/inhibitors of cyclin SDS like proteins into a plant cell. The person skilled in the art knows that he can achieve a decrease of the activity of cyclin SDS like proteins by the expression of non-functional derivatives, in particular trans-dominant mutations, of such proteins, and/or by the expression of antagonists/inhibitors of such proteins. Antagonist/inhibitors of such proteins include, for example, antibodies, antibody fragments or molecules with similar bonding characteristics. For example, a cytoplasmatic scFv antibody has been used to modulate the activity of the phytochrome A protein in genetically modified tobacco plants (Owen, Bio/Technology 10 (1992), 790-4; Review: Franken, E, Teuschel, U. and Hain, R., Current Opinion in Biotechnology 8, (1997), 411-416; Whitelam, Trends Plant Sci. 1 (1996), 268-272; Conrad and Manteufel, Trends in Plant Science 6, (2001), 399-402; De Jaeger et al., Plant Molecular Biology 43, (2000), 419-428). The decrease of the activity of a branching enzyme in potato plants by expressing a specific antibody has been described by Jobling et al. (Nature Biotechnology 21, (2003), 77-80). Here, the antibody was provided with a plastid target sequence so that the inhibition of proteins localised in plastids was guaranteed.

The decrease of the activity of cyclin SDS like proteins in plant cells according to the invention and plants according to the invention or in the method according to the invention comprising introducing a foreign nucleic acid molecule into a plant cell can be achieved by introducing nucleic acid molecules comprising transposon sequences into the plant cell. Insertion of transposon sequences into the sequence of an endogenous cyclin SDS like protein encoding gene, will effect a reduction in the expression of an endogenous cyclin SDS like protein.

The transposons can be endogenous transposons (homologous to the plant) and also those that do not occur naturally in said cell (heterologous to the plant) but in each case have to be introduced into a plant cell or plant by means of genetic engineering methods, such as transformation of a cell, for example. Changing the expression of genes by means of transposons is known to the person skilled in the art. An overview of the use of endogenous and heterologous transposons as tools in plant biotechnology is presented in Ramachandran and Sundaresan (2001, Plant Physiology and Biochemistry 39, 234-252). The possibility of identifying mutations in which specific genes have been inactivated by transposon insertion mutagenesis is presented in an overview by Maes et al. (1999, Trends in Plant Science 4 (3), 90-96). The production of rice mutants with the help of endogenous transposons is described by Hirochika (2001, Current Opinion in Plant Biology 4, 118-122). The identification of maize genes with the help of endogenous retrotransposons is presented, for example, by Hanley et al. (2000, The Plant Journal 22 (4), 557-566). The possibility of manufacturing mutants with the help of retrotransposons and methods of identifying mutants are described by Kumar and Hirochika (2001, Trends in Plant Science 6 (3), 127-134). The activity of technological (artificial) transposons in different species has been described both for dicotyledonous and for monocotyledonous plants: e.g. for rice (Greco et al., 2001, Plant Physiology 125, 1175-1177; Liu et al., 1999, Molecular and General Genetics 262, 413-420; Hiroyuki et al., 1999, The Plant Journal 19 (5), 605-613; Jeon und Gynheung, 2001, Plant Science 161, 211-219), barley (2000, Koprek et al., The Plant Journal 24 (2), 253-263) *Arabidopsis thaliana* (Aarts et al., 1993, Nature 363, 715-717, Schmidt und Willmitzer, 1989, Molecular and General Genetics 220, 17-24; Altmann et al., 1992, Theoretical and Applied Genetics 84, 371-383; Tissier et al., 1999, The Plant Cell 11, 1841-1852), tomato (Belzile und Yoder, 1992, The Plant Journal 2 (2), 173-179) and potato (Frey et al., 1989, Molecular and General Genetics 217, 172-177; Knapp et al., 1988, Molecular and General Genetics 213, 285-290).

Basically, the plant cells according to the invention and the plants according to the invention can be produced both with the help of homologous and heterologous transposons.

In conjunction with the present invention, plant cells and plants according to the invention can also be produced by the use of so-called insertion mutagenesis (overview article: Thorneycroft et al., 2001, Journal of experimental Botany 52 (361), 1593-1601). The decrease of the activity of cyclin SDS like proteins in plant cells according to the invention and plants according to the invention or in the method according to the invention comprising introducing a foreign nucleic acid molecule into a plant cell can be achieved by introducing nucleic acid molecules comprising T-DNA sequences into the plant cell.

T-DNA insertion mutagenesis is based on the fact that certain sections (T-DNA) of Ti plasmids from *Agrobacterium* can integrate into the genome of plant cells. The place of integration in the plant chromosome is not defined, but can take place at any point. If the T-DNA integrates into a part of the chromosome, which constitutes a gene function, then this can lead to a change in the gene expression and thus also to a change in the activity of a protein coded by the gene concerned. In particular, the integration of a T-DNA into the coding area of a protein often leads to the corresponding protein no longer being able to be synthesized at all, or no longer synthesized in active form, by the cell concerned. The use of T-DNA insertions for producing mutants is described, for example, for *Arabidopsis thaliana* (Krysan et al., 1999, The Plant Cell 11, 2283-2290; Atipiroz-Leehan and Feldmann, 1997, Trends in genetics 13 (4), 152-156; Parinov and Sundaresan, 2000, Current Opinion in Biotechnology 11, 157-161) and rice (Jeon and An, 2001, Plant Science 161, 211-219; Jeon et al., 2000, The Plant Journal 22 (6), 561-570). Methods for identifying mutants, which have been produced with the help of T-DNA insertion mutagenesis, are described, amongst others, by Young et al., (2001, Plant Physiology 125, 513-518), Parinov et al. (1999, The Plant cell 11, 2263-2270), Thorneycroft et al. (2001, Journal of Experimental Botany 52, 1593-1601), and McKinney et al. (1995, The Plant Journal 8 (4), 613-622).

T-DNA insertion mutants have been produced in great numbers for *Arabidopsis thaliana*, for example, and are made available by different culture collections ("Stock centre", e.g. Salk Institute Genomic Analysis Laboratory, 10010 N. Torrey Pines Road, La Jolla, CA 92037, http://signal.salk.edu/).

T-DNA mutagenesis is basically suitable for the production of the plant cells and plants according to the invention, which have a decreased activity of a cyclin SDS like protein.

In conjunction with the present invention, the term "foreign nucleic acid molecule" is understood to mean such a nucleic acid molecule that either does not occur naturally in the corresponding wild type plant cells or plants, or that does not occur naturally in the concrete spatial arrangement in wild type plant cells or plants, or that is localised at a place in the genome of the plant cell or plant at which it does not occur naturally. Preferably, the foreign nucleic acid molecule is a recombinant molecule, which consists of different elements, the combination or specific spatial arrangement of which does not occur naturally in plant cells or plants.

In principle, a foreign nucleic acid molecule can be any nucleic acid molecule that effects a decrease in the activity of a cyclin SDS like protein. Such kind of nucleic acid molecules have been described herein above.

In conjunction with the present invention, the term "genome" is to be understood to mean the totality of the genetic material present in a plant cell. It is known to the person skilled in the art that, as well as the cell nucleus, other compartments (e.g. plastids, mitochondriona) also contain genetic material.

A large number of techniques are available for the introduction of DNA into a plant host cell. These techniques include the transformation of plant cells with T-DNA using *Agrobacterium tumefaciens* or *Agrobacterium rhizogenes* as the transformation medium, the fusion of protoplasts, injection of nucleic acids, the electroporation of nucleic acids, the introduction of nucleic acids by means of the biolistic approach as well as other possibilities.

The use of Agrobacteria-mediated transformation of plant cells has been intensively investigated and adequately described in EP 120516; Hoekema, I N: The Binary Plant Vector System Offsetdrukkerij Kanters B.V., Alblasserdam (1985), Chapter V; Fraley et al., Crit. Rev. Plant Sci. 4, 1-46 and by An et al. EMBO J. 4, (1985), 277-287. For the transformation of potato, see Rocha-Sosa et al., EMBO J. 8, (1989), 29-33, for example.

The transformation of monocotyledonous plants by means of vectors based on *Agrobacterium* transformation has also been described (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al, Transgenic Res. 2, (1993), 252-265). An alternative system to the transformation of monocotyledonous plants is transformation by means of the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), protoplast transformation, electroporation of partially permeabilised cells and the introduction of DNA by means of glass fibres. In particular, the transformation of maize has been described in the literature many times (cf. e.g. WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726). The successful transformation of other types of cereal has also already been described, for example for barley (Wan and Lemaux, see above; Ritala et al., see above; Krens et al., Nature 296, (1982), 72-74) and for wheat (Nehra et al., Plant J. 5, (1994), 285-297; Becker et al., 1994, Plant Journal 5, 299-307). All the above methods are suitable within the framework of the present invention. Transformation of vegetable crops is also commonly known in the art. In Curtis (2012, Springer Science & Business Media, ISBN: 1402023332, 9781402023330) besides others, methods for the transformation of coffee, pineapple, pear, radish, carrot, pea, cabbage, cauliflower and watermelon is disclosed. Transformation of vegetable crops like banana, citrus, mango, papaya, watermelon, avocado, grape, (sweet) melon, kiwifruit, coffee, cacao have been described in Pua and Davey (2007, Springer Science & Business Media, ISBN: 3540491619, 9783540491613).

For expressing nucleic acid molecules, like those conferring a gene silencing effect or being used for introducing mutations into an allele in plant cells or plants, these nucleic acid are preferably linked with regulatory DNA sequences, including those which initiate transcription in plant cells (promoters). At the same time, the promoter can be chosen so that expression takes place constitutively or only in a certain tissue, at a certain stage of the plant development or at a time determined by external influences. The promoter can be homologous or heterologous both with respect to the plant and with respect to the nucleic acid molecule. The nucleic acid molecules therefore commonly are not naturally occurring in plants but are recombinant nucleic acid molecules, meaning that the combination of different genetic elements (e.g. coding sequences, RNAi complementary sequence, promoters) comprised by the nucleic acid molecule are not present in this combination in nature.

Suitable promoters are commonly known in the art, for example, the promoter of the 35S RNA of the cauliflower mosaic virus and the ubiquitin promoter from maize for constitutive expression, the patatin promoter B33 (Rocha-Sosa et al., EMBO J. 8 (1989), 23-29) for tuber-specific expression in potatoes or a promoter, which only ensures expression in photosynthetically active tissues, e.g. the ST-LS1 promoter (Stockhaus et al., Proc. Natl. Acad. Sci. USA 84 (1987), 7943-7947; Stockhaus et al., EMBO J. 8 (1989), 2445-2451) or, for endosperm-specific expression of the HMG promoter from wheat, the USP promoter, the phaseolin promoter, promoters of zein genes from maize (Pedersen et al., Cell 29 (1982), 1015-1026; Quatroccio et al., Plant Mol. Biol. 15 (1990), 81-93), glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218) or shrunken-1 promoter (Werr et al., EMBO J. 4 (1985), 1373-1380). However, promoters can also be used, which are only activated at a time determined by external influences (see for example WO 9307279). Promoters of heat-shock proteins, which allow simple induction, can be of particular interest here. Furthermore, seed-specific promoters can be used, such as the USP promoter from *Vicia faba*, which guarantees seed-specific expression in *Vicia faba* and other plants (Fiedler et al., Plant Mol. Biol. 22 (1993), 669-679; Baumlein et al., Mol. Gen. Genet. 225 (1991), 459-467).

The recombinant nucleic acid molecule may also contain a termination sequence (polyadenylation signal), which is used for adding a poly-A tail to the transcript. A function in the stabilisation of the transcripts is ascribed to the poly-A tail. Elements of this type are described in the literature (cf. Gielen et al., EMBO J. 8 (1989), 23-29) and can be exchanged at will.

Intron sequences can also be present, e.g. between the promoter and the coding region. Such intron sequences can lead to stability of expression and to increased expression in plants (Callis et al., 1987, Genes Devel. 1, 1183-1200; Luehrsen, and Walbot, 1991, Mol. Gen. Genet. 225, 81-93; Rethmeier, et al., 1997; Plant Journal. 12(4): 895-899; Rose and Beliakoff, 2000, Plant Physiol. 122 (2), 535-542; Vasil et al., 1989, Plant Physiol. 91, 1575-1579; XU et al., 2003, Science in China Series C Vol. 46 No. 6, 561-569). Suitable intron sequences are, for example, the first intron of the sh1 gene from maize, the first intron of the polyubiquitin gene 1 from maize, the first intron of the epsps gene from rice or one of the two first introns of the PAT1 gene from *Arabidopsis*.

What has been described herein concerning the verification if a plant has a mutation in a nucleic acid sequence or a gene or allele encoding a cyclin SDS like protein and for growing/cultivating the plants for the method for producing a plant according to the invention is also applicable here for the method comprising introducing a foreign nucleic acid molecule into a plant cell according to the invention.

In a further embodiment of the present invention the methods for producing a plant according to the invention and the method according to the invention comprising introducing a foreign nucleic acid molecule into a plant cell comprise a further step consisting of the production of further plants from the plants obtained from step d) in each of the methods according to the invention. The further plants produced are characterised in that they comprise at least one mutant allele of a cyclin SDS like protein encoding gene or that they have a decreased activity of a cyclin SDS like protein due to the introduction of a foreign nucleic acid molecule as described herein above. These further plants can be produced by means of vegetative (agamic) or generative (gamic, sexual) reproduction. Suitable for vegetative propagation are, for example, cuttings, in vitro tissue, cell, protoplast, embryo or callus cultures, micropropagation, rhizomes or tubers. Other propagation material includes, for example, fruits, seeds, seedlings, being heterozygous or homozygous for a mutant allele of a cyclin SDS like protein encoding genes, etc.

Techniques for vegetative (agamic) propagation, including micropropagation of plants are well known in the art and e.g. described for banana, citrus, mango, papaya, avocado, (sweet) melon, have been described in Pua and Davey (2007, Springer Science & Business Media, ISBN: 3540491619, 9783540491613). Sultana and Rhaman (2012, LAP Lambert Academic Publishing, ISBN-13: 978-3-8484-3937-9) e.g. disclose various tissue culture and micropropagation methods for watermelon.

Plants obtainable/obtained by a method according to the invention comprising introducing a foreign nucleic acid molecule into a plant cell, are also an embodiment of the invention.

A further embodiment of the invention concerns a method for propagating seedless fruit producing plants comprising the steps of a) obtaining seeds from which a plant according to the invention grows or obtaining seeds deposited under accession No. NCIMB 42532 or progeny thereof, b) growing plants from the seeds obtained in step a), c) selecting seedless fruit producing plants from the plants grown under step b), d) propagating the plants selected under step c) by a method selected from the group consisting of i) grafting of parts of plants selected under step c) to another rootstock, ii) cultivating parts of plants selected under step c) in in vitro tissue culture and optionally regenerating new plants from the tissue culture, iii) optionally producing embryo or callus cultures from parts of plants selected under step c) and optionally regenerating new plants from the tissue culture, iv) optionally producing further plants by micropropagation techniques.

Propagation of plant parts by grafting and propagation and optionally regeneration of plants by tissue culture methods are well known in the art. Such methods are described in various scientific publications and are reviewed and summarized in a number of scientific books, like e.g. Smith (2012, Academic Press, ISBN-13: 978-0124159204), Gayatri & Kavyashree (2015, Alpha Science International Ltd, ISBN-13: 978-1842659618) etc. For watermelon, respective methods are described e.g. by Sultana and Rhaman (2012, LAP Lambert Academic Publishing, ISBN-13: 978-3848439379).

Plants or plant parts obtainable/obtained by methods for propagating seedless fruit producing plants according to the invention are also an embodiment of the invention.

In a further embodiment of the invention, all methods for producing a plant according to the invention or optionally the methods for propagating seedless fruit producing plants according to the invention disclosed herein are used for producing a plant according to the invention.

A further embodiment of the invention concerns propagation material of plants according to the invention, and/or propagation material of plants comprising plant cells according to the invention or propagation material of plants obtainable/obtained by a method according to the invention for production of a plant or propagation material of plants obtainable/obtained by a method according to the invention comprising introducing a foreign nucleic acid molecule into a plant cell or propagation material of plants obtainable/obtained from a plant optionally obtainable by a method for propagating seedless fruit producing plants according to the invention. A specific comprised embodiment of the invention is propagation material of plants obtainable/obtained from seeds deposited under accession number NCIMB 42532, preferably propagation material of plants obtainable/obtained from seeds deposited under accession number NCIMB 42532 being heterozygous or homozygous for the mutant allele of a cyclin SDS like protein encoding gene. Also comprised by the invention is propagation material of plants heterozygous or homozygous for a mutant allele of a cyclin SDS like protein encoding gene, wherein the propagation material is obtained/obtainable from plants originating from a crossing of a plant obtained from seeds of deposit accession number NCIMB 42532 with another plant.

Here, the term "propagation material" comprises those components of the plant which are suitable for generating progeny via the vegetative (agamic) or generative (gamic, sexual) route. Suitable for vegetative propagation are, for example, cuttings, in vitro tissue, cell, protoplast, embryo or callus cultures, micropropagation methods, rhizomes or tubers. Other propagation material includes, for example, fruits, seeds, seedling, being heterozygous for a mutant allele of a cyclin SDS like protein encoding gene etc. The propagation material in one aspect takes the form of cuttings which are propagated, e.g. by grafting to another rootstock, or in vitro tissue culture material, in particular embryo cultures. In particular preferred is propagation material in the form of in vitro tissue culture material, particularly in vitro embryo cultures. A plant produced by vegetative propagation is herein also referred to as a vegetatively propagated plant. Especially plants in which the mutant cyclin SDS like allele is present in homozygous form are preferably propagated vegetatively (as their fruits are seedless).

A further embodiment of the invention concerns parts of plants according to the invention, and/or parts of plants comprising plant cells according to the invention or parts of plants obtainable/obtained by a method according to the invention for production of a plant or parts of plants obtainable/obtained by a method according to the invention comprising introducing a foreign nucleic acid molecule into a plant cell or parts of plants obtainable/obtained from a plant optionally obtainable by a method for propagating seedless fruit producing plants according to the invention. A further comprised embodiment of the invention concerns parts of plants obtainable/obtained from seeds deposited under accession number NCIMB 42532 (or from progeny thereof), preferably plant parts of plants obtainable/obtained from seeds deposited under accession number NCIMB 42532 (or from progeny thereof) being heterozygous or homozygous for the mutant allele of a cyclin SDS like protein encoding gene. Also comprised by the invention are plant parts of plants heterozygous or homozygous for a mutant allele of a cyclin SDS like protein encoding gene, wherein the plant parts are obtained/obtainable from plants originating from a crossing of a plant obtained from seeds of deposit accession number NCIMB 42532 with another plant.

A further embodiment of the invention concerns a method for production of a seedless fruit comprising growing a plant according to the invention and/or growing a plant comprising plant cells according to the invention or growing a plant obtainable/obtained by a method for production of a plant according to the invention or growing fruits of plants obtainable/obtained by a method according to the invention comprising introducing a foreign nucleic acid molecule into a plant cell or growing a plant obtainable/obtained from a plant optionally obtained/obtainable by method for propagating seedless fruit producing plants according to the invention in a field or in a greenhouse (e.g. a glasshouse, tunnel or net-house), allowing the plant to be pollinated and harvesting the seedless fruit. Preferably the plant grown in the method for producing seedless fruits according to the invention is homozygous for a mutant allele of a cyclin SDS like protein encoding gene.

It has been surprisingly found that pollination of plants comprising a mutant allele of a cyclin SDS like protein encoding gene in homozygous state with pollen from a different plant will result in the plant to produce seedless fruits. It is not decisive if the stigma of a plant being homozygous for a mutant allele of a cyclin SDS like protein encoding gene is pollinated by pollen comprising a mutant allele of a cyclin SDS like protein encoding gene or by pollen comprising a wild type allele of a cyclin SDS like protein encoding gene. In any case, independent of the genotype of the pollen, the female plant being homozygous for a mutant allele of a cyclin SDS like protein encoding gene will produce seedless fruits. Even when cross-pollinated by pollen from wild type plants, plants according to the invention being homozygous for a mutant allele of a cyclin SDS like protein encoding gene will produce seedless fruits. Thus, when cultivating plants according to the invention, in any case seedless fruits will be obtained.

"Greenhouse" shall be understood in connection with the present invention to mean a building or compartment used for growing plants which has a roof and walls of transparent material consisting of glass, plastic, polyethylene, gaze, netting or the like. Greenhouses may have or not have further technical equipment for heating, cooling, shading, automatic watering, fertilisation, carbon dioxide concentration adjustment etc. Greenhouses with any type of technical equipment shall be comprised by the term "greenhouse" as used herein.

Another embodiment of the invention concerns fruits of or obtainable/obtained from plants according to the invention, and/or fruits comprising plant cells according to the invention or fruits of plants obtainable/obtained by a method according to the invention for production of a plant or fruits of plants obtainable/obtained by a method according to the invention comprising introducing a foreign nucleic acid molecule into a plant cell or fruits of plants obtainable/obtained from a plant obtained/obtainable by a method according to the invention for propagating seedless fruit producing plants or a fruit obtainable/obtained by a method according to the invention for production of a seedless fruit. A further comprised embodiment of the invention concerns fruits of plants obtainable/obtained from seeds deposited under accession number NCIMB 42532 (or progeny thereof), preferably fruits of plants obtainable/obtained from seeds deposited under accession number NCIMB 42532 (or progeny thereof) being heterozygous or homozygous for the mutant allele of a cyclin SDS like protein encoding gene. Also comprised by the invention are fruits heterozygous or homozygous for a mutant allele of a cyclin SDS like protein encoding gene, wherein the fruits are obtained/obtainable from plants originating from a crossing of a plant obtained from seeds of deposit accession number NCIMB 42532 with another plant. The fruits can be heterozygous for a mutant allele of a cyclin SDS like protein encoding gene and produce seed bearing fruits or can be homozygous for an allele of a cyclin SDS like protein encoding gene and produce seedless fruits. Fruits being heterozygous for an allele of a cyclin SDS like protein encoding gene can be used for propagating plants comprising a mutant allele of a cyclin SDS like protein encoding gene. Preferably, the fruits according to the invention are homozygous for a mutant allele of a cyclin SDS like protein encoding gene and/or produce seedless fruits. Seedless fruits for logical reasons are not eligible for growing further plants from these fruits. Therefore, one embodiment of the invention concerns fruit according to the invention which is a seedless fruit which is not eligible for propagation or which cannot propagate or which is a non-propagating.

A further embodiment of the invention concerns the use of a nucleic acid molecule encoding a cyclin SDS like protein selected from the group consisting of a) Nucleic acid molecules, which encode a protein with the amino acid sequence given under SEQ ID NO 2 or SEQ ID NO 4 or SEQ ID NO 6 or SEQ ID NO 12 or SEQ ID NO 19 or SEQ ID NO 20, b) Nucleic acid molecules, which encode a protein, the sequence of which has an identity of at least 58% or at least 60%, preferably at least 70%, more preferably at least 80%, even further preferred at least 90% or particularly preferred at least 95% with the amino acid sequence given under SEQ ID NO 2 or SEQ ID NO 4 or SEQ ID NO 6 or SEQ ID NO 12 or SEQ ID NO 19 or SEQ ID NO 20;

c) Nucleic acid molecules, which comprise the nucleotide sequence shown under SEQ ID NO 1 or SEQ ID NO 3 or SEQ ID NO 5 or SEQ ID NO 17 or a complimentary sequence;

d) Nucleic acid molecules, which have an identity of at least 58% or at least 60%, preferably at least 70%, more preferably at least 80%, even further preferred at least 90% or particularly preferred at least 95% with the nucleic acid sequences described under c);

e) Nucleic acid molecules, which hybridize with at least one strand of the nucleic acid molecules described under a), b), c), or d) under stringent conditions;

f) Nucleic acid molecules, the nucleotide sequence of which deviates from the sequence of the nucleic acid molecules identified under a) or b) due to the degeneration of the genetic code; and g) Nucleic acid molecules, which represent fragments, allelic variants and/or derivatives of the nucleic acid molecules identified under a), b), c) or d) for the production of a plant producing seedless fruits.

In a preferred embodiment of the use of a nucleic acid molecule encoding a cyclin SDS like protein, the nucleic acid molecule encoding a cyclin SDS like protein is used for the production of plants according to the invention, in a particular preferred embodiment, the use of a nucleic acid molecule encoding a cyclin SDS like protein is used for production of plants producing seedless fruits according to the invention.

In another preferred embodiments, a nucleic acid molecule encoding a cyclin SDS like protein is used for the production of a plant part according to the invention or a fruit according to the invention.

In a further preferred embodiment a nucleic acid molecule encoding a cyclin SDS like protein, is used in any of the methods of the invention disclosed herein. The nucleic acid molecules encoding a cyclin SDS like protein can e.g. be used in a method according to the invention for production of a plant or in a method according to the invention comprising introducing a foreign nucleic acid molecule into a plant cell or in a method according to the invention for propagating seedless fruit producing plants according to the invention or in a method according to the invention for production of a seedless fruit.

In another preferred embodiment, a nucleic acid molecule encoding a cyclin SDS like protein is used for identifying if a plant cell or plant comprises a mutant allele of a cyclin SDS like protein encoding gene or if a plant cell or plant synthesises a mutant mRNA encoding a cyclin SDS like protein or if a plant cell or plant has a decreased activity of a cyclin SDS like protein. Preferably the nucleic acid molecule encoding a cyclin SDS like protein is used for identifying if a seedless fruit producing plant comprises a mutant allele of a cyclin SDS like protein encoding gene or if a plant synthesises a mutant mRNA encoding a cyclin SDS like protein or if a plant has a decreased activity of a cyclin SDS like protein. How such plants can be identified has been described herein above and is applicable hereto accordingly.

Preferred embodiments concerning nucleic acid molecules encoding cyclin SDS like proteins have been described herein above and are applicable for the uses according to the invention accordingly.

In one aspect a screening method for identifying and/or selecting seeds, plants or plant parts or DNA from such seeds, plants or plant parts comprising in their genome a mutant allele of a cyclin SDS like protein encoding gene is provided.

The method comprises screening at the DNA, RNA (or cDNA) or protein level using known methods, in order to detect the presence of the mutant allele. There are many methods to detect the presence of a mutant allele of a gene.

For example if there is a single nucleotide difference (single nucleotide polymorphism, SNP) between the wild type and the mutant allele, a SNP genotyping assay can be used to detect whether a plant or plant part or cell comprises the wild type nucleotide or the mutant nucleotide in its genome. For example the SNP can easily be detected using a KASP-assay (see world wide web at kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p 097-1098 for KASP-assay method.

Equally other genotyping assays can be used. For example, a TaqMan SNP genotyping assay, a High Resolution Melting (HRM) assay, SNP-genotyping arrays (e.g. Fluidigm, Illumina, etc.) or DNA sequencing may equally be used.

Genotyping of diploid plants or plant parts (cells, leaves, DNA, etc.) can distinguish SNP genotypes, e.g. plants or parts comprising CC for nucleotide 1687 of SEQ ID NO: 1 (homozygous for the wild type nucleotide) can be distinguished from plants or parts comprising CT for nucleotide 1687 of SEQ ID NO: 1 (heterozygous for the mutant nucleotide) in their genome. Genotyping of tetraploid plants or plant parts (cells, leaves, DNA, etc.) can be done in the same way as for diploids, using for example a KASP-assay to distinguish SNP genotypes, e.g. plants or parts comprising CCCC for nucleotide 1687 of SEQ ID NO: 1 (homozygous for the wild type nucleotide) can be distinguished from plants or parts comprising other genotypes for the SNP, e.g. CCCA, CCAA, etc. in their genome. The same applies for triploids. The same also applies for other polyploids.

In a preferred aspect the above methods, plants, plant cells and plant parts which comprise at least one copy of a mutant allele of a cyclin SDS like protein encoding gene, are watermelon plants, especially cultivated watermelon, e.g. diploid, tetraploid or triploid cultivated watermelon.

The watermelon plants may be breeding lines or varieties. The mutant allele of a cyclin SDS like protein encoding gene may be generated in, or introduced into (e.g. from seeds deposited under NCIMB42532 or progeny thereof), any cultivated watermelon to produce lines or varieties comprising the mutant allele of the SDS like protein, preferably in homozygous form. Cultivated watermelons produce diverse fruit sizes (e.g. very small, as described in WO2012069539, e.g. less than 0.9 kg or even equal to or less than 0.65 kg; personal-size of about 3-7 pounds, i.e. about 1.4 to 3.2 kg; icebox sizes of about 6-12 pounds, i.e. about 2.7 to 5.5 kg; and larger sizes of up to 35 pounds, i.e. about 15.9 kg), fruit flesh colors, and fruit shapes and with different rind colors. The mutant allele may, therefore, be introduced into cultivated watermelon producing any fruit shape (e.g. elongate, oval, oval elongated, blocky, blocky elongated, spherical or round), fruit surface (e.g. furrow, smooth), flesh color (e.g. red, dark red, scarlet red, coral red, orange, salmon or pink, yellow, canary yellow or white), rind color (e.g. light green; dark green; green-striped with narrow, medium or wide stripes; grey types; with or without spotting; Golden yellow; Crimson type rind, Jubilee type rind; Allsweet type rind; black/dark green), rind thickness, rind toughness, rind pattern (e.g. striped, non-striped, netted), flesh structure/flesh firmness, lycopene and/or vitamin content, different sugar to acid ratios, very good fruit flavour, etc. by breeding. See Guner and Wehner 2004, Hort Science 39(6): 1175-1182, in particular pages 1180-1181 describing genes for fruit characteristics. Generally important breeding objectives are early maturity, high fruit yield, high internal fruit quality (good uniform color, high sugar, proper sugar:acid ratio, good flavour, high vitamin and lycopene content, firm flesh texture, non-fibrous flesh texture, freedom from defects such as hollow heart, rind necrosis, blossom-end rot or cross stitch and good rind characteristics and cracking-resistance). The fruits produced by the line or variety are preferably marketable fruits. In one aspect the average brix is at least 6.0, 7.0, 8.0 or at least 9.0, preferably at least 10.0, more preferably at least 11.0 or more.

Fruit color may be any color, such as red, dark red, scarlet red, coral red, orange, salmon, pink, pinkish red, yellow, canary yellow or white. Preferably the fruit flesh color is uniform.

DEPOSIT INFORMATION

Diploid *Citrullus lanatus* seeds of plants segregating for a mutant allele of a cyclin SDS like protein encoding gene have been deposited by Nunhems B.V. under the Budapest Treaty under accession No. NCIMB 42532 at the NCIMB Ltd., Bucksburn Aberdeen AB21 9YA, Scotland on 27 Jan. 2016. For the seed deposit the allele of the cyclin SDS like protein encoding gene was designated emb1. The Expert solution applies.

The deposited seeds were obtained from a self-pollinated back-cross of a plant homozygous for the emb1 mutant allele with plants homozygous for the emb1 wild type allele. Therefore 25% of the deposited seeds are homozygous for the emb1 mutant allele and produce seedless fruits, 50% are heterozygous for the mutant allele and 25% are homozygous for the wild type allele, encoding the wild type cyclin SDS like protein.

Access to the deposits will be available during the pendency of this application to persons determined by the Commissioner of Patent and Trademarks to be entitled thereto upon request.

Subject to 37 C.F.R. § 1.808(b), all restrictions imposed by the depositor on the availability to the public of one or more deposits will be irrevocably removed upon the granting of the patent by affording access to the deposits. The deposits will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

SEQUENCE DESCRIPTION

SEQ ID NO 1: Genomic sequence of a wild type cyclin SDS like protein encoding gene from *Citrullus lanatus*.

SEQ ID NO 2: Amino acid sequence of a SDS like protein from *Citrullus lanatus*. The amino acid sequence is derivable from the coding sequence of SEQ ID NO 1.

SEQ ID NO 3: mRNA sequence of a mutant allele of a cyclin SDS like protein from *Citrullus lanatus*.

SEQ ID NO 4: Amino acid sequence of the mutant allele of a SDS like protein. The amino acid sequence is derivable from SEQ ID NO 3.

SEQ ID NO 5: Nucleic acid sequence of a wild type cyclin SDS like protein encoding gene from *Cucumis melo*.

SEQ ID NO 6: Amino acid sequence of a SDS like protein from *Cucumis melo*. The amino acid sequence is derivable from the coding sequence of SEQ ID NO 5.

SEQ ID NO 7: Artificial sequence used as primer (A4532) in PCR and\or sequencing reactions.

SEQ ID NO 8: Artificial sequence used as primer (A4533) in PCR and\or sequencing reactions.

SEQ ID NO 9: Artificial sequence used as primer (A4534) in PCR and\or sequencing reactions.

SEQ ID NO 10: Artificial sequence used as primer (A4535) in PCR and\or sequencing reactions.

SEQ ID NO 11: Artificial sequence used as primer (A4538) in PCR and\or sequencing reactions.

SEQ ID NO 12: Amino acid sequence of a SDS like protein from *Cucumis sativus*.

SEQ ID NO 13: sequence of sample 114 and 115 of FIG. 2

SEQ ID NO 14: sequence of sample 114 and 115 of FIG. 2

SEQ ID NO 15: sequence of sample 116 and 117 of FIG. 2

SEQ ID NO 16: sequence of sample 116 and 117 of FIG. 2

SEQ ID NO 17: cDNA sequence of a watermelon mutant cyclin SDS like gene comprising a C to T mutation at nucleotide 670 resulting in a stop codon at nucleotide 670 to 671

SEQ ID NO 18: watermelon mutant cyclin SDS like protein encoded by the cDNA of SEQ ID NO 17

SEQ ID NO 19: Amino acid sequence of a wild type SDS like protein from *Solanum lycopersicum*

SEQ ID NO 20: Amino acid sequence of a wild type SDS like protein from *Capsicum annuum*

GENERAL METHODS

1. Isolation of RNA

Figure 1:
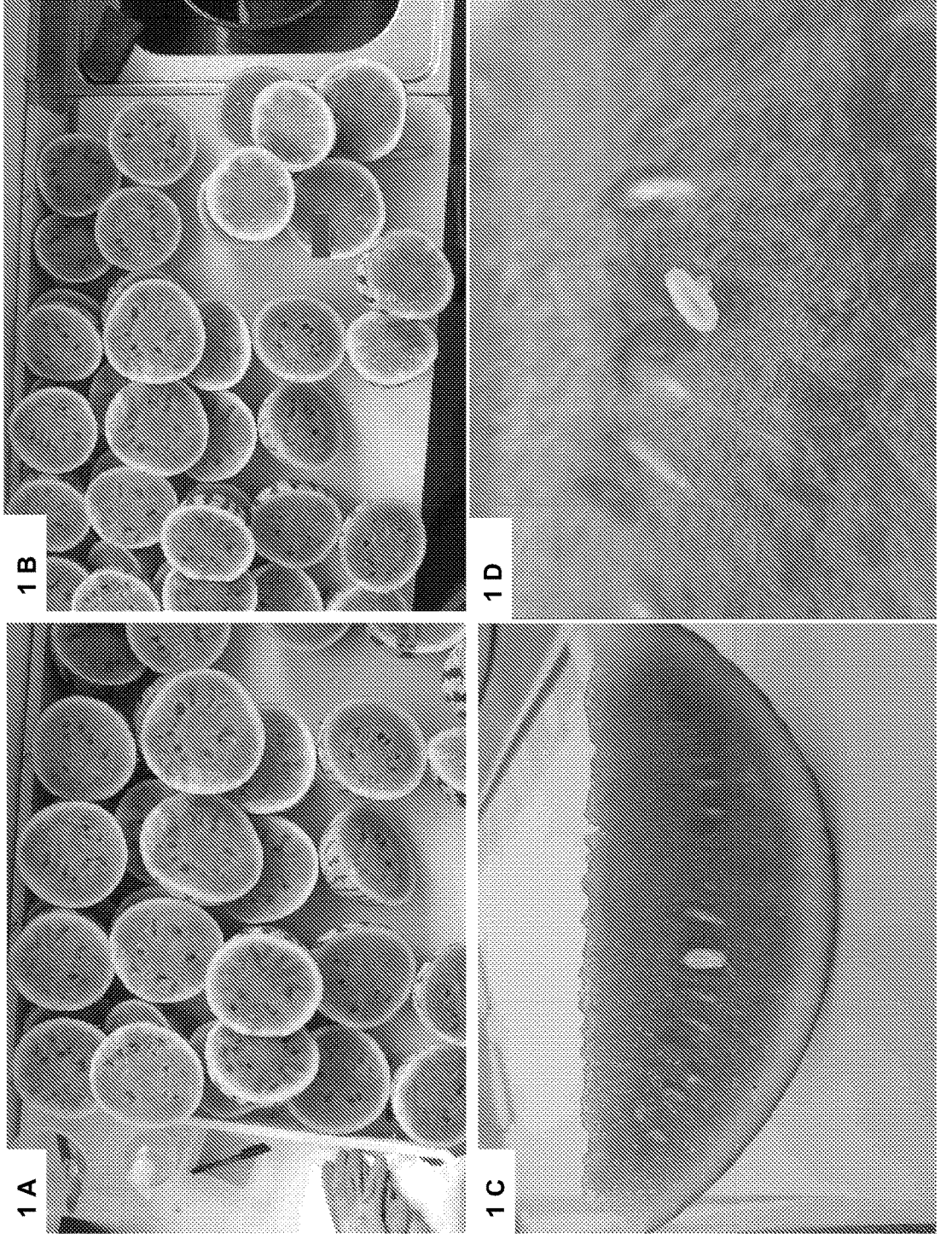
FIG. 1 Watermelon fruits from wild type plants (1A), wild type plants compared to fruits from EMB1 mutant plants (1B), slice of seedless fruit from an EMB1 mutant plant (IC) and opened embryoless seed of an EMB1 mutant plant (1D).

Young ovary tissue was cut into small pieces, frozen in liquid nitrogen and stored at −80° C. until further use. The frozen tissue pieces were ground into powder with piston and mortar in liquid nitrogen to keep the powder frozen. 100 mg of the powder was used to isolate total RNA using a plant RNA isolation kit according to the manufacturer's protocol (RNeasy Plant Mini Kit, Qiagen).

2. Preparation of cDNA The RNA was treated with DNase (TURBODNA-free, Ambion) and 0.9 g RNA was used for reverse transcription according to the manufacturer's protocols (iScript cDNA Synthesiskit, BioRad).

3. PCR on cDNA

PCR took place in a total volume of 20 μl of buffer (Phire reaction buffer, Thermo Fisher Scientific) containing 0.2 mM dNTP's, 0.4 μl Phire Hot Start II DNA Polymerase (Thermo Fisher Scientific), 0.25 μM of each primer and 0.4 μl cDNA mix. After initial denaturation step of 30 minutes at 90° C., 40 cycles of 10 seconds at 98° C., 15 seconds at 60° C. and 30 seconds at 72° C. were performed and the reaction was finalized with 3 minutes at 72° C.

4. Sequencing

The PCR product size was analysed using QIAxcel Advanced System (Qiagen) and the PCR reaction mixture was sent to a service provider to be sequenced (BaseClear, NL).

EXAMPLES

1. Isolation of Seedless Fruit Mutant

A mutant population was established by treating approximately 10.000 watermelon seeds from an inbred line (WMZD0048TYY, abbreviated TYY in the following) with EMS several hours and subsequently washing the seeds in streaming tap water for 30 minutes. After that the seeds were kept wet until sowing in soil. M1 Plants were grown from the mutagenized seeds, self-pollinated and the seeds (M2 generation) were harvested. Eight seeds from each of 3000 M2 families were sown grown and mutant plants producing seedless fruits were isolated. One of these mutant plants was designated EMB1. Propagation of the EMB1 mutant plant was performed by grafting cuttings of the EMB1 mutant plant to rootstock of a non-mutagenized watermelon plants.

2. Confirmation of Seedless Fruit Phenotype

The EMB1 mutant was back-crossed with the original non-mutagenized watermelon TYY inbred line, using pollen from the EMB1 mutant (BC1 generation). 25% of the plants grown from the self-pollinated BC1 generation did produce seedless fruits.

Pollen from the EMB1 mutant was also used for crossing with different watermelon inbred lines for establishing a mapping population. 25% of self-pollinated plants of the mapping population produced seedless fruits.

The results from the respective back-crosses and crosses wherein pollen from the EMB1 mutant was used to fertilise other inbred lines clearly demonstrate that pollen of the EMB1 mutant is fertile.

In further crosses EMB1 mutant plants, homozygous for the emb1 mutant allele were used as female parent and pollinated with pollen from various different other lines. 100% of plants from each of these crosses produced seedless fruits.

Results obtained from the different crossings show that the emb1 mutation is due to a single recessive allele. The results also demonstrate that the seedless fruit phenotype is maintained when pollen form seed producing plants is used to fertilise EMB1 mutant plants. The seedless fruit phenotype therefore is not due to aberrant pollen of the EMB1 mutant but can be assigned to defects in embryo development.

3. Identification of the Gene Causing the Seedless Fruit Phenotype

The mapping population established by pollinizing different watermelon inbred lines with pollen from the EMB1 mutant plant was analysed and a single nuclear polymorphism (SNP) was detected in the genomic sequence shown under SEQ ID NO 1. SEQ ID NO 1 shows the sequence of the wild type allele. In the respective allele of the EMB1 mutant plant the nucleotide guanine (G) at position number 2185 in SEQ ID NO 1 is replaced by adenine (A).

4. Analysis of mRNA Transcribed from Emb1 Alleles

Flower buds of different size were harvested from field grown plants. Sample Numbers 114 and 115 are flower buds from plants of the original inbred line, designated TYY, which was used for mutagenesis. TYY thus represent wild type plants comprising wild type emb1 alleles. Sample Numbers 115 and 116 are flower buds from seedless fruit producing EMB1 mutant plants comprising mutant emb1 alleles. An overview of phenotypes, material harvested and analysed for respective Sample Numbers is given in Table 1.

TABLE 1

| Sample Number | Plant Sample Name | Tissue collected | Phenotype |
|---|---|---|---|
| 114 | TYY (101) | Flower bud 1 mm | Wild type seed bearing fruit |
| 115 | TYY (102) | Flower bud 3-4 mm | Wild type seed bearing fruit |
| 116 | EMB1 (103) | Flower bud 1 mm | Seedless fruit |
| 117 | EMB1 (104) | Flower bud 3-4 mm | Seedless fruit |

Figure 3:
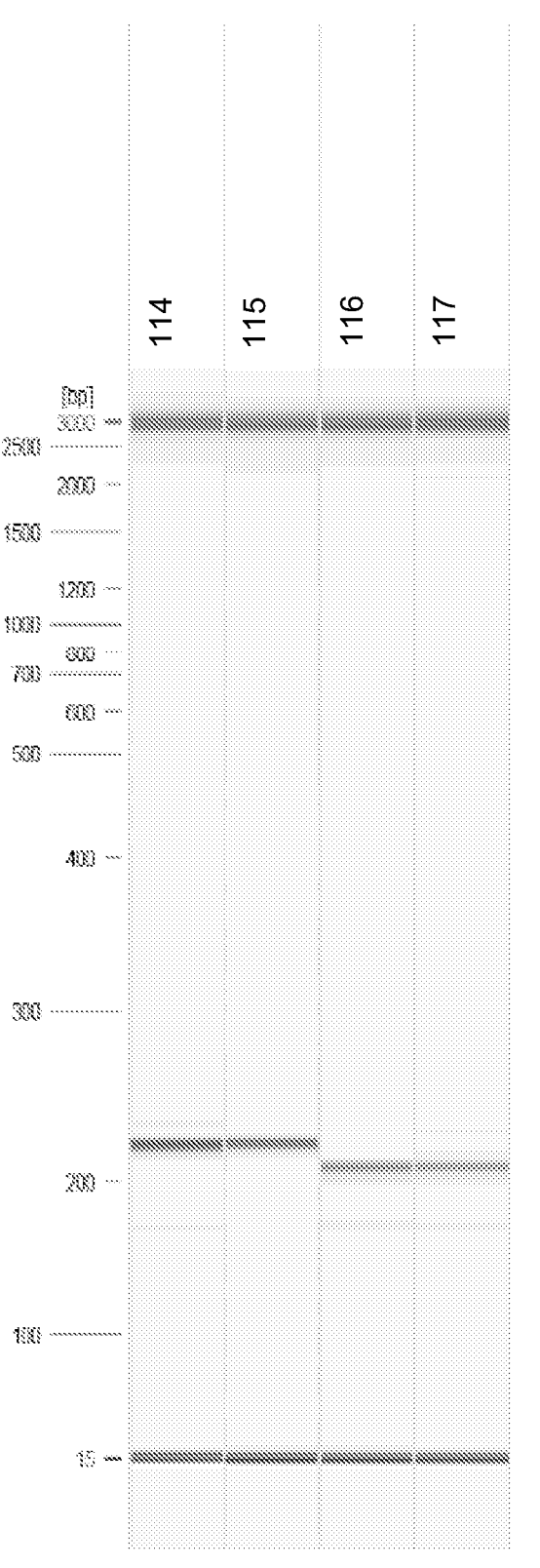
FIG. 3 Electrophoretic analysis of the PCR products obtained from cDNA of Sample Numbers 114, 115, 116 and 117 on a polyacrylamide gel. Sample Numbers 114 and 115 are obtained from wild type plants. Sample Numbers 116 and 117 are obtained from EMB1 mutant plants.

RNA was isolated from the flower buds of the different Sample numbers. 700 ng RNA for each of the Sample numbers was used for cDNA synthesis. A PCR reaction using primers A4532 (SEQ ID NO 7) and A4533 (SEQ ID NO 8) was performed on each of the cDNA samples obtained. The primers were designed to amplify a part of the emb1 allele of the coding sequence indicated in SEQ ID NO 1. The PCR products were analysed on a polyacrylamide gel which is shown in FIG. 3. From FIG. 3 it is clearly derivable, that Sample numbers 116 and 117 did result a shorter PCR fragment than all the other Sample numbers. This clearly indicated that the mRNA of the emb1 mutant allele comprises a deletion of nucleotides compared to the corresponding wild type allele in Sample numbers 114 and 115.

Figure 2:
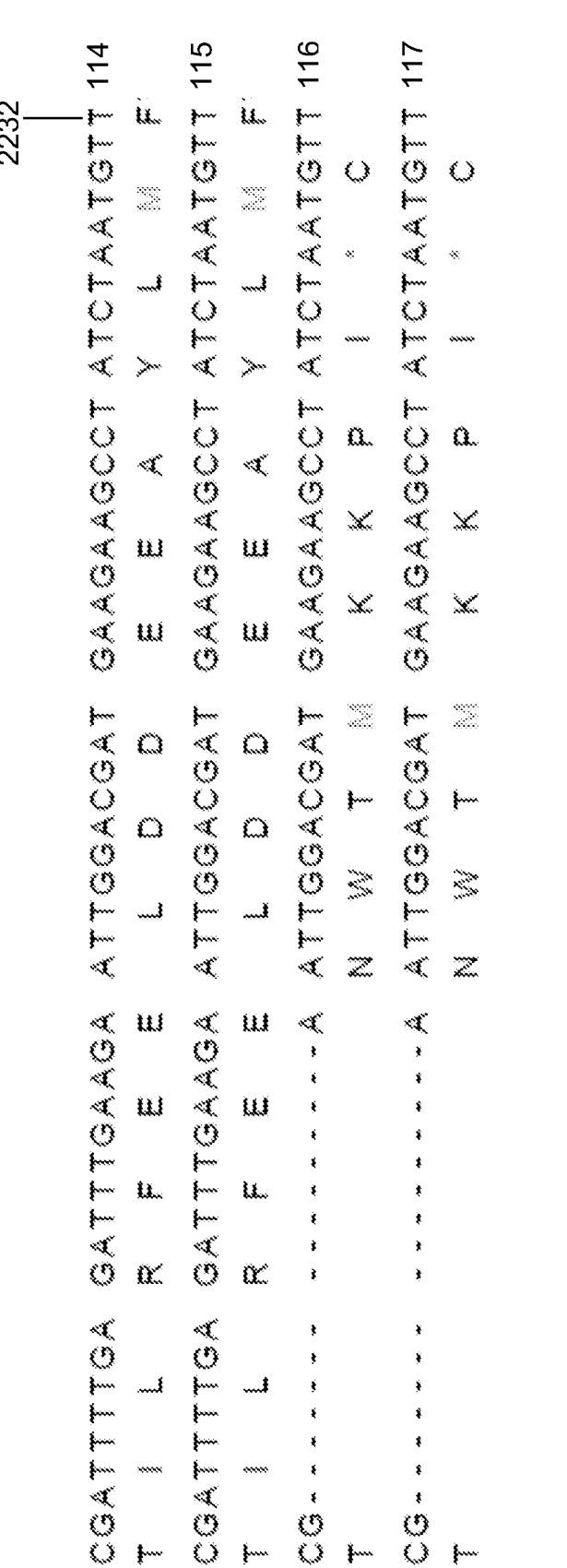
FIG. 2 Sequence alignment comparing the sequences obtained for Sample Numbers 114, 115, 116 and 117. The number in the top right side indicates the nucleotide position in the corresponding sequence shown under SEQ NO 1. Sample Numbers 116 and 117 are obtained from EMB1 mutant plants. Sample Numbers 114 and 115 are obtained from wild type plants.

5. cDNA Sequence Analysis of Emb1 Alleles cDNA of Sample Numbers 114, 115, 116 and 117 were sequenced using primer A4532 shown under SEQ ID NO 7, primer A4538 shown under SEQ ID NO 11, primer A4534 SEQ ID NO 9 and primer A4535 SEQ ID NO 10. The sequences obtained from each of Sample Numbers 116 and 117 is shown under SEQ ID NO 3 as mRNA molecule. The sequences obtained from each of Sample Numbers 114 and 115 is identical to the coding sequence indicated in SEQ ID NO 1. Comparison of the sequences obtained from Sample Numbers 114, 115, 116 and 117 showed that the sequences of each of Sample Number 116 and 117 has a deletion of 16 consecutive nucleotides compared to the sequences of each of Sample Number 114 and 115. In addition, sequences of each of Sample Number 116 and 117 have a frame shift which causes a pre-mature stop codon in the coding sequence, compared to the sequences of each of Sample Number 114 and 115. An alignment of the sequence parts concerned is shown in FIG. 2.

It is concluded, that the emb1 mutant allele of Sample Numbers 116 and 117 is transcribed into an mRNA which has a deletion, a frame shift in the reading frame and a pre-mature stop codon compared to mRNA transcribed from the wild type allele of Sample Numbers 114 and 115. In addition, it can be seen from FIG. 2 that the mRNA transcribed from the emb1 mutant allele of Sample Numbers 116 and 117 encodes a protein wherein 8 amino acids are exchanged compared to protein encoded by the mRNA transcribed from the wild type allele of Sample Numbers 114 and 115.

6. Generation of Another Watermelon Mutant Plant

Knowing the cyclin SDS like gene sequence made it possible to generate other mutant alleles in the SDS like gene. The EMS mutagenized TILLING population was screened with primers designed on a domain in which EMS mutations could convert an amino acid encoding codon into a stop codon.

```
Forward primer:
                              (SEQ ID NO: 21)
CGAAGAGAAAGGATTAGACGTTG Reverse primer:
                              (SEQ ID NO: 22)
TCTGAGCAGTCAGTATCAGACG
```

A plant was identified comprising a mutant cyclin SDS like allele. The identified allele comprises a single nucleotide replacement at nucleotide 1687 of SEQ ID NO: 1, leading to a stop codon. The mutant allele thus encodes a truncated cyclin SDS like protein comprising only amino acids 1 to 223 of the wild type protein of SEQ ID NO: 2. The cDNA of the mutant allele is provided in SEQ ID NO: 17 and the truncated protein encoded by the mutant allele is provided in SEQ ID NO: 18.

SEQUENCE LISTING

Sequence total quantity: 22
SEQ ID NO: 1          moltype = DNA  length = 5135

```
FEATURE                 Location/Qualifiers
source                  1..5135
                        mol_type = genomic DNA
                        organism = Citrullus lanatus
exon                    1018..2088
intron                  2089..2185
exon                    2186..2353
intron                  2354..3098
exon                    3099..3265
intron                  3266..4324
exon                    4325..4607
CDS                     join(1018..2088,2186..2353,3099..3265,4325..4604)
                        note = The CDS-derived contiguous protein, which was shown
                         below the DNA in the original St25 listing in form of four
                         protein segments, is given by Seq-ID 2
                        protein_id = 2
                        translation = MKSKKPRANPKPESYSPPKKKLRSQLPRRRRSRISPFFCSLDSDSP
                        APSTTIAFASSSFAAAESSSTSFHAGGPEVSSQLNACFGFQRPNLRKRRFGSGGVNLDE
                        VSKKEVGVGSNVEVSESSCVESNSGVDFGVLGPSTSSRLKIRSDFRRTIDENEDPIDQA
                        DNGVVKFQLTDADVSSKLCEKGAVPLTPCGESCAESIFQSVCSFEEKGLDVEENRLWEF
                        QLPELPRNEINETFTVSKSDSTIEQWPNSLKFESDLACTEQFSYENVSEYSSQALSELQ
                        STILLETSDTDCSDYTPSIFLESGSEFSEKSNDDAAPSSTFSMLLQYRRDFLNLNASPD
                        IRTSSSIEEEKVDQSTILRFEELDDEEAYLMFRSRERRQLIIRDYVEEYRSTTDYGDLI
                        LQQRSNVVQWIVERSRDSKLHQETTFLGVTLLDQILSRGFFKAGRHLQILGIACLTLAT
                        RIEENQSYSWFYLKAAGADSNLENRAKNFAELVLSDKVQFCYFPSTIAAAVVILASLGE
                        KQDAPSQRVIEVHKYKYLLERKLLYLYIDPIEQINKYFEIEKKL
SEQUENCE: 1
aaacattcat acttttgaag aaaattagta tattatttat ttatattata tttacagatt   60
atttattgat tattttttaa atatttattg aattttttat aatataataa aaatgtcgac   120
atgtcaacac aaaattaatt tcatattatg aattagaagt agggaataag agtatgtttg   180
gaataaattt tcaagtattt aattttaaaa ataagtcact tcaaaagaaa tataagtgtt   240
tggcaaccac tcaaactgta ttttaaaagc cattagtgtc tttattataa atactttct    300
tatcaaaagt gtttaaatga aaataaaagt ttgaagacat ttcttttcta ggttaatcga   360
atggcttcta aatttaagat ttatcaaatg tatatggtat gtttggttca aaagagtttt   420
tgagcttata attaaagaac atcaatctca tgacttatca attttttgta atgtgtattt   480
aaaaaaaaaa agaaataaaa aagaaaaaga aaagaaaaac attttgtaat aggaccctac   540
aattaaacaa tttaggacat gtctagggag tgattctaaa atagttaaat ccacttttgt   600
tattattgaa atcactttta aatatttcaa atcttccaaa cacaaaattt attatataaa   660
aattatactt aaaaatgtaa aattaaatac taaattaatt tggagtgatt taatatatgt   720
tttgggata tatccatttc aaaatcactc caaatatgaa tttcataaaa ttaaagttga    780
atatttgaaa gtagaagact aaaatggaaa agaatataga ggtgagggc caaaatgata    840
tttaactaaa taattattat tatttattag attagcacga gaggaggtga cagtgaggga   900
ccctctccaa aaaaaaaaaa aactcacttc caattcacaa ttctcttttg cttcctaact   960
tccataactg ctctgctttc catcacgaaa ctcatcttca tcttcttcat tcgaacaatg   1020
aagtccaaga agccaaggg aaatcccaaa cccgaatcct actctccgcc gaagaagaag    1080
ctccgttctc agcttccacg gcgcagacgc tctcggattt ctcctttttt ctgctccttg   1140
gactccgatt ccctgctcc ttctaccacc attgctttg cttcttcttc ctttgctgcc    1200
gccgaatcca gctccacttc cttccacgca ggcggacctg aggtttctag ccagctcaac   1260
gcgtgttttg gattccagag gccgaatttg cggaagagac gatttggttc gggtggtgtt   1320
aatttggatg aagtttcgaa gaaggaggtt ggagtaggga gtaatgtgga agtgtctgaa   1380
tcgtcttgcg ttgaatcaaa ttctggagtt gattttggtg ttctcggacc aagcactagc   1440
tccaggttga agattagaag tgattttagg agaactattg acgaaaatga agatccaatc   1500
gatcaagcgg ataatggagt tgtgaagttt caattgacgg atgctgatgt ctcgtcgaag   1560
ctttgtgaaa agggagctgt gccactcact ccttgtggag agtcttgcgc tgagtctatc   1620
ttccagagcg tttgttcgtt cgaagagaaa ggattagacg ttgaagaaaa cagactatgg   1680
gaatttcagt taccagaact accgagaaat gagatcaatg aaactttcac tgtttcgaag   1740
tcggattcga cgatagaaca gtggcctaat agcttgaagt ttgaatcgga tcttgcttgc   1800
acggagcaat tctcttatga gaatgtttcg gaatactcta gccaggcgtt gtccgagctt   1860
caatcaacaa ttctattgga gacgtctgat actgactgct tccttcaatt   1920
ttttggaat ccggaagcga attttcagag aaatcgaacg acgacgcagc tccttcgtca    1980
acatttagca tgttgctgca gtacagacgc gactttctaa acttaaatgc ctctccagac   2040
atcagaacta gctcgtctat tgaagaagag aaagtagatc aatctacggt aattcgctat   2100
cttcatgctt ccttgacgtt tcatttgcaa caaacctgaa gctaatcaaa caactatata   2160
tatatattat ttgattttaa attagatttt gagatttgaa gaattggacg atgaagaagc   2220
ctatctaatg ttcagaagta gagaaagacg ccaattgatt attcgcgact acgtagagga   2280
gtatcggtcc acaacggatt atggcgatct cattctccag caacggtcaa atgtggtcca   2340
atggatagtt gaagtaagtc cttgatacca aaccaccgtg tttctctcaa taattcctga   2400
attagcatga gatattttgc tccggttttc cattttcatc gttaatagca ttggtattct   2460
gagacattgg aactgtttag tgtatcgagg tagtttgaag cactgactct catatttcaa   2520
tttgcactga atcgctaatt agttcttaac atctcataaa atgagttccc ttgccttatt   2580
tgctatggaa ctttatccga cagcgtactt ttctgatttg gctatcccaa caatgtgatt   2640
tactaatgaa aattacaaag tcattaccat gatcatactt tccactactt aaaagccagc   2700
agtttatgat cttgcacctg ttcatctag ttgttataag ctcattctaa cgaatgaggc    2760
ctgccaccag cacaacgcat ctggcatctt gaatcaacta agtttaactg attttcatt    2820
tcttttctta cttctgcttg aatatattt ctgtttgttt ttcatcttaa taatagaata    2880
cagattcata accgcgagat ttgtgcttat tactgtggat gttgacattt tcttaggaat   2940
actccaatgt agttgcattt tcatcatctg ttgacgtttc tagttcaagg aatacattct   3000
ttatactatt tttattcctt ttctgcgtta atacttgtca ccaaccaatt gggtcaaatt   3060
ttttacatta tgttgctttg tttttgttgaa tgatgcagcg atcgagagat tccaaacttc   3120
```

```
atcaggagac gacatttta ggagttaccc tcctggacca gattctgagc agaggattct   3180
tcaaagctgg aagacacctt caaattctgg gcatagcatg tctaactttg gcgactagaa   3240
ttgaagaaaa tcagtcatac agctggtgac ttttttttcta tcttttgtct atttgtgtgc   3300
atctcagttt taactatata acaagtgttg ttcttatcta ctgtaacttc aacttaactt   3360
cgttagtatg atgaatattg cttgaaaaca aactgtatgc cagttggtct tcttgtttcg   3420
atccaaggga gtgaaattgg gtaagttagg atcgaatgct aagtagtact agaaataata   3480
atcagaaaga attgtattaa agtaattgaa tctaatagtc ttgaatattt tttctaaagt   3540
tcaaagtgtc gagcctgaaa gctttgcgtt tacatggacc aaagtaatgt tgtgaatata   3600
tcgtaggtcc tcttatagca attatgtaac aaataaatagc catacattag tgtcgataca   3660
caccacccgt acggtactgt agtcgaatat tgccataaca ctatctttca gttcttatgt   3720
taacaattca tgtgcacaga agagacccga gacccaccaa gaaaacatta tctttgactt   3780
gtatatagaa ctctcaagtcg agtcaaatgt aaaacaattc ttttttcttct cttctctttc   3840
tcaaacttcc ttttgtagcc ttcatttatc tttgacttgc aatttacatg caaaatgtta   3900
aataattgtg atttgtttaa ttaaatagag ccttgtgaat tgagaaggta tccaagctag   3960
ctggtgggtc tcgagcttgg tggatatatt tataaagcta tgataggact gatttgtttt   4020
attttgggc atttcagggt gcagcaaagg aatatccgtg tagagagcaa cacgtacaga   4080
agatctgaag ttgttggcat ggaatggctt gttgaagaag tcttaaagtt ccattgtttc   4140
ttgccaactg tttacaactt cttatggtac atcttccttt gactaacttg accattggtg   4200
ggaagggaaa aagttttccc tttcgtgcat ccattttcaa taaactcctt ccgcccatta   4260
acaatttgaa tctactgcga ataacatgct ttatttaatt ttcttttttt gaaaattatc   4320
ttaggttcta cctgaaagct gctggagctg actcgaattt ggagaatcga gctaagaact   4380
ttgcggagct ggttctttca gacaaagtcc aattttgtta tttcccttca actattgcag   4440
ctgcggttgt catcttggcg tccctaggag aaaaacaaga tgcaccaagt caacgagtca   4500
ttgaggtaca taaatacaaa tacctgttag agagaaaact cctttatctt tatattgacc   4560
caattgaaca aataaacaag tattttgaaa tcgagaagaa actttaaagt tttacaaaaa   4620
caccataatc taaatccaat tagattcaac tgtaatgtaa agtacaataa taaaatacat   4680
ataccataag gaaatggtag gttatagtgt ttgtttcaat tagatattca atttatatat   4740
tagttagtgt tgttaatctc cctgaatatt tcttactaac ttgaggaagg tctcctgtct   4800
tctggaaacc cttccatgcc caaaatttca gccttctgct attcccatta agtcaaacat   4860
gtaatgagtt tactttttctt tctccttcta attattaatt atttttaata atttatttgt   4920
ctaattcatt ttctgtagtc tgaacccacg aacttgctta tcacaaaatc caaaaccaaa   4980
aaccccatca caattttgga aatctttttg agaactgcta ctataaccat gtaatttctt   5040
tcaaaatcta caaaaataga aataacactt atttagacta tctgtggtac tatctcataa   5100
catctggtgc attgtggctt tgcagacgca tgtca                             5135
```

```
SEQ ID NO: 2             moltype = AA  length = 562
FEATURE                  Location/Qualifiers
source                   1..562
                         mol_type = protein
                         organism = Citrullus lanatus
SEQUENCE: 2
MKSKKPRANP KPESYSPPKK KLRSQLPRRR RSRISPFFCS LDSDSPAPST TIAFASSSFA   60
AAESSSTSFH AGGPEVSSQL NACFGFQRPN LRKRRFGSGG VNLDEVSKKE VGVGSNVEVS   120
ESSCVESNSG VDFGVLGPST SSRLKIRSDF RRTIDENEDP IDQADNGVVK FQLTDADVSS   180
KLCEKGAVPL TPCGESCAES IFQSVCSFEE KGLDVEENRL WEFQLPELPR NEINETFTVS   240
KSDSTIEQWP NSLKFESDLA CTEQFSYENV SEYSSQALSE LQSTILLETS DTDCSDYTPS   300
IFLESGSEFS EKSNDDAAPS STFSMLLQYR RDFLNLNASP DIRTSSSIEE EKVDQSTILR   360
FEELDDEEAY LMFRSRERRQ LIIRDYVEEY RSTTDYGDLI LQQRSNVVQW IVERSRDSKL   420
HQETTFLGVT LLDQILSRGF FKAGRHLQIL GIACLTLATR IEENQSYSWF YLKAAGADSN   480
LENRAKNFAE LVLSDKVQFC YFPSTIAAAV VILASLGEKQ DAPSQRVIEV HKYKYLLERK   540
LLYLYIDPIE QINKYFEIEK KL                                            562
```

```
SEQ ID NO: 3             moltype = RNA  length = 1673
FEATURE                  Location/Qualifiers
source                   1..1673
                         mol_type = other RNA
                         organism = synthetic construct
misc_feature             1..1673
                         note = Induced by mutation
mRNA                     1..1673
CDS                      1..1098
                         note = The CDS-derived protein, which was originally shown
                          below the RNA in the original St25 listing, is given by
                          Seq-ID 4
                         protein_id = 4
                         translation = MKSKKPRANPKPESYSPPKKKLRSQLPRRRRSRISPFFCSLDSDSP
                          APSTTIAFASSSFAAAESSSTSFHAGGPEVSSQLNACFGFQRPNLRKRRFGSGGVNLDE
                          VSKKEVGVGSNVEVSESSCVESNSGVDFGVLGPSTSSRLKIRSDFRRTIDENEDPIDQA
                          DNGVVKFQLTDADVSSKLCEKGAVPLTPCGESCAESIFQSVCSFEEKGLDVEENRLWEF
                          QLPELPRNEINETFTVSKSDSTIEQWPNSLKFESDLACTEQFSYENVSEYSSQALSELQ
                          STILLETSDTDCSDYTPSIFLESGSEFSEKSNDDAAPSSTFSMLLQYRRDFLNLNASPD
                          IRTSSSIEEEKVDQSTNWTMKKPI
SEQUENCE: 3
atgaagtcca agaagccaag ggcaaatccc aaacccgaat cctactctcc gccgaagaag   60
aagtccgtt ctcagcttcc acggcgcaga cgctctcgga tttctccttt tttctgctcc   120
ttggactccg attcccctgc tccttctacc accattgctt tgcttcttc ttcctttgct   180
gccgccgaat ccagctccac ttccttccac gcaggcggac ctgaggtttc tagccagctc   240
aacgcgtgtt ttggattcca gaggccgaat ttgcggaaga cgacgatttgg ttcgggtggt   300
gttaatttgg atgaagtttc gaagaaggag gttggagtag ggagtaatgt ggaagtgtct   360
```

-continued

```
gaatcgtctt gcgttgaatc aaattctgga gttgattttg gtgttctcgg accaagcact   420
agctccaggt tgaagattag aagtgatttt aggagaacta ttgacgaaaa tgaagatcca   480
atcgatcaag cggataatgg agttgtgaag tttcaattga cggatgctga tgtctcgtcg   540
aagctttgtg aaaagggagc tgtgccactc actccttgtg gagagtcttg cgctgagtct   600
atcttccaga gcgtttgttc gttcgaagag aaaggattga acgttgaaga aaacagacta   660
tgggaatttc agttaccaga actaccgaga aatgagatca atgaaactttc cactgtttcg   720
aagtcggatt cgacgataga acagtggcct aatagcttga agtttgaatc ggatcttgct   780
tgcacggagc aattctctta tgagaatgtt tcggaatact ctagccaggc gttgtccgag   840
cttcaatcaa caattctatt ggagacgtct gatactgact gctcagatta cactccttca   900
attttttttgg aatccggaag cgaattttca gagaaatcga acgacgacgc agctccttcg   960
tcaacattta gcatgttgct gcagtacaga cgcgactttc taaacttaaa tgcctctcca   1020
gacatcagaa ctagctcgtc tattgaagaa gagaaagtag atcaatctac gaattggacg   1080
atgaagaagc ctatctaatg ttcagaagta gagaaagacg ccaattgatt attcgcgact   1140
acgtagagga gtatcggtcc acaacggatt atggcgatct cattctccag caacggtcaa   1200
atgtggtcca atggatagtt gaacgatcga gagattccaa acttcatcag gagacgacat   1260
tttaggagt taccctcctg gaccagattc tgagcagagg attcttcaaa gctggaagac   1320
accttcaaat tctgggcata gcatgtctaa ctttggcgac tagaattgaa gaaaatcagt   1380
catacagctg gttctacctg aaagctgctg gagctgaatc gaatttggag aatcgagcta   1440
agaactttgc ggagctggtt ctttcagaca aagtccaatt ttgttatttc ccttcaacta   1500
ttgcagctgc ggttgtcatc ttggcgtccc taggagaaaa acaagatgca ccaagtcaac   1560
gagtcattga ggtacataaa tacaaatacc tgttagagag aaaactcctt tatctttata   1620
ttgacccaat tgaacaaata aacaagtatt ttgaaatcga gaagaaactt taa           1673
```

```
SEQ ID NO: 4              moltype = AA   length = 365
FEATURE                   Location/Qualifiers
source                    1..365
                          mol_type = protein
                          organism = synthetic construct
REGION                    1..365
                          note = Synthetic Construct
SEQUENCE: 4
MKSKKPRANP KPESYSPPKK KLRSQLPRRR RSRISPFFCS LDSDSPAPST TIAFASSSFA   60
AAESSSTSFH AGGPEVSSQL NACFGFQRPN LRKRRFGSGG VNLDEVSKKE VGVGSNVEVS   120
ESSCVESNSG VDFGVLGPST SSRLKIRSDF RRTIDENEDP IDQADNGVVK FQLTDADVSS   180
KLCEKGAVPL TPCGESCAES IFQSVCSFEE KGLDVEENRL WEFQLPELPR NEINETFTVS   240
KSDSTIEQWP NSLKFESDLA CTEQFSYENV SEYSSQALSE LQSTILLETS DTDCSDYTPS   300
IFLESGSEFS EKSNDDAAPS STFSMLLQYR RDFLNLNASP DIRTSSSIEE EKVDQSTNWT   360
MKKPI                                                               365
```

```
SEQ ID NO: 5              moltype = DNA   length = 2348
FEATURE                   Location/Qualifiers
source                    1..2348
                          mol_type = unassigned DNA
                          organism = Cucumis melo
CDS                       192..1925
                          note = The CDS-derived protein, which was originally shown
                           below the DNA in the original St25 listing, is given by
                           Seq-ID 6
                          protein_id = 6
                          translation = MKSKKRRPNPNPQSFSPPKNKKLRSHLPRRKRPRISPFLCSNLVSH
                           SPAPSTTFALAAAESTSTSFYTSRPDVSSHLSAPNFRKRRFDSKKEVGVGSNVEVSESS
                           CVESNSGVDFGVSGPSTTSKLKNRSSFRTTINGNEDQIDPAENGVEKFEFTDVDVSSKL
                           CGKEAVVLTSCVESCAESIFQSVCPFEEKRLEVEDNRLWEFQLPELPRNEINETFTVSK
                           SDSTIEQWPGSLKFESDLACTEQFSYDDVSEYSSQALSLQSTILLETSDEYCSDYTPSI
                           FLESGSEFSEKSNEDAAPSSTFRMLLQYRRDFLSLNSSPDIRTSSPIEEEKVDQSTILR
                           FEELDDEEAYRMFRNRERRQLIIHDYIEEYRSTTDYGDLILQQRSNMVQWIVERSRENK
                           LHQETTFLGVTLLDQILSKGFFKAESRLQILGIACLTLATRIEENQSYSWLQQRNIHVG
                           SNTYRRAEVVGMEWLVEEVLKFHCFLPTVYNFLWFYLKAAGANSDLENRAKNFAVLVLA
                           DKVQFCYFPSTIAAAVVILASLGEKQDAPSQRVIETHVRTENDDLPECIESLEWLLKLL
misc_feature              1..2348
                          note = GenBank/XM_008454203.1 ( 2014-06-25); pos.: 1..2348
SEQUENCE: 5
aactgataaa aacattccaa attgagggat caaaatgata ttttacacga aaaggaggag   60
gagggtggga cccacttcga gagaaacctc aattcgaatt cacatttctc ccttcgcttc   120
tttaacttcc taactgctct gctttccatc acgaaactcc atcttcatct tcctccttaa   180
tcgcaaacac catgaaatcc aagaaacgaa ggcctaatcc caaccctcaa tccttctctc   240
cacccaagaa caagaagctc cgttctcacc ttccacgccg caaacgcccg aggatttcac   300
cttttctctg ctctaatttg gtttcccatt cccccgctcc ctccaccacc tttgctttgg   360
ctgccgcaga atccacctcc acttccttct cacacatccg acctgacgtt tctagccacc   420
tcagcgctcc caatttcagg aagagacgat ttgattccaa gaaggaggtt ggagtaggga   480
gtaatgtgga agtgtctgaa tcttcttgtg ttgaatctaa ttctggagtt gattttggtg   540
tttccggacc aagcactact tcgaagttaa agaataggag tagttttagg acaactatta   600
acggaaatga agatcaaatt gatccagcgg agaatggagt tgaaaagttc gaattcacgg   660
atgttgatgt ctcgtcgaag ctttgtggaa aggaagctgt ggtactcact tcttgtgtag   720
agtcttgtgc tgaatctatc tttcagagtg tttgtccgtt cgaagagaaa cgattagaag   780
ttgaagataa cagactatgg gaatttcagt tacctgagct accagagaat gagattaatg   840
aaactttcac tgtttcgaag tcggattcga cgatagaaca gtggcctggc agcttgaagt   900
ttgaatcgga tcttgcttgc acggagcaat ctcttacga tgatgtttcg gaatactcta   960
```

```
gccaggcgtt gtcgcttcag tcaactattc tattggagac ttctgatgag tactgctcag     1020
attacactcc atcaattttc ttggaatccg gaacgaatt ttcagagaaa tcgaacgaag      1080
acgcagctcc ttcatcgaca tttagaatgt tgctgcagta cagacgcgac tttctaagct     1140
taaattcctc tccagacatc agaactagct cgcctattga agaagaaaaa gtagatcaat     1200
ctacgattct gagatttgaa gaattggacg acgaagaagc ctatcgaatg ttcagaaata     1260
gagaaagacg ccaattgatt attcacgact acatagagga gtatcgatcc acaacggatt     1320
atggcgatct cattcttcag caacggtcaa atatggtcca atggatagtt gaacgatcta     1380
gagaaaacaa acttcatcag gagacgacat ttttaggagt taccctttcta gaccagattc     1440
tgagcaaagg attcttcaaa gctgaaagtc gccttcaaat tctaggcata gcatgtctaa     1500
ctttggcgac tagaattgaa gaaaatcagt catacagctg gttacagcaa aggaatatcc     1560
atgtagggag caacacgtac agaagagcag aagttgttgg catggaatgg cttgttgaag     1620
aagttcttaa gttccattgt ttcttgccaa ctgtttacaa cttcttgtgg ttctacctga     1680
aagctgctgg agctaactca gatttggaga atcgagctaa gaatttcgca gtgctcgttc     1740
ttgcagacaa agtccaattt tgttatttcc cttcaacaat tgcagctgca gttgtcatct     1800
tggcgtcctt aggagaaaaa caagatgcac caagtcaacg agtcattgag acacatgtca     1860
gaacagaaaa cgacgatctg cctgaatgta tcgagagctt ggagtggcta ttaaagcttt     1920
tatgatggaa gcatcaaatc ctaacacagc aaaaaagaaa gcaagcaatt ggtcttttg     1980
acatattctt gaccacttaa acatcatctt gaacacagct agtgaagctc accctccgaa     2040
accagctata taggtaagac attcatcaat tcagttctct tctattctat caccaacaga     2100
atgaaaattt ggtttttcct ttcaaatttt attataacaa gagattgaat caggacctag     2160
tcaagtccaa aaccaaatag tatttgatgt tcatttacat gctttcataa tttcatgtat     2220
ttagtagtgt tgaattacag gatgtatgta attgatactc agacctaatg actctatatt     2280
cttcaccaaa acaaacaatg gttacgatga gattttcaat actcgagcaa ttgaagctta     2340
aaatgtaa                                                              2348

SEQ ID NO: 6              moltype = AA   length = 577
FEATURE                  Location/Qualifiers
source                   1..577
                         mol_type = protein
                         organism = Cucumis melo
SEQUENCE: 6
MKSKKRRPNP NPQSFSPPKN KKLRSHLPRR KRPRISPFLC SNLVSHSPAP STTFALAAAE      60
STSTSFYTSR PDVSSHLSAP NFRKRRFDSK KEVGVGSNVE VSESSCVESN SGVDFGVSGP     120
STTSKLKNRS SFRTTINGNE DQIDPAENGV EKFEFTDVDV SSKLCGKEAV VLTSCVESCA     180
ESIFQSVCPF EEKRLEVEDN RLWEFQLPEL PRNEINETFT VSKSDSTIEQ WPGSLKFESD     240
LACTEQFSYD DVSEYSSQAL SLQSTILLET SDEYCSDYTP SIFLESGSEF SEKSNEDAAP     300
SSTFRMLLQY RRDFLSLNSS PDIRTSSPIE EEKVDQSTIL RFEELDDEEA YRMFRNRERR     360
QLIIHDYIEE YRSTTDYGDL ILQQRSNMVQ WIVERSRENK LHQETTFLGV TLLDQILSKG     420
FFKAESRLQI LGIACLTLAT RIEENQSYSW LQQRNIHVGS NTYRRAEVVG MEWLVEEVLK     480
FHCFLPTVYN FLWFYLKAAG ANSDLENRAK NFAVLVLADK VQFCYFPSTI AAAVVILASL     540
GEKQDAPSQR VIETHVRTEN DDLPECIESL EWLLKLL                              577

SEQ ID NO: 7              moltype = DNA   length = 38
FEATURE                  Location/Qualifiers
source                   1..38
                         mol_type = other DNA
                         organism = synthetic construct
misc_feature             1..38
                         note = Primer
SEQUENCE: 7
gtaaaacgac ggccagttgc ctctccagac atcagaac                              38

SEQ ID NO: 8              moltype = DNA   length = 38
FEATURE                  Location/Qualifiers
source                   1..38
                         mol_type = other DNA
                         organism = synthetic construct
misc_feature             1..38
                         note = Primer
SEQUENCE: 8
caggaaacag ctatgaccaa tccgttgtgg accgatac                              38

SEQ ID NO: 9              moltype = DNA   length = 38
FEATURE                  Location/Qualifiers
source                   1..38
                         mol_type = other DNA
                         organism = synthetic construct
misc_feature             1..38
                         note = Primer
SEQUENCE: 9
gtaaaacgac ggccagtgct ccttcgtcaa catttagc                              38

SEQ ID NO: 10             moltype = DNA   length = 40
FEATURE                  Location/Qualifiers
source                   1..40
                         mol_type = other DNA
                         organism = synthetic construct
misc_feature             1..40
                         note = Primer
```

-continued

```
SEQUENCE: 10
caggaaacag ctatgacctt ggcgtctttc tctacttctg                              40

SEQ ID NO: 11              moltype = DNA   length = 38
FEATURE                   Location/Qualifiers
source                    1..38
                          mol_type = other DNA
                          organism = synthetic construct
misc_feature              1..38
                          note = Primer
SEQUENCE: 11
caggaaacag ctatgaccct ggtccaggag ggtaactc                                38

SEQ ID NO: 12             moltype = AA   length = 569
FEATURE                   Location/Qualifiers
source                    1..569
                          mol_type = protein
                          organism = Cucumis sativus
SEQUENCE: 12
MKSKKRRPNP KPQSFSPPKN KKLRSQLPRR KRPLILPFFC CYLDSDSPPP STTFSFASSS        60
SFTAAQSTST SFFPTGPEVS SHLNPLNFRK TRFDSNKEVG VGSNEQVSES SCVESNSGLD        120
FGVSGPSTTS KLKNRRTIHG NEDPIDPAEN GVDASSKLCG KGAVVLTSCV ESCAESIFQS        180
VCSFEEKGLE VEDNRLWEFQ LPELQKNEIN KTFTVSKSDS TIEQWPGSLK IESDLACTEQ        240
FSYDDVSEYL SQPLSLQSTI LLEMSDDCSD YTPSIFLESG SEFSEKSNED AAPTSTFTML        300
LQYRREFISL NFSHIRTSSS IEEEEVDQST ILRFEELDDE EAYRMFRNRE RRQLIICDYI        360
EEYRSTTDYG DFILQQRSNM VQWIVERSRE KKLHQETTFL GVTLLDQILS KGFFKAETHL        420
QILGIACLTL ATRIEENQSY SWLQQRNIHV GSNTYRRSKV VGMEWLVEEV LKFHCFLPTV        480
YNFLWFYLKA AGANSDLENR AKNFAVLVLA EKVQFCYFPS TIAAAVVILA SLGEKQDAPS        540
ERVIEIHVRT ENDDLPECIE SLEWLLKFL                                         569

SEQ ID NO: 13             moltype = DNA   length = 50
FEATURE                   Location/Qualifiers
source                    1..50
                          mol_type = other DNA
                          organism = synthetic construct
misc_feature              1..50
                          note = sequence of sample 114 and 115 of Figure 2
SEQUENCE: 13
acgattttga gatttgaaga attggacgat gaagaagcct atctaatgtt                   50

SEQ ID NO: 14             moltype = AA   length = 17
FEATURE                   Location/Qualifiers
source                    1..17
                          mol_type = protein
                          organism = synthetic construct
REGION                    1..17
                          note = sequence of sample 114 and 115 of Figure 2
SEQUENCE: 14
TILRFEELDD EEAYLMF                                                       17

SEQ ID NO: 15             moltype = DNA   length = 34
FEATURE                   Location/Qualifiers
source                    1..34
                          mol_type = other DNA
                          organism = synthetic construct
misc_feature              1..34
                          note = sequence of sample 116 and 117 of Figure 2
SEQUENCE: 15
acgaattgga cgatgaagaa gcctatctaa tgtt                                    34

SEQ ID NO: 16             moltype = AA   length = 9
FEATURE                   Location/Qualifiers
source                    1..9
                          mol_type = protein
                          organism = synthetic construct
REGION                    1..9
                          note = sequence of sample 116 and 117 of Figure 2
SEQUENCE: 16
TNWTMKKPI                                                                9

SEQ ID NO: 17             moltype = DNA   length = 1689
FEATURE                   Location/Qualifiers
source                    1..1689
                          mol_type = other DNA
                          organism = synthetic construct
misc_feature              1..1689
                          note = Citrullus lanatus - cDNA of cyclin SDS like gene
                           comprising a C to T mutation of  nucleotide 670 resulting
                           in a STOP codon
```

```
CDS                 1..672
                    note = The CDS-derived protein, which was originally shown
                     below the DNA in the original St25 listing, is given by
                     Seq-ID 18
                    protein_id = 18
                    translation = MKSKKPRANPKPESYSPPKKKLRSQLPRRRRSRISPFFCSLDSDSP
                    APSTTIAFASSSFAAAESSSTSFHAGGPEVSSQLNACFGFQRPNLRKRRFGSGGVNLDE
                    VSKKEVGVGSNVEVSESSCVESNSGVDFGVLGPSTSSRLKIRSDFRRTIDENEDPIDQA
                    DNGVVKFQLTDADVSSKLCEKGAVPLTPCGESCAESIFQSVCSFEEKGLDVEENRLWEF SEQUENCE: 17
atgaagtcca agaagccaag ggcaaatccc aaacccgaat cctactctcc gccgaagaag    60
aagctccgtt ctcagcttcc acggcgcaga cgctctcgga tttctccttt tttctgctcc   120
ttggactccg attcccctgc tccttctacc accattgctt ttgcttcttc ttcctttgct   180
gccgccgaat ccagctccac ttccttccac gcaggcggac ctgaggtttc tagccagctc   240
aacgcgtgtt ttggattcca gaggccgaat ttgcggaaga gacgatttgg ttcgggtggt   300
gttaatttgg atgaagtttc gaagaaggag gttggagtag ggagtaatgt ggaagtgtct   360
gaatcgtctt gcgttgaatc aaattctgga gttgattttg gtgttctcgg accaagcact   420
agctccaggt tgaagattag aagtgatttt aggagaacta ttgacgaaaa tgaagatcca   480
atcgatcaag cggataatgg agttgtgaag tttcaattga cggatgctga tgtctcgtcg   540
aagctttgtg aaaaggggagc tgtgccactc actccttgtg gagagtcttg cgctgagtct   600
atcttccaga gcgtttgttc gttcgaagag aaaggattag acgttgaaga aaacagacta   660
tgggaatttt agttaccaga actaccgaga aatgagatca atgaaacttt cactgtttcg   720
aagtcggatt cgacgataga acagtggcct aatagcttga agtttgaatc ggatcttgct   780
tgcacggagc aattctctta tgagaatgtt tcggaatact ctagccaggc gttgtccgag   840
cttcaatcaa caattctatt ggagacgtct gatactggtt gatactgatt cactccttca   900
attttttttgg aatccggaag cgaattttca gagaaatcga acgacgacgc agctccttcg   960
tcaacatttta gcatgttgct gcagtacaga cgcgactttc taaacttaaa tgcctctcca  1020
gacatcagaa ctagctcgtc tattgaagaa gagaaagtag atcaatctac gattttgaga  1080
tttgaagaat tggacgatga agaagcctat ctaatgttca gaagtagaga aagacgccaa  1140
ttgattattc gcgactacgt gagaggagtat cggtccacaa cggattatgg cgatctcatt  1200
ctccagcaac ggtcaaatgt ggtccaatgg atagttgaac gatcgagaga ttccaaactt  1260
catcaggaga cgacatttttt aggagttacc ctcctggacc agattctgag cagaggattc  1320
ttcaaagctg gaagacacct tcaaattctg ggcatagcat gtctaacttt ggcgactaga  1380
attgaagaaa atcagtcata cagctggttc tacctgaaag ctgctggagc tgactcgaat  1440
ttggagaatc gagctaagaa ctttgcggag ctggttcttt cagacaaagt ccaatttgt   1500
tatttcccctt caactattgc agctgcggtt gtcatcttgg cgtccctagg agaaaaacaa  1560
gatgcaccaa gtcaacgagt cattgaggta cataaataca aatacctgtt agagagaaaa  1620
ctcctttatc tttatattga cccaattgaa caaataaaca agtattttga aatcgagaag  1680
aaactttaa                                                          1689

SEQ ID NO: 18       moltype = AA  length = 223
FEATURE             Location/Qualifiers
source              1..223
                    mol_type = protein
                    organism = synthetic construct
REGION              1..223
                    note = Synthetic Construct
SEQUENCE: 18
MKSKKPRANP KPESYSPPKK KLRSQLPRRR RSRISPFFCS LDSDSPAPST TIAFASSSFA    60
AAESSSTSFH AGGPEVSSQL NACFGFQRPN LRKRRFGSGG VNLDEVSKKE VGVGSNVEVS   120
ESSCVESNSG VDFGVLGPST SSRLKIRSDF RRTIDENEDP IDQADNGVVK FQLTDADVSS   180
KLCEKGAVPL TPCGESCAES IFQSVCSFEE KGLDVEENRL WEF                     223

SEQ ID NO: 19       moltype = AA  length = 590
FEATURE             Location/Qualifiers
source              1..590
                    mol_type = protein
                    organism = synthetic construct
REGION              1..590
                    note = Solanum lycopersicum
SEQUENCE: 19
MKRKLHAEAV QPAVQQPKEI LPAVKRQLRS KLPRRKRSHI SPILRSFSIA ASSYLTSEVS    60
RQSSKGSVNK EVKKREIEGE EFRRITRAYF RKKLLVDQKK DSEVELSECS CVDSCSEVIG   120
KIIKIEDPVD ISRDIVSKRN RNAKVIEGTE DSEVISRFLK ASGGFCGESS KSGEDAVARS   180
RNAAKIIHED VVSFNSVLQS PSESKCGNLS VQSIKCSENR AAEEVESEVS RVCPEVELSA   240
VEQAHEKLVE AELDLECSEN FSIVDVSDDY SSAYSELQSE IFPESSDIDI SDYSPSYWYD   300
SGSQFSEKSN ADASPSPTFT LFLRFGQQFC RSTAALQSTP INSSEDQIST EFTGLEDEED   360
EESYRMIRNR ERRQLYLHDY AEEYCSTTDY GDLIVQQRLQ MVHWILEQAT RKDLQKETMF   420
LSVNLFDRFL SKGYFKTKRC LQIAGIACLT LAVRIEENQP FNSIRQKTFS VAGTTYSCSE   480
VVAMEWLVQE VLNFQCFLPT IYNFLWFYLK AATATEYMEK TAKYLAVLAL LGHEHLCYRP   540
STVASALVIL ALSAANLYAS CHLVTKTHAK IEDEDLPECI KSLEWLVKYI              590

SEQ ID NO: 20       moltype = AA  length = 560
FEATURE             Location/Qualifiers
source              1..560
                    mol_type = protein
                    organism = Capsicum annuum
SEQUENCE: 20
```

-continued

```
MKRNLHAEAA  EILPAMKKQL  RSKLPRRKRS  HISPILLSVN  KETVVVVKKK  REIEVDEFRR   60
ITRAYLKKKD  AEVELSECSC  VDSCSEIVGK  IVKIEDPVDI  SHDIVSKQKR  NAKVVEGTED  120
SDAISFLKNA  SGFFGESSKS  GVDVSVEGSR  TTEKINDEDV  VSFNSVLQSP  SESKCGNLSV  180
QTIKCTENRA  AEEDIESEVS  RIYPEVELSA  LENANEKLVE  PEFDLECSEN  FSVLDVTADY  240
SSAYSELQSE  IFPESSDFDL  SDYSPSYWYD  SGSQFSEKSN  GDATPSPTLT  LFLRFSQQFC  300
RSTAALQFTS  VNSSEDHIST  EITGLKDEED  EESYMLIRNR  ERRQLYLHDY  AEEYCSTTDS  360
GDLIVQQRLL  MVHWILEQAT  RKDLLKETMF  LSVNLFDRFL  SKGYFKTKRC  LQIVGIACLT  420
LAVRIEENQP  FNSIRQKTFT  VAGTAYSCSE  VVAMEWLVQE  VLNFQCFLPT  IYNFLWFYLK  480
AARATEYMER  TTKYLAVLAL  LGHEHLCYRP  STVASALVIL  ALSAANLYVS  CHLVTKTHAK  540
IKDEDLPECI  KSLEWLVKYI                                                 560

SEQ ID NO: 21              moltype = DNA  length = 23
FEATURE                    Location/Qualifiers
source                     1..23
                           mol_type = other DNA
                           organism = synthetic construct
misc_feature               1..23
                           note = Forward primer
SEQUENCE: 21
cgaagagaaa ggattagacg ttg                                                 23

SEQ ID NO: 22              moltype = DNA  length = 22
FEATURE                    Location/Qualifiers
source                     1..22
                           mol_type = other DNA
                           organism = synthetic construct
misc_feature               1..22
                           note = reverse primer
SEQUENCE: 22
tctgagcagt cagtatcaga cg                                                  22
```

The invention claimed is:

1. A method for production of a seedless watermelon fruit comprising growing a watermelon plant and allowing pollination of said plant and harvesting the seedless fruit, wherein the watermelon plant comprises a mutant allele of a gene encoding a cyclin SDS like protein in homozygous form, wherein the mutant allele comprises a mutation in the promoter sequence resulting in no gene expression or reduced gene expression compared to a corresponding wild type allele or wherein the mutant allele encodes a non-functional protein or a reduced-function protein comprising a deletion, truncation, insertion or replacement of one or more amino acids, compared to the protein encoded by the wild type allele, wherein the cyclin SDS like protein of the wild type allele is encoded by one of the following nucleic acid molecules:

a) a nucleic acid molecule, which encodes a protein with the amino acid sequence given under SEQ ID NO: 2;

b) a nucleic acid molecule, which encodes a protein, the sequence of which has an identity of at least 80% with the amino acid sequence given under SEQ ID NO: 2;

c) a nucleic acid molecule, which comprises the nucleotide sequence shown under SEQ ID NO: 1 or the complimentary sequence thereof; or d) a nucleic acid molecule, which has an identity of at least 90% with one of the nucleic acid sequences described under c).

2. The method according to claim 1, wherein the mutant allele of a gene encoding a cyclin SDS like protein encodes a non-functional protein in which one or more amino acids are inserted, replaced or deleted.

3. The method according to claim 1, wherein the mutant allele of a gene encoding a cyclin SDS like protein encodes a non-functional protein in which one or more amino acids are inserted, replaced or deleted in the conserved Cyclin N domain and/or Cyclin C domain of the protein.

4. The method according to claim 1, wherein the watermelon plant is a vegetatively propagated plant.

5. The method according to claim 1, wherein the mutant allele encodes a non-functional protein which is truncated and lacks the Cyclin_N and Cyclin_C domains.

6. The method according to claim 1, wherein the mutant allele encodes a non-functional protein which lacks amino acids encoded by exons 2, 3 and/or 4 of the wild type cyclin SDS like protein.

7. The method according to claim 1, wherein the mutant allele comprises a mutation which results in a premature stop codon.

8. The method according to claim 1, wherein the cyclin SDS like protein of the wild type allele is encoded by a nucleic acid molecule, which encodes a protein with the amino acid sequence given under SEQ ID NO: 2.

9. The method according to claim 1, wherein the cyclin SDS like protein of the wild type allele is encoded by a nucleic acid molecule, which encodes a protein, the sequence of which has an identity of at least 80% with the amino acid sequence given under SEQ ID NO: 2.

10. The method according to claim 1, wherein the cyclin SDS like protein of the wild type allele is encoded by a nucleic acid molecule, which comprises the nucleotide sequence shown under SEQ ID NO: 1 or the complimentary sequence thereof.

11. The method according to claim 1, wherein the cyclin SDS like protein of the wild type allele is encoded by a nucleic acid molecule, which has an identity of at least 90% with one of the nucleic acid sequences described under c).

* * * * *